United States Patent
Yin et al.

(10) Patent No.: US 11,466,010 B2
(45) Date of Patent: Oct. 11, 2022

(54) TOLL-LIKE RECEPTOR 8 (TLR8) SPECIFIC ANTAGONISTS AND METHODS OF MAKING AND USES THEREOF

(71) Applicant: The Regents of the University of Colorado, a body corporate, Denver, CO (US)

(72) Inventors: Hang Hubert Yin, Boulder, CO (US); Shuting Zhang, Boulder, CO (US); Zhenyi Hu, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 16/760,815

(22) PCT Filed: Oct. 30, 2018

(86) PCT No.: PCT/US2018/058286
§ 371 (c)(1),
(2) Date: Apr. 30, 2020

(87) PCT Pub. No.: WO2019/089648
PCT Pub. Date: May 9, 2019

(65) Prior Publication Data
US 2021/0179621 A1    Jun. 17, 2021

Related U.S. Application Data

(60) Provisional application No. 62/579,015, filed on Oct. 30, 2017.

(51) Int. Cl.
| | | |
|---|---|---|
| C07D 487/04 | (2006.01) | |
| C07D 215/18 | (2006.01) | |
| C07D 215/20 | (2006.01) | |
| C07D 401/04 | (2006.01) | |

(52) U.S. Cl.
CPC ......... *C07D 487/04* (2013.01); *C07D 215/18* (2013.01); *C07D 215/20* (2013.01); *C07D 401/04* (2013.01)

(58) Field of Classification Search
CPC .. C07D 215/18; C07D 215/20; C07D 487/04; C07D 401/04
See application file for complete search history.

(56) References Cited

U.S. PATENT DOCUMENTS

| | | |
|---|---|---|
| 2016/0326161 A1 | 11/2016 | Carlson et al. |
| 2017/0174653 A1 | 6/2017 | Sherer et al. |

FOREIGN PATENT DOCUMENTS

WO    2015095780 A1    6/2015

OTHER PUBLICATIONS

Zhang, Nature Chemical Biology, vol. 14, Jan. 2018, 58-66. (Year: 2018).*
Hu, Bioorg Med Chem, Jan. 2018, vol. 26(1), 77-83. (Year: 2018).*
Li, Chem Eur J, 2017, vol. 23, 15300-15304. (Year: 2017).*
Sapkota, New J Chem, 2017, vol. 41, 5395-5402. (Year: 2017).*
Yuan, Org Chem Front, 2017, vol. 4 545-554. (Year: 2017).*
Li (2), RSC Adv, 2015, 88214-88217. (Year: 2015).*
Wolf, Eur J Org Chem, 2006, 1917-1925. (Year: 2006).*
Cacchi, Tetrahedron, vol. 52(30), 1996, 10225-10240. (Year: 1996).*
Kenner, The Constitution of Apocinchene, 1935, 299-303. (Year: 1935).*
Zhang, et al., "Small-molecule inhibition of TLR8 through stabilization of its resting state", Nature Chemical biology, Nov. 20, 2017, vol. 14, pp. 58-64.
International Search Report dated Feb. 19, 2019 in PCT Application No. PCT/US18/58286, 4 pages.
International Preliminary Report on Patentability dated May 5, 2020 in International Application No. PCT/US2018/058286, 6 pages.
Written Opinion dated Feb. 19, 2019 in International Application No. PCT/US2018/058286, 5 pages.

* cited by examiner

*Primary Examiner* — D Margaret M Seaman
(74) *Attorney, Agent, or Firm* — Berg Hill Greenleaf Ruscitti LLP

(57) ABSTRACT

Toll-like receptor 8 (TLR8)-specific inhibitors and methods of using the same in individuals having an autoimmune disease or an inflammatory disorder.

16 Claims, 20 Drawing Sheets

Triptolide

CU-CPT9a R=OMe
CU-CPT9b R=OH

TLR8 vs CU-CPT9b

CU-CPT8m

| | | |
|---|---|---|
| CU-CPT9a | $R^1$= OMe, $R^2$=H, X=C |
| CU-CPT9b | $R^1$= OH, $R^2$=H, X=C |
| CU-CPT9c | $R^1$= Cl, $R^2$=H, X=C |
| CU-CPT9d | $R^1$= OMe, $R^2$=(CH$_2$)$_4$OH, X=C |
| CU-CPT9e | $R^1$= OH, $R^2$=Me, X=N |
| CU-CPT9f | $R^1$= OMe, $R^2$=Bn, X=N |

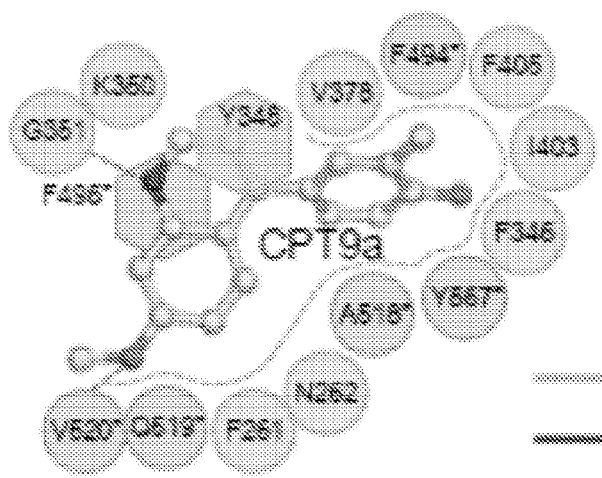
FIG. 17
— Hydrophobic pocket
═ Hydrogen bond
≡ Halogen bond
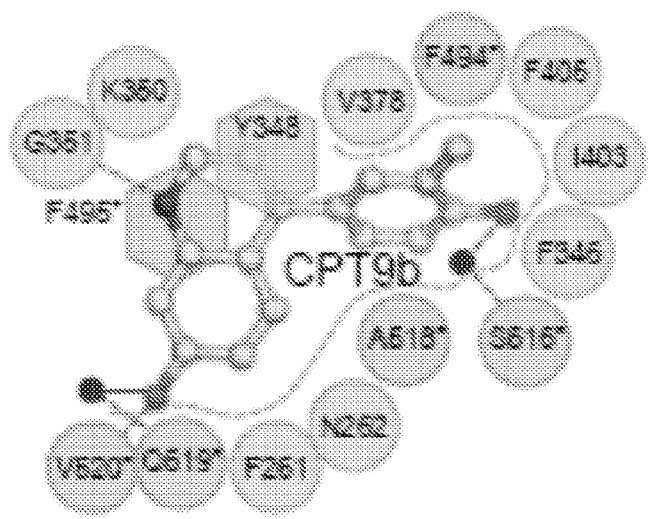
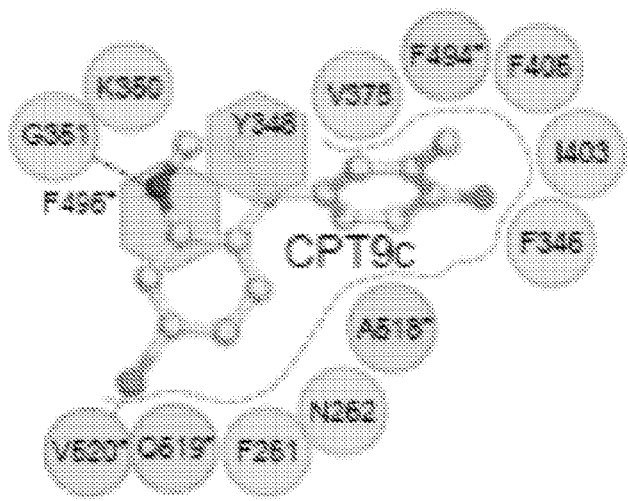

TOLL-LIKE RECEPTOR 8 (TLR8) SPECIFIC ANTAGONISTS AND METHODS OF MAKING AND USES THEREOF

CROSS REFERENCE TO RELATED APPLICATION

This application is a national stage application under 35 U.S.C. 371 of PCT Application No. PCT/US2018/058286 having an international filing date of Oct. 30, 2018, which designated the United States, which PCT application claimed the benefit of U.S. Application Ser. No. 62/579,015, filed Oct. 30, 2017, both of which are incorporated by reference in their entirety.#

GOVERNMENT INTEREST

This invention was made with government support under grant numbers R01 GM101279 and R01 GM103843 awarded by the National Institutes of Health. The government has certain rights in the invention.

TECHNICAL FIELD

This application relates to human Toll-like receptor (TLR) inhibitors, and methods for use in individuals having an autoimmune disease or an inflammatory disorder.

BACKGROUND

The innate immune response functions as the first line of defense against pathogenic microorganisms, and has also been implicated in autoimmune-mediated inflammatory diseases. This response is primarily triggered by Toll-like receptors (TLRs) which are activated by molecules of foreign origin, or in the case of immune-mediated inflammatory diseases, by molecules released by damaged host cells.

Toll-like receptors (TLRs) are type-I transmembrane proteins that recognize a variety of pathogen-associated molecular patterns from bacteria, viruses, and fungi. Human TLRs can elicit overlapping yet distinct biological responses due to differences in cellular expression and activation of downstream signal transduction pathways. The intracellular TLRs (including TLR3, TLR7, TLR8, and TLR9) are capable of detecting different classes of bacterial, viral, and endogenous nucleic acids. TLR3 recognizes dsRNA, TLR7 and 8 are activated by ssRNAs and imidazoquinoline derivatives, whereas TLR9 is activated by unmethylated ssDNA.

In humans, TLR7 and TLR8 are phylogenetically and structurally related, but differences in expression patterns have been identified between these two TLRs among human blood cells, preference for specific bases within the ssRNA ligand, and secondary structure prior to ligand binding. In an inactivated state, TLR8 exists as a pair of preformed dimers that change conformation upon ligand binding. Both self and foreign ssRNA within an endosome initiates TLR8-mediated signaling via the recruitment of MyD88, which in turn activates the downstream transcription factor NF-kappa-B, inducing the production of proinflammatory cytokines such as TNF-alpha, IL-1beta and IL-6. Despite the fact that TLR8 plays an important role in anti-viral responses, prolonged activation of TLR8 leads to the development of detrimental autoimmune disorders.

Activation of human TLR8 by endogenous ligands leads to different inflammatory diseases than those resulting from activation of TLR7. Based on gene polymorphism studies, TLR8 has been implicated in human inflammatory diseases, including RA, antiphospholipid syndrome, and IBD. Additionally, TLR8 signaling promotes RA both in human TLR8 transgenic mice and in human patients.

Thus, small molecules having inhibitory motifs for human TLR8 are desirable for use in human subjects.

SUMMARY

To identify specific TLR8 signaling inhibitors to use as chemical probes, and for potential therapeutic applications the inventors developed a cell-based high-throughput screening. Using this screen, they identified a series of potent TLR8 inhibitors. The most potent inhibited TLR8 signaling via a unique mechanism: stabilization of the preformed dimer of TLR8 protein. These inhibitors effectively inhibit TLR8-mediated functions in several types of cells (HEK-Blue, THP-1, and PBMC), and do not show any toxic effect on these cells. Identification of these inhibitors facilitates studies of the physiological roles played by TLR8 in autoimmune diseases. Additionally, these inhibitors provide treatments of several autoimmune and inflammatory diseases.

Thus, provided herein are human Toll-like receptor (TLR)-inhibitors and methods for use in individuals having an autoimmune disease or an inflammatory disorder. The TLR inhibitors of the present disclosure are molecules that specifically inhibit TLR8. This disclosure also provides for the use of these compounds in inhibiting a TLR8-dependent immune response in an individual. Moreover, the present disclosure provides compounds, and for the use of the compounds in inhibiting a TLR8-dependent immune response in an individual, wherein the compounds of this disclosure are compounds of the formula:

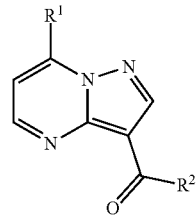

or a pharmaceutically acceptable salt thereof, wherein:

R1 is $C_{1-6}$ alkyl, $C_{3-8}$ cycloalkyl, $C_{2-4}$ alkenyl, $C_{2-4}$ alkynyl, $C_{1-4}$ alkoxy, or $C_{1-6}$ alkyl optionally substituted with hydroxy, mercapto, halide, $C_{1-6}$ alkyl, $C_{1-6}$ alkenyl, $C_{1-4}$ alkoxy, OR5, SR5, NR3R4, $CO_2R5$, OC(=O)R5, heteroaryl, or a combination thereof, or aryl or heteroaryl, optionally substituted with hydroxy, mercapto, nitro, halide, $C_{1-6}$ alkyl, $C_{1-6}$ alkenyl, $C_{1-4}$ alkoxy, OR5, SR5, NR3R4, $CO_2R5$, or a combination thereof;

R2 is NR3R4 or OR5;

R3, R4, and R5 are independently H, $C_{1-6}$ alkyl, $C_{3-8}$ cycloalkyl, $C_{2-4}$ alkenyl, aryl, heteroaryl, or $C_{1-6}$ alkyl substituted with hydroxy, mercapto, amino, sulfonic acid, carboxylic acid, halide, $C_{1-6}$ alkyl, $C_{1-6}$ alkenyl, $C_{1-4}$ alkoxy, heteroaryl, or a combination thereof, or R3 and R4 together form a heterocyclic ring optionally substituted with hydroxy or halide.

In exemplary aspects of this disclosure, these compounds include a compound of this structure, wherein:

R1 is 3-$CF_3$—$C_6H_4$—; 3-Me-$C_6H_4$—; 3-$CF_3$—$C_6H_4$—; 3-Me-$C_6H_4$—; 3-$CF_3$—$C_6H_4$—; 3-Me-$C_6H_4$—; 2-$CF_3$—

$C_6H_4$—; 4-$CF_3$—$C_6H_4$—; Phenyl-; 3-$NO_2$—$C_6H_4$—; 3-F—$C_6H_4$—; 3-$C_1$-$C_6H_4$—; 3,5-di$CF_3$—$C_6H_3$—; 2-OMe-$C_6H_4$—; 3-OMe-$C_6H_4$—; 3-Pyridyl; 3-Et-$C_6H_4$—; 3-$CF_3$—$C_6H_4$—; 3-$CF_3$—$C_6H_4$—; and, R2 is —$NH_2$, —NHMe, —$NEt_2$, —OEt, or —OH.

In one embodiment, the compounds include a compound of this structure, wherein R1 is 3-Me-$C_6H_4$— and R2 is —$NH_2$.

In related aspects, this disclosure provides a TLR8-inhibitor comprising the chemical formula:

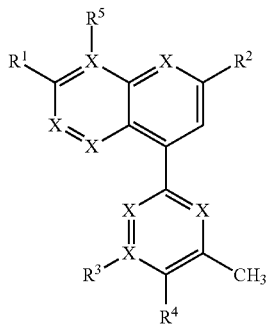

or a pharmaceutically acceptable salt thereof, wherein:

each X is independently nitrogen or carbon;

R1, R3, R4, and R5 are independently H, halide, $C_{1-6}$ alkyl, $C_{3-8}$ cycloalkyl, $C_{2-4}$ alkenyl, $C_{2-4}$ alkynyl, $C_{1-4}$ alkoxy, OR6; or $C_{1-6}$ alkyl optionally substituted with hydroxy, mercapto, halide, $C_{1-6}$ alkyl, $C_{1-6}$ alkenyl, $C_{1-4}$ alkoxy, OR6, SR6, NR7R8, $CO_2$R6, OC(=O)R6, heteroaryl, or a combination thereof; or aryl or heteroaryl, optionally substituted with hydroxy, mercapto, halide, $C_{1-6}$ alkyl, $C_{1-6}$ alkenyl, $C_{1-4}$ alkoxy, nitro, OR6, SR6, NR7R8, $CO_2$R6, or a combination thereof;

R2 is H, NR7R8, or OR6; and,

R6, R7, and R8 are independently H, $C_{1-6}$ alkyl, $C_{3-8}$ cycloalkyl, $C_{2-4}$ alkenyl, aryl, heteroaryl, benzyl; or $C_{1-6}$ alkyl substituted with hydroxy, mercapto, amino, sulfonic acid, carboxylic acid, halide, $C_{1-6}$ alkyl, $C_{1-6}$ alkenyl, $C_{1-4}$ alkoxy, heteroaryl, or a combination thereof; or R7 and R8 together form a heterocyclic ring optionally substituted with hydroxy or halide; or R1 and R5 together form a 5- or 6-membered unsubstituted, aromatic, heterocyclic ring comprising one or two heterocyclic atoms selected from nitrogen or carbon.

In one embodiment, the compounds include a compound of this structure, wherein X is nitrogen or carbon; R1 is —OMe; R2 is H; and R3 is H; R4 is OH; and R5 is H.

In one embodiment, the compounds include a compound of this structure, wherein X is nitrogen or carbon; R1 is —OH; R2 is H; and R3 is H; R4 is OH; and R5 is H.

Exemplary compounds of this formula include any one of the following compounds having the chemical structure:

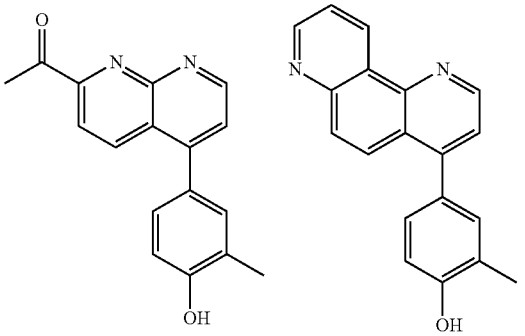

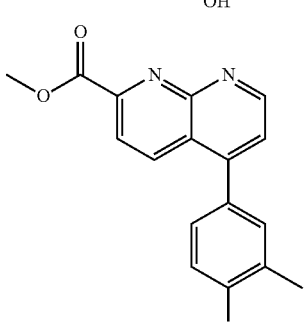

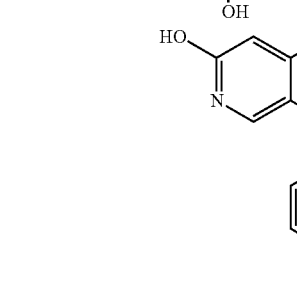

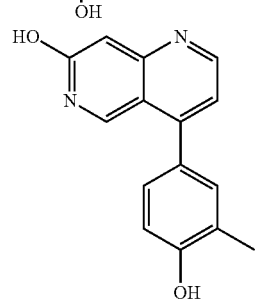

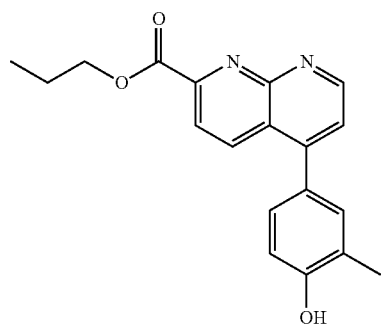

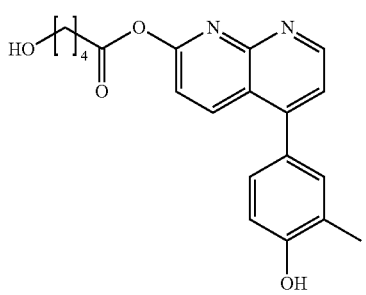

-continued
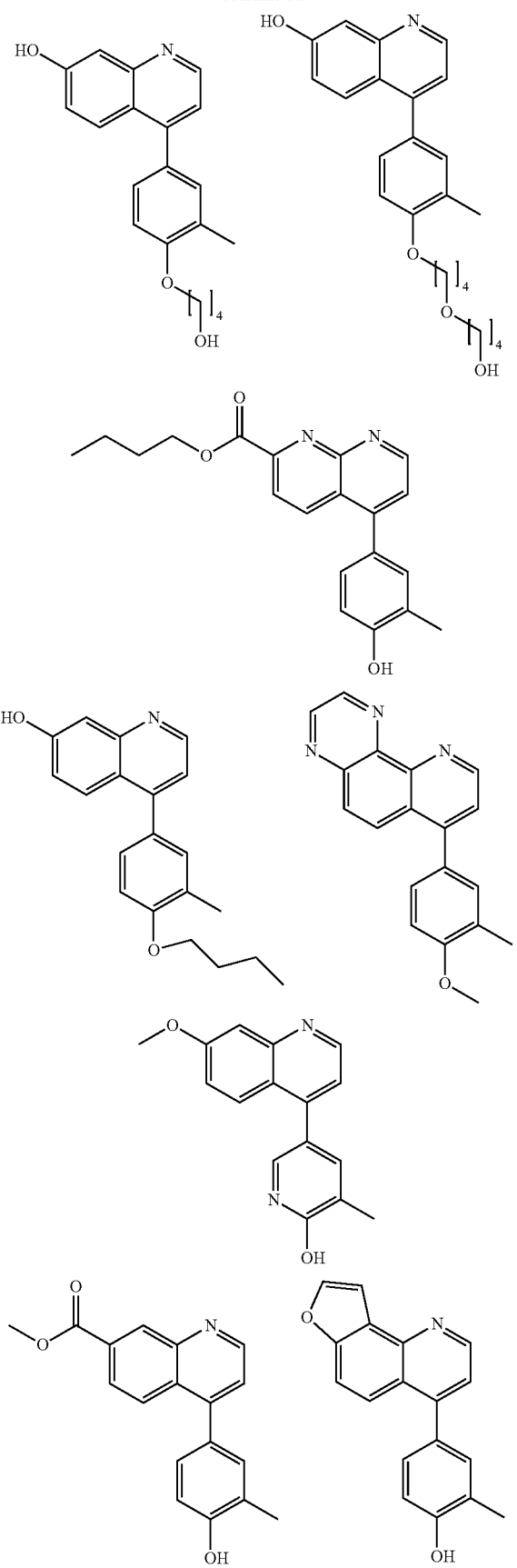
-continued
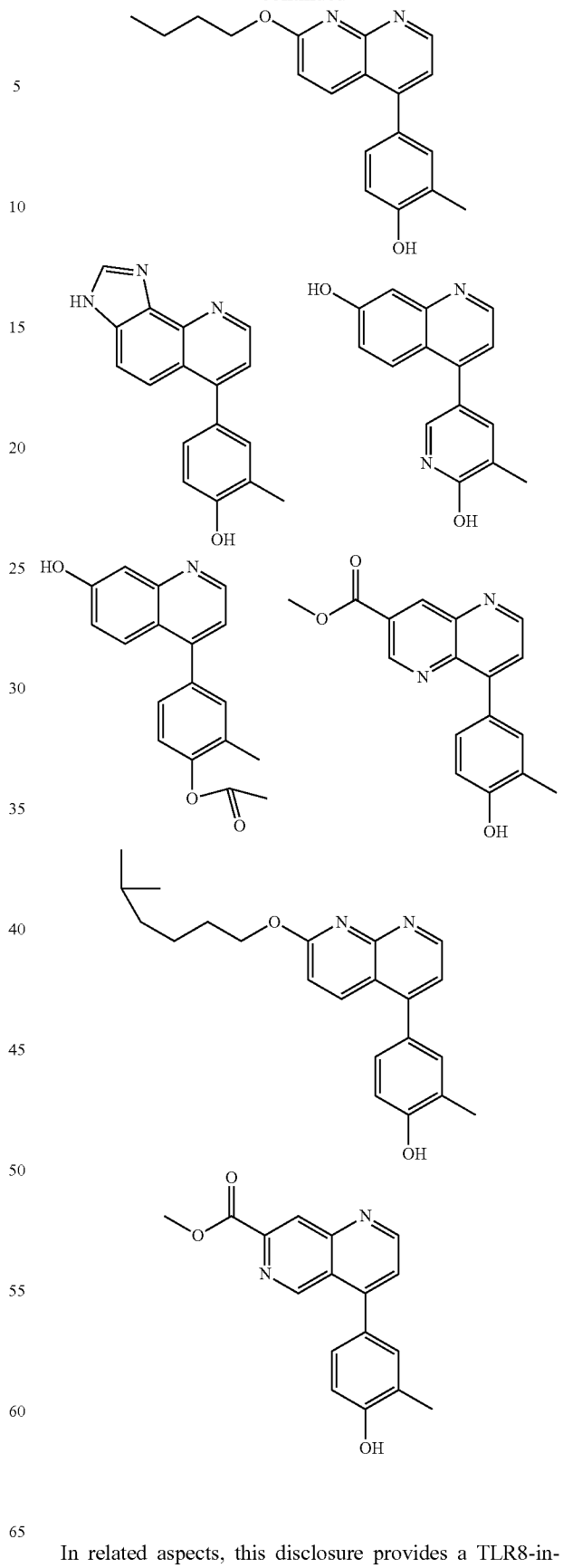
In related aspects, this disclosure provides a TLR8-inhibitor comprising the chemical formula:

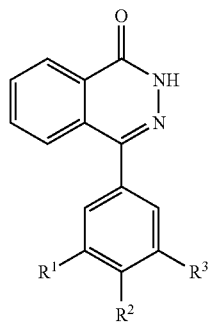

or a pharmaceutically acceptable salt thereof, wherein:

R1, R3, and R4 are independently H, $C_{1-6}$ alkyl, $C_{3-8}$ cycloalkyl, $C_{2-4}$ alkenyl, $C_{2-4}$ alkynyl, $C_{1-4}$ alkoxy, or $C_{1-6}$ alkyl optionally substituted with hydroxy, mercapto, halide, $C_{1-6}$ alkyl, $C_{1-6}$ alkenyl, $C_{1-4}$ alkoxy, OR5, SR5, NR3R4, $CO_2R5$, OC(=O)R5, heteroaryl, or a combination thereof, or aryl or heteroaryl, optionally substituted with hydroxy, mercapto, halide, $C_{1-6}$ alkyl, $C_{1-6}$ alkenyl, $C_{1-4}$ alkoxy, nitro, OR7, SR7, NR5R6, $CO_2R7$, or a combination thereof;

R2 is H, NR5R6, or OR7; and,

R5, R6, and R7 are independently H, $C_{1-6}$ alkyl, $C_{3-8}$ cycloalkyl, $C_{2-4}$ alkenyl, aryl, heteroaryl, or $C_{1-6}$ alkyl substituted with hydroxy, mercapto, amino, sulfonic acid, carboxylic acid, halide, $C_{1-6}$ alkyl, $C_{1-6}$ alkenyl, $C_{1-4}$ alkoxy, heteroaryl, or a combination thereof, or R5 and R6 together form a heterocyclic ring optionally substituted with hydroxy or halide.

In exemplary aspects of this disclosure, these compounds include a compound of this structure, wherein:

R1 is H;

R2 is H or —OH;

R3 is H or —$CH_3$.

The present disclosure also provides methods of inhibiting an immune response in an individual, by administering to the individual a pharmaceutical composition comprising a compound of this disclosure in an amount effective to inhibit the immune response in the individual. The immune response may be associated with an autoimmune disease. Inhibiting the immune response may ameliorate one or more symptoms of the autoimmune disease. The autoimmune disease may be selected from the group consisting of rheumatoid arthritis, pancreatitis, mixed tissue connective disease, systemic lupus erythematosus, antiphospholipid syndrome, irritable bowel disease, type I diabetes mellitus, and Sjogren's syndrome. The autoimmune disease may be associated with RNA-containing immune complexes (or inflammation from RNA bound to peptides, such as cationic peptides). The immune response may be associated with an inflammatory disorder, and inhibiting the immune response may ameliorate one or more symptoms of the inflammatory disorder. The inflammatory disorder may be associated with elevated expression of TLR8 (or aberrant TLR8 signaling). Inhibiting the immune response may treat the autoimmune disease or the inflammatory disorder. Alternatively or additionally, inhibiting the immune response may prevent or delay development of the autoimmune disease or the inflammatory disorder. In these methods, the individual treated may be a human.

The present disclosure also provides compound of any of the preceding paragraphs for preparation of a medicament for treating or preventing an autoimmune disease or an inflammatory disorder. The medicament may comprise an effective amount of the compound for ameliorating one or more symptoms of the autoimmune disease. The autoimmune disease may be selected from the group consisting of rheumatoid arthritis, pancreatitis, mixed tissue connective disease, systemic lupus erythematosus, antiphospholipid syndrome, irritable bowel disease, type I diabetes mellitus, and Sjogren's syndrome. The autoimmune disease may be associated with RNA-containing immune complexes (or inflammation from RNA bound to peptides such as cationic peptides). The immune response may be associated with an inflammatory disorder. The medicament may comprise an effective amount of one or more compounds of this disclosure for ameliorating one or more symptoms of the inflammatory disorder. The inflammatory disorder may be associated with elevated expression of TLR8 (or aberrant TLR8 signaling). The medicament may treat the autoimmune disease or the inflammatory disorder. Alternatively or additionally, the medicament prevents or delays development of the autoimmune disease or the inflammatory disorder. The individual having the autoimmune disease or the inflammatory disorder may be a human.

This Summary is neither intended nor should it be construed as being representative of the full extent and scope of the present invention. Moreover, references made herein to "the present disclosure," or "this disclosure" or aspects thereof, should be understood to mean certain embodiments of the present disclosure and should not necessarily be construed as limiting all embodiments to a particular description. The present invention is set forth in various levels of detail in this Summary as well as in the attached drawings and the Detailed Description and no limitation as to the scope of the invention is intended by either the inclusion or non-inclusion of elements, components, etc. in this Summary. Additional aspects of the invention will become more readily apparent from the Detailed Description, particularly when taken together with the figures.

BRIEF DESCRIPTION OF FIGURES

FIG. 1), was employed as the positive control. Results shown as mean±s.e.m.

FIG. 4A shows the chemical structures of compounds CU-CPT8m and 4a (negative control), concentration-response curve (black) and dose-dependent cytotoxicity (red) of CU-CPT8m in HEK-Blue TLR8 cell line. Data were collected 24 h after compound treatment and normalized to a DMSO control (mean±SD; n=3). FIG. 4B shows the results of the specificity test for CU-CPT8m (1 μM) with TLR-specific agonists used to selectively activate different HEK-Blue TLR-overexpressing cells: 1. TLR1/2: 100 ng/mL Pam3CSK4; 2. TLR2/6: 100 ng/mL Pam2CSK3; 3. TLR3: 5 μg/mL poly(I:C); 4. TLR4: 20 ng/mL LPS; 5.

TLR5: 50 ng/mL Flagellin; 6. TLR7: 1 μg/mL R848; 7. TLR8: 1 μg/mL R848; 8. TLR9: 0.15 μM ODN2006 were used to selectively activate respective TLRs in the presence or absence of 1 μM CU-CPT8m (mean SD; n=3). FIG. 4C shows the ITC analysis of TLR8 titrated with CU-CPT8m. FIG. 4D shows the TNF-α and IL-8 mRNA levels in R848 treated HEK-Blue TLR8 cells in the presence and absence of 1 μM CU-CPT8m or the negative control, 4a (10 μM). Data shown is the average quantification of two biological replicates, each in technical duplicate. FIG. 4E shows the dose-dependent response of CU-CPT8m on TLR8-mediated TNF-α production in THP-1 cells with indicated concentration of CU-CPT8m or 4a (10 μM). Data present the mean values (SD) of 3 biological replicates, each performed in triplicate. FIG. 4F shows a dose-dependent response of CU-CPT8m or 4a (50 μM) on TLR8-mediated TNF-α production in PBMC cells induced by 1 μg/mL R848. Data present the mean values (±SD) of 3 biological replicates, each performed in triplicate.

FIGS. 7A and 7B shows the inhibitory effects and cell viability results of CU-CPT9a (FIG. 7A) and CU-CPT9b (FIG. 7B) in HEK-Blue TLR8 cells. FIGS. 7C and 7D shows that CU-CPT9a (FIG. 7C; 80 nM) and CU-CPT9b (FIG. 7D; 80 nM) inhibited both ssRNA40 (2.5 μg/mL) and R848 (1 μg/mL)-induced TLR8 activation in HEK-Blue TLR8 cells. Results are shown as mean±s.e.m.

FIG. 8A shows representative western blot bands for IRAK-4, TRAF-3, p65, TRIF and IRF3. Immunoblot analyses of THP-1 cells treated with R848 (1 μg/mL) with or without CU-CPT9a (0, 5, 50, 500 nM) for 2 h. These data show an elevation and inhibition of phosphorylated IRAK4 (p-IRAK4), TRAF3 and nuclear expression of NF-κB/p65. The expression levels of IRAK4, TRIF, IRF3, NF-κB/p65 cytoplasmic components showed no change in the response to R848 and CU-CPT9a treatment. FIG. 8B shows quantitative data analyses. The p65/Lamin A/C, TRAF3/GADPH, p-IRAK4/IRAK4 and TRIF/GADPH ratios were calculated after densitometric analysis of specific signals using image J software. B-Actin, and GAPDH were used as the internal controls for cytoplasmic fractions. Lamin A/C was used for nuclear fractions. Data are representative of multiple independent protein preparations (n>3) showing the same trends. *P<0.05; P<0.01; *P<0.001.

FIG. 9A shows the chemical structure of CU-CPT9a and CU-CPT9b. FIG. 9B shows the close-up view of antagonist binding site and its schematic representation of TLR8/CU-CPT9b.

FIG. 11A shows the effect of CU-CPT8m treatment on the production of IL-1β (left) and TNF-α (right) in synovial cells harvested from OA patients. The graph represents percent change 24 h after inhibitor treatment as compared to untreated cells from the same patient. Each data point represents an independent biological sample read. Center lines indicate means, and whiskers indicate s.e.m. (n=3 independent biological samples for IL-1β, and n=4 independent biological samples for TNF-α in technical duplicates, P-values were determined using one-way ANOVA, *P<0.05, **P<0.01). FIG. 11B shows the effects of CU-CPT8m (left) and CU-CPT9a (right) treatment on the production of TNF-α in PBMC cells harvested from RA patients. Each data point represents an independent biological sample read. Center lines indicate means, and whiskers indicate s.e.m. (n=4 independent biological samples for CU-CPT8m, and n=3 independent biological samples for CU-CPT9a in technical duplicates, P-values were determined using one-way ANOVA, *P<0.01, ***P<0.001).

FIG. 16A shows the results of specificity tests of compounds CU-CPT9a (top) and 9b (bottom) in HEK-Blue cells overexpressing individual TLRs. For HEK-Blue hTLR1/2, hTLR2/6, hTLR3, hTLR4, hTLR5, hTLR7/8, and hTLR9 cells, Pam3CSK4 (100 ng/mL), Pam2CSK4 (100 ng/mL), poly(I:C) (5 μg/mL), LPS (lipopolysaccharide) (20 ng/mL), flagellin (50 ng/mL), R848 (1 μg/mL), ODN2006 (0.15 μM) were used as TLR-specific agonists, respectively. FIG. 16B shows the results of specificity tests of compounds CU-CPT9a (top) and 9b (bottom) in PBMCs (B cells, monocytes, etc.) isolated from human donors. The entire PBMC population was used to assess antagonist activity against TLR2, 4, and 5. Isolated B cells were used to assess antagonist activity against TLR7 and 9, and isolated monocytes were used for TLR8. (data are mean SD; n=3 independent experiments).

FIG. 17 provides schematic representations showing the interactions within the binding pockets of TLR8/CU-CPT9a (top), TLR8/CU-CPT9b (middle) and TLR8/CU-CPT9c (bottom) complexes.

DETAILED DESCRIPTION

Figure 1A:
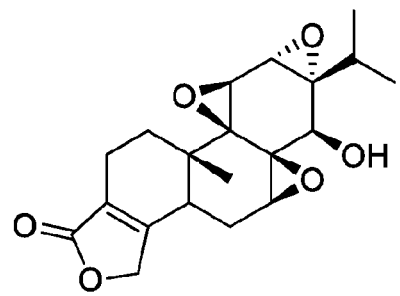
FIG. 1 shows the chemical structure of triptolide.

This disclosure provides compounds useful for inhibiting TLR8 and TLR8-related immune response(s). These compounds selectively inhibit TLR8 with minimal or no effects on other TLR protein family members, including TLR7 or TLR9, and with minimal or no adverse effects on the cells or tissues contacted with the compounds of this disclosure. Provided herein are Toll-like receptor 8 (TLR8)-inhibitors and methods for use in inhibiting a TLR8-dependent immune response in an individual. The individual may have an autoimmune disease or an inflammatory disorder. The TLR8 inhibitors of this disclosure are compounds comprising an inhibitory motif for TLR8.

General Techniques

Methods of the present disclosure employ, unless otherwise indicated, conventional techniques of molecular biology (including recombinant techniques), microbiology, cell biology, chemistry, biochemistry and immunology, which are within the skill of the art. Such techniques are explained fully in the literature, such as, Molecular Cloning: A Laboratory Manual, second edition (Sambrook et al., 1989); Oligonucleotide Synthesis (Gait, ed., 1984); Animal Cell Culture (Freshney, ed., 1987); Handbook of Experimental Immunology (Weir & Blackwell, eds.); Gene Transfer Vectors for Mammalian Cells (Miller & Calos, eds., 1987); Current Protocols in Molecular Biology (Ausubel et al., eds., 1987); PCR: The Polymerase Chain Reaction (Mullis et al., eds., 1994); Current Protocols in Immunology (Coligan et al., eds., 1991); The Immunoassay Handbook (Wild, ed., Stockton Press NY, 1994); Bioconjugate Techniques (Hermanson, ed., Academic Press, 1996); and Methods of Immunological Analysis (Masseyeff, Albert, and Staines, eds., Weinheim: VCH Verlags gesellschaft mbH, 1993).

Definitions

The term "nucleic acid," includes single-stranded DNA (ssDNA), double-stranded DNA (dsDNA), single-stranded RNA (ssRNA) and double-stranded RNA (dsRNA), modified nucleotides, and polynucleosides, or combinations thereof.

The term "agonist" is used in the broadest sense and includes any molecule that activates signaling through a receptor. For instance, a TLR8 agonist binds a TLR8 receptor and activates a TLR8-signaling pathway.

The term "antagonist" is used in the broadest sense, and includes any molecule that blocks a biological activity of an agonist. For instance, a TLR8 antagonist suppresses a TLR8-signaling pathway.

The effect of a compound on a TLR8-dependent immune response can be determined in vitro by measuring a response of an immune cell (e.g., leukocytes such as lymphocytes, monocytes, and dendritic cells) contacted with a TLR8 agonist in the presence and absence of the compound. As referred to herein, a TLR8 inhibitor is a compound that inhibits a TLR-dependent immune response at an IC50 (half maximal inhibitory concentration) of less than 500 nM. Compounds with an IC50 of less than 200 nM are considered to be highly active TLR inhibitors. Compounds with an IC50 of from 201-500 nM are considered to be moderately active TLR inhibitors. Compounds with an IC50 of greater than 500 mM are considered to be essentially inactive (e.g., not a TLR inhibitor).

Examples of measurable immune responses include, but are not limited to, antigen-specific antibody production, cytokine secretion, lymphocyte activation and lymphocyte proliferation.

"Stimulation" of a response or parameter includes eliciting and/or enhancing that response or parameter when compared to otherwise same conditions except for a parameter of interest, or alternatively, as compared to another condition (e.g., increase in TLR-signaling in the presence of a TLR agonist as compared to the absence of the TLR agonist). For example, "stimulation" of an immune response means an increase in the response, which can arise from eliciting and/or enhancement of a response. Similarly, "stimulation" of production of a cytokine (such as IL-1alpha., IL-1beta, IL-6, and/or TNF-alpha) or "stimulation" of cell type (such as CTLs) means an increase in the amount or level of cytokine or cell type.

"Suppression" or "inhibition" of a response or parameter includes decreasing that response or parameter when compared to otherwise same conditions except for a parameter of interest, or alternatively, as compared to another condition (e.g., increase in TLR-signaling in the presence of a TLR agonist and a TLR antagonist as compared to the presence of the TLR agonist in the absence of the TLR antagonist).

The term "cells," as used herein, is understood to refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein.

The term "individual" refers to a mammal, including humans. An individual includes, but is not limited to, human, bovine, equine, feline, canine, rodent, or primate subjects.

Administration "in combination with" one or more further therapeutic agents includes simultaneous (concurrent) and consecutive administration in any order.

"Chronic" administration refers to administration of the agent(s) in a continuous mode as opposed to an acute mode, so as to maintain the initial therapeutic effect (activity) for an extended period of time. "Intermittent" administration refers to treatment that is not consecutively and/or continuously done without interruption, but rather is cyclic in nature.

An "effective amount" of an agent disclosed herein is an amount sufficient to carry out a specifically stated purpose. An "effective amount" may be determined empirically and in a routine manner, in relation to the stated purpose.

The term "therapeutically effective amount" refers to an amount of an agent (e.g., TLR inhibitor) effective to "treat" a disease or disorder in a subject (e.g., a mammal such as a human). In the case of autoimmune disease, the therapeutically effective amount of the agent reduces a sign or symptom of the autoimmune disease. For instance, in connection with treatment of a rheumatoid arthritis, a therapeutically effect amount of an agent (e.g., TLR8 inhibitor) reduces a sign or symptom of rheumatoid arthritis in a patient, which may also reduce the rate of damage to bone and cartilage.

The terms "treating" or "treatment" of a disease refer to executing a protocol, which may include administering one or more drugs to an individual (human or otherwise), in an effort to alleviate signs or symptoms of the disease. Thus, "treating" or "treatment" does not require complete alleviation of signs or symptoms, does not require a cure, and specifically includes protocols that have only a marginal effect on the individual.

As used herein, and as well-understood in the art, "treatment" is an approach for obtaining beneficial or desired results, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

It is understood that aspects described herein as "comprising" include "consisting" and/or "consisting essentially of" aspects and embodiments.

Compositions

Compounds comprising an inhibitory motif for TLR8 (TLR8 inhibitors) are provided herein. Also provided are TLR8 inhibitors for use in any of the methods described herein. Each compound of this disclosure comprises at least one inhibitory motif.

This disclosure also provides methods of making the compounds comprising an inhibitory motif for TLR8. The methods may be any of those described herein. For example, the method could be synthesizing the TLR inhibitors (for example, using solid state synthesis) and may further comprise any purification step(s). Methods of purification are known in the art.

TLR inhibitor Complexes

TLR inhibitors of this disclosure can be directly administered to the individual or they can be administered in a composition or complex to enhance TLR inhibitor delivery to cells and/or uptake by cells. Compositions or complexes can also be used to enhance co-delivery of two of more different TLR inhibitors to a cell. a mixture of TLR inhibitors may be complexed so as to deliver at least one TLR inhibitor.

Such delivery compositions or complexes include, but are not limited to, encapsulating complexes and colloidal dispersion systems as described herein and known in the art. Examples of such delivery compositions include oil-in-water emulsions, micelles, and liposomes. Delivery compositions or complexes also include TLR inhibitors linked to a linker molecule, a platform molecule, a nanoparticle or a microparticle, as described herein. Such linkages include both covalent and non-covalent linkages. The TLR inhibitor may be conjugated with a linker molecule in a variety of ways, including covalent and/or non-covalent interactions.

A TLR inhibitor may be proximately associated in other ways. For example, a TLR inhibitor may be proximately associated by encapsulation or proximately associated by linkage to a platform molecule. A "platform molecule" (also termed "platform") is a molecule containing sites which allow for attachment of the TLR inhibitor. a TLR inhibitor may be proximately associated by adsorption onto a surface, preferably a carrier particle. The methods described herein may employ an encapsulating agent in association with the TLR inhibitor. Preferably, the composition comprising a TLR8 inhibitor and encapsulating agent is in the form of adjuvant oil-in-water emulsions, microparticles and/or liposomes. Colloidal dispersion systems, such as microspheres, beads, macromolecular complexes, nanocapsules and lipid-based system, such as oil-in-water emulsions, micelles, mixed micelles and liposomes can provide effective encapsulation of TLR inhibitors-containing compositions of this disclosure.

The encapsulation composition further comprises any of a wide variety of components. These include, but are not limited to, alum, lipids, phospholipids, polyethylene glycol (PEG) and other polymers, such as polypeptides, glycopeptides, and polysaccharides.

Lipid bilayers, such as liposomes, containing tissue or cellular targeting components may also be used in the TLR-inhibitor compositions of this disclosure. Such targeting components enhance accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art. The liposomes can be targeted to any cell type toward which a therapeutic treatment is to be directed, e.g., a cell type which can regulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

Pharmaceutical Formulations

Pharmaceutical formulations comprising a TLR inhibitor as described herein are also provided. The pharmaceutical formulations comprising the TLR inhibitor may be administered in an effective amount of a composition to an individual to achieve a specific outcome. The pharmaceutical formulations may routinely contain pharmaceutically acceptable concentrations of salt, buffering agents, preservatives, compatible carriers, adjuvants, and optionally other therapeutic ingredients. The pharmaceutical formulations comprise at least one TLR8 inhibitor of this disclosure.

Pharmaceutical formulations may include, for example, aqueous or saline solutions for injection or inhalation, or may be microencapsulated, coated onto microscopic gold particles, contained in liposomes, nebulized, aerosols, pellets for implantation into the skin, or dried onto a sharp object to be scratched into the skin. Pharmaceutical formulations also include granules, powders, tablets, coated tablets, (micro)capsules, suppositories, syrups, emulsions, suspensions, creams, drops or preparations with protracted release of active compounds, e.g., in whose preparation excipients and additives and/or auxiliaries such as disintegrants, binders, coating agents, swelling agents, lubricants, flavorings, sweeteners or solubilizers are customarily used as described above. The pharmaceutical formulations are suitable for use in a variety of drug delivery systems.

The pharmaceutical formulation comprising the TLR8 inhibitor(s) may further comprise a pharmaceutically acceptable carrier, excipient, or stabilizer. Pharmaceutically acceptable carriers, excipients, or stabilizers are described herein and well known in the art (see, e.g., Remington: The Science and Practice of Pharmacy, 20th edition, Mack Publishing, 2000). Examples of physiologically acceptable carriers, excipients, or stabilizers include, but are not limited to, buffers such as phosphate, citrate, and other organic acids; antioxidants including ascorbic acid; low molecular weight polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

The pharmaceutical formulations comprising the TLR inhibitor may be suitable for parenteral administration. Among the acceptable vehicles and solvents are water, Ringer's solution, phosphate buffered saline, and isotonic sodium chloride solution. In addition, sterile, fixed oils are conventionally employed as a solvent or suspending medium. For this purpose, any bland fixed mineral or non-mineral oil may be employed including synthetic mono- or diglycerides. In addition, fatty acids such as oleic acid find use in the preparation of injectables. The pharmaceutical formulations comprising the TLR inhibitor may also be suitable for subcutaneous, intramuscular, intraperitoneal, or intravenous delivery.

The pharmaceutical formulation comprising the TLR inhibitor may be a time-release, delayed release, or sustained release pharmaceutical formulation. Sustained-release pharmaceutical formulations include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Non-polymer pharmaceutical formulation can include: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like.

A pharmaceutical formulation comprising the TLR inhibitor may be suitable for topical application including, but not limited to, physiologically acceptable ointments, creams, rinses, emulsions, lotions, solutions, pastes, and gels.

The pharmaceutical formulations comprising the TLR inhibitor may be a pharmaceutical formulation formulated for transdermal administration. Transdermal administration is accomplished by application of e.g., a cream, rinse, or gel.

The pharmaceutical formulation may be a pharmaceutical formulation formulated for gastrointestinal routes of administration. Pharmaceutical formulations for gastrointestinal routes may comprise pharmaceutically acceptable powders, pills or liquids for ingestion and suppositories for rectal administration.

The pharmaceutical formulation may be a pharmaceutical formulation formulated for naso-pharyngeal and pulmonary administration. Pharmaceutical formulations suitable for naso-pharyngeal and pulmonary administration include, but not limited to, liquid suspensions for forming aerosols as well as powder forms for dry powder inhalation delivery systems are provided.

Methods of Use Provided herein are methods of inhibiting an immune response in an individual comprising administering to the individual an effective amount of a TLR8 inhibitor of this disclosure. The TLR inhibitor inhibits a TLR8-dependent immune response. The individual may be a human patient.

Methods of immunoregulation are provided by the present disclosure and include those that suppress and/or inhibit an immune response, including, but not limited to, an immune response. The present disclosure also provides methods for ameliorating symptoms associated with unwanted immune activation, including, but not limited to, symptoms associated with autoimmunity. Immune suppression and/or inhibition according to the methods described herein may be practiced on individuals including those suffering from a disorder associated with an unwanted activation of an immune response. The present disclosure also provides methods for inhibiting a TLR8-induced response (e.g., in vitro or in vivo). In some variations, the cell is contacted with the TLR8 inhibitor in an amount effective to inhibit a response from the cell that contributes to an immune response.

Inhibition of TLR8 may be useful for treating and/or preventing a variety of diseases or disorders that are responsive to cytokines. Conditions for which TLR8 inhibitors may be used as treatments include, but are not limited to autoimmune diseases and inflammatory disorders. Provided herein are methods of treating or preventing a disease or disorder in an individual comprising administering to the individual an effective amount of an inhibitor of TLR8. Further, provided are methods for ameliorating symptoms associated with a disease or disorder comprising administering an effective amount of an inhibitor of TLR8 to an individual having the disease or disorder. Methods are also provided herein for preventing or delaying development of a disease or a disorder, comprising administering an effective amount of an inhibitor of TLR8 to an individual having the disease or the disorder.

Provided herein are methods of inhibiting an immune response in an individual, the method comprising administering to the individual at least one TLR8 inhibitor of this disclosure in an amount effective to inhibit the immune response in the individual. In some variations, the immune response is associated with an autoimmune disease. In further aspects, wherein inhibiting the immune response ameliorates one or more symptoms of the autoimmune disease. In still further aspects, wherein inhibiting the immune response treats the autoimmune disease. In yet further aspects, wherein inhibiting the immune response prevents or delays development of the autoimmune disease.

In some variations, the TLR8 inhibitor inhibits a TLR8-dependent immune response. In some aspects, at least one TLR8 inhibitor is administered in an amount effective to inhibit an immune response in the individual.

Provided herein are also methods of treating or preventing an autoimmune disease in an individual, comprising administering to the individual an effective amount of a TLR8 inhibitor. In some aspects, the autoimmune disease is characterized by joint pain, antinuclear antibody positivity, malar rash, or discoid rash. In some aspects, the autoimmune disease is associated with the skin, muscle tissue, and/or connective tissue, but the autoimmune disease may not always be evidenced in the individual by skin, muscle tissue, and/or connective tissue symptoms. The autoimmune disease may be systemic. Autoimmune diseases include, without limitation, rheumatoid arthritis (RA), autoimmune pancreatitis (AIP), systemic lupus erythematosus (SLE), type I diabetes mellitus, multiple sclerosis (MS), antiphospholipid syndrome (APS), sclerosing cholangitis, systemic onset arthritis, irritable bowel disease (IBD), scleroderma, Sjogren's disease, vitiligo, polymyositis, pemphigus vulgaris, pemphigus foliaceus, inflammatory bowel disease including Crohn's disease and ulcerative colitis, autoimmune hepatitis, hypopituitarism, graft-versus-host disease (GvHD), autoimmune skin diseases, uveitis, pernicious anemia, and hypoparathyroidism. Autoimmune diseases may also include, without limitation, polyangiitis overlap syndrome, Kawasaki's disease, sarcoidosis, glomerulonephritis, and cryopathies. These conditions are well known in the medical arts and are described, for example, in Harrison's Principles of Internal Medicine, 14th ed., Fauci et al., eds., New York: McGraw-Hill, 1998. In some aspects, the autoimmune disease is selected from the group consisting of arthritis, pancreatitis, mixed connective tissue disease (MCTD), lupus, antiphospholipid syndrome (APS), systemic onset arthritis, and irritable bowel syndrome. In other aspects, the autoimmune disease is selected from the group consisting of systemic lupus erythematosus (SLE), rheumatoid arthritis, autoimmune skin disease, and multiple sclerosis. In other aspects, the autoimmune disease is selected from the group consisting of pancreatitis, glomerulonephritis, pyelitis, sclerosing cholangitis, and type I diabetes. In some aspects, the autoimmune disease is rheumatoid arthritis. In some aspects, the autoimmune disease is autoimmune pancreatitis (AIP). In some aspects, the autoimmune disease is glomerulonephritis. In some aspects, the autoimmune disease is pyelitis. In some aspects, the autoimmune disease is sclerosing cholangitis. In some aspects the autoimmune disorder is psoriasis. In some aspects, the autoimmune disease is a rheumatoid disease or disorder. In some aspects, the rheumatoid disease or disorder is rheumatoid arthritis. In some aspects, the disease is diabetes and/or diabetic-related disease or disorder. In some aspects, wherein the autoimmune disease is associated with RNA-containing immune complexes. In some aspects, the autoimmune disease is Sjogren's disease.

Provided herein are methods of inhibiting an immune response in an individual, the method comprising administering to the individual at least one TLR inhibitor as disclosed herein in an amount effective to inhibit the immune response in the individual. In some variations, the immune response is associated with an inflammatory disorder. As used herein, the term "inflammatory disorder" encompasses autoimmune diseases, as well as inflammatory conditions without a known autoimmune component (e.g., artherosclerosis, asthma, etc.). In further aspects, inhibiting the immune response ameliorates one or more symptoms of the inflammatory disorder. In still further aspects, inhibiting the immune response treats the inflammatory disorder. In yet further aspects, inhibiting the immune response prevents or delays development of the inflammatory disorder. In some aspects, the inflammatory disorder is selected from the group consisting of non-rheumatoid arthritis, kidney fibrosis, and liver fibrosis. In some aspects, the inflammatory disorder is an interface dermatitis. In some further aspects, the interface dermatitis is selected from the group consisting of lichen planus, lichenoid eruption, lichen planus-like keratosis, lichen striatus, keratosis lichenoides chronica, erythema multiforme, fixed drug eruption, pityriasis lichenoides, phototoxic dermatitis, radiation dermatitis, viral exanthems, dermatomyositis, secondary syphilis, lichen sclerosus et atrophicus, mycosis fungoides, bullous pemphigoid, lichen aureus, porokeratosis, acrodermatitis chronicus atrophicans, and regressing melanoma. In some aspects, the inflammatory condition is a skin disorder such as atopic dermatitis (eczema). In some aspects, the inflammatory disorder is a sterile inflammatory condition such as drug-induced liver and/or pancreas inflammation. In some further aspects, the inflammatory disease is an inflammatory liver disorder. In some other further aspects, the inflammatory disease is an inflammatory pancreatic disorder.

Provided herein are methods of inhibiting an immune response in an individual, the method comprising administering to the individual at least one TLR inhibitor as disclosed herein in an amount effective to inhibit the immune response in the individual. In some variations, the immune response is associated with chronic pathogen stimulation. In some variations, the immune response is associated with infection by HIV. In further aspects, wherein inhibiting the immune response ameliorates one or more symptoms of the viral disease or disorder resulting from infection by HIV. In still further aspects, wherein inhibiting the immune response treats the viral disease or disorder resulting from infection by HIV. In yet further aspects, wherein inhibiting the immune response prevents or delays development of the viral disease or disorder resulting from infection by HIV. Other variations provided herein relate to immunoinhibitory therapy of individuals having been exposed to or infected with HIV. Administration of a TLR inhibitor to an individual having been exposed to or infected with HIV results in suppression of HIV induced cytokine production. In some aspects, at least one TLR inhibitor is administered in an amount effective to suppress HIV induced cytokine production in an individual exposed to or infected with a HIV.

Provided herein are methods for inhibiting a TLR8-dependent immune response in an individual, the method comprising administering to the individual a TLR inhibitor in an amount effective to inhibit the immune response in the individual. In some variations, the immune response is associated with an autoimmune disease. In some aspects, the autoimmune disease is rheumatoid arthritis. In some aspects, the TLR inhibitor is effective in suppressing one or more symptoms of rheumatoid arthritis. In some aspects, the autoimmune disease is multiple sclerosis. In some aspects, the TLR inhibitor is effective in suppressing one or more symptoms of multiple sclerosis. In some aspects, the autoimmune disease is lupus. In some aspects, the TLR inhibitor is effective in suppressing one or more symptoms of lupus. In some aspects, the autoimmune disease is pancreatitis. In some aspects, the TLR inhibitor is effective in suppressing one or more symptoms of pancreatitis. In some aspects, the autoimmune disease is diabetes. In some aspects, the TLR inhibitor is effective in suppressing one or more symptoms of diabetes. In some aspects, the disease is Sjogren's disease.

In some aspects, the TLR inhibitor is effective in suppressing one or more symptoms of Sjogren's disease. In some variations, the immune response is associated with an inflammatory disorder. In some aspects, the TLR inhibitor is effective in suppressing one or more symptoms of an inflammatory disorder. In some variations, the immune response is associated with chronic pathogen stimulation. In some aspects, the TLR inhibitor is effective in suppressing one or more symptoms of chronic pathogen stimulation. In some variations, the immune response is associated with viral disease resulting from infection with HIV. In some aspects, the TLR inhibitor is effective in suppressing one or more symptoms of viral disease resulting from infection with HIV. In any variation, the TLR inhibitor is a compound comprising an inhibitory motif for TLR8.

The methods herein provide prophylactic treatment, therapeutic treatment, or both. Prophylactic treatment as used herein refers to treatment that is initiated prior to observation of symptoms and/or a suspected exposure to a causative agent of the condition (e.g., a pathogen or carcinogen). Generally, prophylactic treatment may reduce (a) the likelihood that an individual receiving the treatment develops the condition and/or (b) the duration and/or severity of symptoms in the event the subject develops the condition. As used herein, therapeutic treatment refers to treatment initiated after observation of symptoms and/or a suspected exposure to a causative agent of the condition. Generally, therapeutic treatment may reduce the severity and/or duration of symptoms associated with the condition.

As demonstrated herein, particular TLR inhibitors comprising an inhibitory motif for one or more of TLR8 do not inhibit TLR7-dependent cell responses. TLR8 inhibitors of this disclosure may not inhibit TLR1-dependent, TLR2-dependent, TLR3-dependent, TLR4-dependent, TLR5-dependent, TLR6-dependent, TLR7-dependent, TLR9-dependent, TLR10-dependent, TLR11-dependent, TLR12-dependent and/or TLR13-dependent cell responses. TLR8 inhibitors comprising an inhibitory motif for TLR8, as described herein, may inhibit or suppress a measurable immune response as determined in vitro, in vivo, and/or ex vivo.

As described herein, some TLR inhibitors with newly defined TLR8 inhibitory motifs are particularly effective in suppressing TLR8 dependent cell responses. As described herein, some TLR inhibitors are particularly effective in suppressing TLR8 dependent cell responses.

In the methods involving administration of a TLR8 inhibitor of this disclosure to an individual (e.g., methods of inhibiting an immune response, treating or preventing an autoimmune disease or inflammatory disorder, etc.) the TLR inhibitor has a therapeutically acceptable safety profile. The TLR8 inhibitor may, for example, have a therapeutically acceptable histological profile including an acceptably low, if any, toxicity of the liver, kidney, pancreas, or other organs. On occasion, compounds have been associated with toxicity to certain organs such as the liver, kidney and pancreas. The TLR8 inhibitor may have a safety profile that is unexpected and advantageous. A safety profile includes evaluation of toxicity, histological profile, and/or necrosis (e.g., liver, kidneys and/or heart). The TLR8 inhibitor may have a therapeutically acceptable level of toxicity. The TLR8 inhibitor may have a reduced level of toxicity as compared to another TLR8 inhibitor. The TLR8 inhibitor may have a better (e.g., lower severity score) histology profile upon evaluation of the liver, kidneys and/or heart, for example. The TLR8 inhibitor may have a therapeutically acceptable necrosis score. The TLR8 inhibitor may have reduced necrosis and/or better (e.g., lower) necrosis score, for example, as compared to a reference TLR inhibitor. The TLR8 inhibitor may have reduced renal and/or hepatocellular necrosis and/or a better renal and/or hepatocellular necrosis score, for example, as compared to a reference TLR inhibitor.

In any of the methods of this disclosure involving administration of a TLR inhibitor to an individual (e.g., methods of inhibiting an immune response, treating or preventing an autoimmune disease or inflammatory disorder, etc.), the TLR inhibitor has therapeutically acceptable pharmacokinetics (PK) or drug metabolism and pharmacokinetics (DMPK). In any of these methods, the TLR8 inhibitor has a PK profile or PK similar to another TLR inhibitor. The therapeutically acceptable safety profile may be determined in mice or rats.

In any of the methods involving administration of a TLR8 inhibitor of this disclosure to an individual (e.g., methods of inhibiting an immune response, treating or preventing an autoimmune disease or inflammatory disorder, etc.) the TL8R inhibitor may induce a therapeutically acceptable level of B-cell activation. The TLR8 inhibitor may induce a low level of B-cell activation as compared to a positive control compound (e.g., an immunostimulatory sequence). The TLR8 inhibitor may induce a low level of B-cell activation, which is comparable to, or not significantly higher than, another TLR inhibitor known to have low B-cell activation. The TLR inhibitor may induce B-cell activation to levels significantly less than about 1-fold, 1.5-fold, 2-fold, 2.5-fold, or 3-fold as compared to another TLR8 inhibitor known to have low B-cell activation. The TLR inhibitor may show concentration-dependent, B-cell activation.

Administration of TLR Inhibitors and Assessment of Immune Responses As with all compositions for inhibition of an immune response, the effective amounts and method of administration of the particular TLR8 inhibitor formulations of this disclosure can vary based on the individual, what condition is to be treated, and other factors evident to one skilled in the art.

In some aspects, the dosage of the TLR inhibitor is sufficient for suppression of a response to a TLR8 agonist, suppression of a TLR8-dependent immune response, suppression of a TLR8-dependent immune response, ameliorating one or more symptoms of an autoimmune disease, ameliorating a symptom of chronic inflammatory disease, decreasing cytokine production in response to HIV, and/or treating and/or preventing one or more symptoms of a disease or disorder mediated by TLR8. In some aspects, at least one TLR8 inhibitor of this disclosure is administered in an amount effective to inhibit an immune response in the individual.

A suitable dosage range is one that provides the desired regulation of immune response (e.g., suppression of a TLR8 agonist or suppression of IFN or other cytokine production in response to a TLR8 agonist). Generally, dosage is determined by the amount of the TLR8 inhibitor administered to the individual. Useful dosage ranges of a composition comprising a TLR inhibitor, may be, for example, any of the following: 0.1 to 10 mg/kg, 0.5 to 10 mg/kg, 1 to 10 mg/kg, 0.1 to 20 mg/kg, 0.1 to 20 mg/kg, or 1 to 20 mg/kg. The absolute amount given to each individual depends on pharmacological properties such as bioavailability, clearance rate and route of administration.

For treatment of an individual, depending on activity of the agent, manner of administration, purpose of the administration (i.e., prophylactic or therapeutic), nature and severity of the disorder, age and body weight of the individual, different doses may be necessary. Dosages are generally selected by the physician or other health care professional in accordance with a variety of parameters known in the art, such as severity of symptoms, history of the individual and the like. An effective amount of the TLR8 inhibitor may be used in the methods described herein.

The administration of a given dose can be carried out both by single administration in the form of an individual dose unit or else in several smaller dose units. Repeated and multiple administration of doses at specific intervals of days, weeks, or months apart are also contemplated.

The effective amount and method of administration of the particular TLR inhibitor formulation can vary based on the individual patient, desired result and/or type of disorder, the stage of the disease and other factors evident to one skilled in the art. The route(s) of administration useful in a particular application are apparent to one of skill in the art. Routes of administration include but are not limited to topical, dermal, transdermal, trans-mucosal, epidermal, parenteral, gastrointestinal, and naso-pharyngeal and pulmonary, including transbronchial and trans-alveolar. A suitable dosage range is one that provides sufficient TLR inhibitor-containing formulation to attain a tissue concentration of about 1-50 microM as measured by blood levels. The absolute amount given to each patient depends on pharmacological properties such as bioavailability, clearance rate and route of administration.

Any one of the pharmaceutical formulations comprising a TLR8 inhibitor of this disclosure, described above may be administered by systemic (e.g., parenteral) or local (e.g., topical or intralesional injection) administration. The pharmaceutical formulation may be administered topically, parenterally, orally, vaginally, intrauterine, intranasal, or by inhalation. As described herein, tissues in which unwanted immune activation is occurring or is likely to occur are preferred targets for the TLR8 inhibitor. Thus, administration of the TLR8 inhibitor to lymph nodes, spleen, bone marrow, blood, as well as tissue exposed to virus, are preferred sites of administration.

The pharmaceutical formulation comprising a TLR8 inhibitor of this disclosure is administered parenterally. Parenteral routes of administration include, but are not limited to, transdermal, trans-mucosal, nasopharyngeal, pulmonary and direct injection. Parenteral administration by injection may be by any parenteral injection route, including, but not limited to, intravenous (IV), including bolus and infusion (e.g., fast or slow), intraperitoneal (IP), intramuscular (IM), subcutaneous (SC) and intradermal (ID) routes. Transdermal and trans-mucosal administration may be accomplished by, for example, inclusion of a carrier (e.g., dimethylsulfoxide, DMSO), by application of electrical impulses (e.g., iontophoresis) or a combination thereof. A variety of devices are available for transdermal administration which may be used. Formulations of TLR8 inhibitors suitable for parenteral administration are generally formulated in USP water or water for injection and may further comprise pH buffers, salts bulking agents, preservatives, and other pharmaceutically acceptable excipients. Immunoinhibitory compound for parenteral injection may be formulated in pharmaceutically acceptable sterile isotonic solutions such as saline and phosphate buffered saline for injection.

Transdermal administration is accomplished by application of a cream, rinse, gel, etc. capable of allowing the TLR inhibitor to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference. Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter. Delivery via transdermal and trans-mucosal routes may be continuous or pulsatile.

Gastrointestinal routes of administration include, but are not limited to, ingestion and rectal routes and can include the use of, for example, pharmaceutically acceptable powders, pills or liquids for ingestion and suppositories for rectal administration.

Naso-pharyngeal and pulmonary administration include are accomplished by inhalation, and include delivery routes such as intranasal, transbronchial and trans-alveolar routes. Formulations of TLR8 inhibitors suitable for administration by inhalation including, but not limited to, liquid suspensions for forming aerosols as well as powder forms for dry powder inhalation delivery systems are provided. Devices suitable for administration by inhalation of TLR8 inhibitor formulations include, but are not limited to, atomizers, vaporizers, nebulizers, and dry powder inhalation delivery devices. Other methods of delivering to respiratory mucosa include delivery of liquid formulations, such as by nose drops. Administration by inhalation is preferably accomplished in discrete doses (e.g., via a metered dose inhaler), although delivery similar to an infusion may be accomplished through use of a nebulizer.

As described herein, tissues in which unwanted immune activation is occurring or is likely to occur are suitable targets for the TLR8 inhibitors of this disclosure. Thus, administration of the TLR inhibitor composition to lymph nodes, spleen, bone marrow, blood, as well as tissue exposed to virus, are preferred sites of administration.

As is well known in the art, solutions or suspensions used for the routes of administration described herein can include any one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diamine tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

As is well known in the art, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. It may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

As is well known in the art, sterile injectable solutions can be prepared by incorporating the active compound(s) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In any of the methods described herein a TLR8 inhibitor of this disclosure may be administered in an amount sufficient to inhibit an immune response. As described herein, the immune response may be humoral and/or cellular, and is measured using standard techniques in the art and as described herein. In some aspects, provided herein are methods for suppressing, reducing, and/or inhibiting TLR8 dependent cell stimulation (e.g., TLR signaling in a cell expressing the TLR). In some aspects, at least one TLR inhibitor is administered in an amount effective to inhibit an immune response in the individual.

The TLR8 inhibitors of this disclosure suppress TLR8-dependent immune responses. Methods are provided herein for inhibiting a TLR8 immune response in an individual, comprising administering a TLR8 inhibitor of this disclosure in an amount sufficient to suppress TLR8 cytokine production in the individual. The TLR8 immune response may be an innate immune response. The TLR8 immune response may be an adaptive immune response.

The compositions described herein may inhibit a response of a monocytes, macrophages, myeloid dendritic cells, regulatory T-cells, B-cells, and neutrophils. The immune responses inhibited by the compositions described herein may include inhibition of cytokine production, such as IL-1beta and/or TNF, by the cell, inhibition of cell maturation and/or inhibition of cell proliferation. The compositions described herein may inhibit a TLR-8-dependent cell response.

The above-mentioned compositions and methods of administration are meant to describe but not limit the methods of administering the formulations of TLR8 inhibitors described herein. The methods of producing the various compositions and devices are within the ability of one skilled in the art.

Combination Therapy

The TLR inhibitors of the present disclosure can be administered in combination with one or more additional therapeutic agents. As described herein, the TLR8 inhibitors can be combined with a physiologically acceptable carrier. The methods described herein may be practiced in combination with other therapies that make up the standard of care for the disorder, such as administration of anti-inflammatory agents.

A TLR inhibitor of this disclosure may be administered in combination with a corticosteroid, such as a glucocorticosteroid or a mineralocorticoid. Corticosteroids include, but are not limited to, corticosterone and derivatives, prodrugs, isomers and analogs thereof, cortisone and derivatives, prodrugs, isomers and analogs thereof (i.e., Cortone), aldosterone and derivatives, prodrugs, isomers and analogs thereof, dexamethasone and derivatives, prodrugs, isomers and analogs thereof (i.e., Decadron), prednisone and derivatives, prodrugs, isomers and analogs thereof (i.e., Prelone), fludrocortisones and derivatives, prodrugs, isomers and analogs thereof, hydrocortisone and derivatives, prodrugs, isomers and analogs thereof (i.e., cortisol), hydroxycortisone, betamethasone, budesonide, methylprednisolone, prednisolone, triamcinolone, and derivatives, prodrugs, isomers, and analogs of any of these corticosteroids.

The TLR8 inhibitors of this disclosure may be administered simultaneously with one or more additional therapeutic agents including, but not limited to, a corticosteroid (simultaneous administration). The TLR8 inhibitor may be administered sequentially with an additional therapeutic agent including, but not limited to, a corticosteroid (sequential administration). Sequential administration may include administering the TLR8 inhibitor or additional therapeutic agent followed within about any of one minutes, five minutes, 30 minutes, one hour, five hours, 24 hours, 48 hours, or a week. The TLR8 inhibitor may be administered by the same route of administration as the additional therapeutic agent. The TLR8 inhibitor may be administered by a different route of administration than the additional therapeutic agent. The additional therapeutic agent may be administered parentally (e.g., central venous line, intra-arterial, intravenous, intramuscular, intraperitoneal, intradermal, or subcutaneous injection), orally, gastrointestinally, topically, nasopharyngeal and pulmonary (e.g. inhalation or intranasally).

The combination of a TLR8 inhibitor with one or more additional therapeutic agents reduces the effective amount (including, but not limited to, dosage volume, dosage concentration, and/or total drug dose administered) of the TLR8 inhibitor and/or the one or more additional therapeutic agents administered to achieve the same result as compared to the effective amount administered when the TLR8 inhibitor or the additional therapeutic agent is administered alone. Alternatively or additionally, the combination of a TLR8 inhibitor with a corticosteroid reduces the effective amount of corticosteroid administered as compared to the corticosteroid administered alone. The combination of a TLR8 inhibitor with the additional therapeutic agents may reduce the frequency of administrations of the therapeutic agent compared to administration of the additional therapeutic agent alone. Alternatively or additionally, the combination of a TLR8 inhibitor with the additional therapeutic agent reduces the total duration of treatment compared to administration of the additional therapeutic agent alone. The combination of a TLR8 inhibitor with the additional therapeutic agent may reduce the side effects associated with administration of the additional therapeutic agent alone. The additional therapeutic agent may be a corticosteroid.

TLR8 inhibitors also may be useful as a vaccine adjuvant for use in conjunction with any material that modulates either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; glycoproteins; peptides; and the like. In some aspects, the combination therapy including but not limited to the combination of a TLR8 inhibitor and a vaccine is used in the treatment of an autoimmune disease or an inflammatory disorder. In some aspects, the combination therapy including but not limited to the combination of a TLR8 inhibitor and a vaccine is used in the treatment of an infectious disease.

The combination therapy may include, but is not limited to, the combination of a TLR8 inhibitor of this disclosure and a corticosteroid used in the treatment of an autoimmune disease or an inflammatory disorder. The autoimmune disease may be selected from rheumatoid arthritis, systemic lupus erythematosus, autoimmune skin disease, multiple sclerosis, pancreatitis, glomerulonephritis, pyelitis, Sclerosing cholangitis, and type I diabetes, or Sjogren's disease.

Kits, Vials, and Unit Dosage Forms

Also provided herein are kits comprising a TLR8 inhibitor of this disclosure and instructions for use in the methods of inhibiting a TLR8-dependent immune response.

The kits may comprise one or more containers comprising a TLR8 inhibitor of this disclosure (or a formulation comprising a TLR inhibitor) and a set of instructions, generally written instructions, although electronic storage media (e.g., magnetic diskette or optical disk) containing instructions are also acceptable, relating to the use and dosage of the TLR8 inhibitor or formulation for the intended treatment (e.g., suppression of a response to a TLR8 agonists, suppression of a TLR8-dependent immune response, ameliorating one or more symptoms of an autoimmune disease, ameliorating a symptom of chronic inflammatory disease, decreasing cytokine production in response to a virus, and/or treating and/or preventing one or more symptoms of a disease or disorder mediated by TLR8). The instructions included with the kit generally include information as to dosage, dosing schedule, and route of administration for the intended treatment. The containers for the TLR8 inhibitor (or formulations comprising a TLR8 inhibitor) may be unit doses, bulk packages (e.g., multi-dose packages) or sub-unit doses. The kits may further comprise a container comprising an adjuvant.

The container of the kits may include at least one vial, test tube, flask, bottle, syringe or other container, into which a component may be placed, and preferably, suitably aliquoted. Where there is more than one component in the kit, the kit may contain a second, third or other additional container into which the additional components may be separately placed. However, various combinations of components may be comprised in a vial. The kits also will typically include a component for containing the containers in close confinement for commercial sale.

When the components of the kit are provided in one and/or more liquid solutions, the liquid solution is an aqueous solution, with a sterile aqueous solution being particularly preferred. The components of the kit may also be provided as dried powder(s). When reagents and/or components are provided as a dry powder, the powder can be reconstituted by the addition of a suitable solvent. It is envisioned that the solvent may also be provided in another container.

The TLR8 inhibitor formulation component of the kit may be packaged in any convenient, appropriate packaging. For example, if the TLR8 inhibitor is a freeze-dried formulation, a vial with a resilient stopper is normally used, so that the TLR8 inhibitor may be easily reconstituted by injecting fluid through the resilient stopper. Ampoules with non-resilient, removable closures (e.g., sealed glass) or resilient stoppers are most conveniently used for injectable forms of TLR8 inhibitor. Also, prefilled syringes may be used when the kit is supplied with a liquid formulation of the TLR8 inhibitor. The kit may contain the TLR8 inhibitor in an ointment for topical formulation in appropriate packaging. Also contemplated are packages for use in combination with a specific device, such as an inhaler, nasal administration device (e.g., an atomizer), transdermal administration device, or an infusion device such as a minipump.

A kit may include instructions for employing the kit components as well as the use of any other reagent(s) not included in the kit.

Also provided are vials (e.g., sealed vials) comprising any one of the TLR8 inhibitor or formulations described herein. In some embodiments, the vials comprising the TLR8 inhibitor in combination with a vial comprising a therapeutic agent. In some embodiments, wherein the vials are provided in a kit.

Also provided are unit dosage forms for the treatment and/or prevention of a disease or disorder mediated by TLR8, the dosage forms comprising any one of the TLR8 inhibitor or formulations described herein. In some embodiments, the unit dosage forms comprising the TLR inhibitor in combination with a unit dosage form of a therapeutic agent. In some embodiments, the dosage forms are provided in a kit.

Another embodiment of the disclosure relates to the use of any of the TLR8 inhibitors of this disclosure or compositions described herein in the preparation of a medicament for the treatment or prevention of a TLR8-mediated immune response.

Each publication or patent cited herein is incorporated herein by reference in its entirety. The invention having been generally described will be more readily understood by reference to the following examples, which are included merely for the purposes of illustration of certain aspects of the embodiments of the invention. The examples are not intended to limit the disclosure, as one of skill in the art would recognize from the above teachings and the following examples that other techniques and methods can satisfy the claims and can be employed without departing from the scope of the invention.

EXAMPLES

The following methods were used to conduct the experiments described in Examples 1-6, below:

Cell Lines: The human embryonic kidney (HEK)-Blue Null1 (gender: female), HEK-Blue cells (gender: female) with overexpressing of TLR2, TLR4, TLR7, and TLR9 were purchased from Invivogen. HEK-Blue cells overexpressing TLR3, TLR5 and TLR8 were generated from HEK-Blue Null1 cells by lentiviral infection. HEK-Blue cells were grown in humidified incubators containing 5% $CO_2$ at 37° C. HEK-Blue TLR cells were cultured in DMEM media supplemented with 10% fetal bovine serum (FBS), 50 U/mL penicillin and 50 µg/mL streptomycin (PenStrep), 100 mg/mL normocin, 5 g/mL blasticidin and 2 mM L-glutamine. THP-1 cells (gender: male) were purchased from ATCC (Virginia, USA). THP-1 cells were grown in humidified incubators containing 5% $CO_2$ at 37° C. THP-1 cells were cultured in RPMI 1640 medium supplemented with 10% fetal FBS, 100 U/mL penicillin, 100 µg/mL streptomycin (Pen Strep), 2 mM L-glutamine, and 0.05 mM 2-mercaptoethanol. HEK-Blue TLR cells and THP-1 cells are used without further authentication. Cells were checked periodically and were found to be free of mycoplasma contamination. Spleens were isolated from TLR7 knock-out mice (gender: female) harboring a human TLR8 transgene. PBMC cells were collected from anonymous donors.

SEAP reporter assay: HEK-Blue TLR8 cells were seeded in tissue culture treated 96-well plates with a density of $7.5 \times 10^4$ cells/well in DMEM media supplemented with 10% FBS (phosphatases deactivated with heat). Cells were then treated with R848 (1 μg/mL) along with various concentrations of appropriate compounds. Plates are then incubated in humidified incubators containing 5% $CO_2$ at 37° C. for 24 h, after which, 30 μL of culture media was transfer to a new plate and 100 μL of Quanti-Blue (Invivogen) was added, the plate was then incubated at 37° C. till color change (30 min-1 h). Readout of absorbance at 620 nm was quantified using Beckman-Coulter DTX 880 Multimode Detector. Readout of only R848 treated cells were normalized as 100% activation, and untreated cells as 0% activation. SEAP assays for each sample were conducted with three biological replicates, each in triplicate.

WST-1 cell proliferation assay: HEK-Blue cells overexpressing TLRs were treated as described in SEAP assay. After incubation of 24 h, supernatant was removed, and 100 μL of 1:10 diluted WST-1 (Roche) was then added to each well. The plate was then incubated at 37° C. till color change (30 min-1 h). Readout of absorbance at 450 nm was quantified using Beckman-Coulter DTX 880 Multimode Detector. Readouts of untreated cells were normalized as 100% survival, and 20% DMSO treated cells as 0% activation.

TLR selectivity assay: The selectivity of sample compound was tested using SEAP reporter assay in HEK-Blue overexpressing various TLRs. Plates were set up in same manner as described in SEAP assay above. Instead of R848, for HEK-Blue hTLR1/2, hTLR2/6, hTLR3, hTLR4, hTLR5, hTLR7, and hTLR9 cells, Pam3CSK4 (100 ng/mL), Pam2CSK4 (100 ng/mL), poly(I:C) (5 μg/mL), LPS (lipopolysaccharide) (20 ng/mL), flagellin (50 ng/mL), R848 (1 μg/mL), ODN2006 (0.15 μM) were used as agonists, respectively.

Protein expression, purification and crystallization: The extracellular domain of human Toll-like receptor 8 (hTLR8, residues 27-827) was prepared as described previously (Tanji, et al., 2013 Science 339:1426-29) and was concentrated to 16 mg/mL in 10 mM Tris-HCl pH 8.0 and 150 mM NaCl. The protein solutions for the co-crystallization of hTLR8 and inhibitors contained hTLR8 (7.0 mg/mL) and a five-fold excess of inhibitors in a crystallization buffer containing 10 mM Tris-HCl pH 8.0, 150 mM NaCl, and 5% dimethyl sulfoxide (DMSO). Crystallization experiments were performed with sitting-drop vapor-diffusion methods at 293 K. Crystals of hTLR8/CU-CPT were obtained with reservoir solutions containing 12.5-13.0% PEG 4000, 0.2 M calcium chloride, 0.1 M Tris-HCl pH 8.0-8.3, and 20-25% ethylene glycol.

Data collection and structure determination: Diffraction dataset was collected on beamline, PF BL-5A (Ibaraki, Japan), and SPring-8 BL41XU (Hyogo, Japan) under cryogenic condition at 100 K. The wavelength was set to 1.0000 Å. The dataset was processed using the HKL2000 package or iMOSFM. hTLR8/CU-CPT structures were determined by the molecular replacement method using the Molrep program with the unliganded hTLR8/CU-CPT8m structure (PDB ID: 5WYX) as a search model. The model was further refined with stepwise cycles of manual model building using the COOT program and restrained refinement using REFMAC until the R factor was converged. CU-CPT compounds, N-glycans, and water molecules were modeled into the electron density maps at the latter cycles of the refinement. The quality of the final structure was validated with the PDB validation server (wwpdb-validation.wwpdb.org/). The favored and the allowed regions in the Ramachandran plot were 88% and 11% for TLR8/CU-CPT9a, and 89% and 10% for TLR8/CU-CPT9c. The figures representing structures were prepared with PyMOL (pymol.org) or CueMol (cuemol.org). Coordinates and structure factor have been deposited in the Protein Data Bank with PDB as 5Z14 (TLR8/CU-CPT9a), 5WYZ (TLR8/CU-CPT9b), and 5Z15 (TLR8/CU-CPT9c).

Isothermal titration calorimetry (ITC): ITC was performed in a buffer composed of 25 mM MES pH 5.5, 0.20 M NaCl, and 2.5% DMSO at 298 K using a MicroCal iTC200 (GE Healthcare, Illinois, USA). The titration sequence included a single 0.4 NL injection followed by 18 injections, 2 μL each, with a spacing of 120 seconds between the injections. The titration conditions were as follows: 100 μM inhibitors into 10 μM hTLR8; 100 μM R848 into 10 μM hTLR8/50 μM inhibitors. OrigineLab software (GE Healthcare) was used to analyze the raw ITC data.

Immunoblotting: THP-1 cells were seeded in 6-well plates with a density of $2 \times 10^6$ cells/well in RPMI 1640 medium supplemented with 10% FBS, 100 U/mL penicillin, 100 μg/mL streptomycin (PenStrep), 2 mM L-glutamine, and 0.05 mM 2-mercaptoethanol. THP-1 cells were treated with phorbol-12-myristate-13-acetate (PMA) (100 ng/mL) and incubated in humidified incubators containing 5% $CO_2$ at 37° C. for 24 h. After differentiation, the supernatant was then removed and replaced with unsupplemented RPMI, these cells were then treated with R848 (1 μg/mL) along with various concentrations of appropriate compounds. After incubation of 2 h, THP-1 cells were collected, nuclear protein fraction was extracted using NE-PER Nuclear and Cytoplasmic Extraction kit (Thermo Fisher Scientific). BCA assay was then used to determine protein concentration. Protein samples were loaded and run in 10% Tris-glycine SDS-PAGE, and then transferred onto a nitro-cellulose membrane (BioRad) using electroblotting. P65 (CST; 8242) (1:1000) was then used as primary antibody, and peroxidase-conjugated AffiniPure Goat Anti-Rabbit IgG (H+L) antibody (Jackson Immuno Research; 111-035-144) (1:10000) as secondary antibody, then blots were visualized using Thermo SuperSignal West Pico kit (Thermo Fisher Scientific). Lamin A/C (CST; 2032) were used as internal controls for nuclear fractions.

Activity on primary human lymphocytes: Buffy coats from human donors were obtained from the Stanford Blood Center and lymphocytes isolated using Ficoll-Paque. For assessing antagonist activity against TLR2, 4, and 5 the entire PBMC population was used. For assessing antagonist activity against TLR7, 8 and 9 specific lymphocyte subsets were isolated using the QuadroMACS Separator System (Miltenyi) and CD19 or CD14 microbeads to isolate B cells (for TLR7 and 9) and monocytes (for TLR8), respectively. Cells were incubated with a dilution series of compounds and a constant amount of agonist. The following agonists were used for each TLR: Pam2CSK4 (0.35 mg/mL) for TLR2, lipopolysaccharide (0.35 mg/mL) for TLR4, flagellin (0.75 mg/mL) for TLR5, R848 (1 mg/mL) for TLR7, RNA oligonucleotide ORN8L (100 mg/mL) for TLR8, and CpG-containing phosphorothioate DNA oligonucleotide 1018 (1 mM) for TLR9. After 24 to 48 hours, culture supernatants were collected and analyzed for cytokine production indicative of TLR activity (IL-6 from PBMCs and B cells, TNF-alpha from monocytes). Each activity curve was an average from three individual donors.

Activity on primary mouse splenocytes: To assess TLR8 and TLR9 activity, spleens were isolated from TLR7 knock-out mice harboring a human TLR8 transgene (hTLR8tg/TLR7-KO). Splenocytes were prepared by dissociation through a cell strainer and removal of red blood cells with lysis buffer. Splenocytes were incubated with a dilution series of compounds and a constant amount of a TLR8 agonist (RNA oligonucleotide ORN8L) or a TLR9 agonist (CpG-containing phosphorothioate DNA oligonucleotide 1018). After 48 hours, culture supernatants were collected and analyzed for IL-12p40 production. Curves represent activity from a single spleen.

Quantification and statistical analysis: Statistical differences were performed using one-way ANOVA with Bonferroni post-test for multiple comparisons. All statistical analyses were performed using GraphPad Prism, version 6.0 for Mac and OriginPro, a P value of <0.05 was considered statistically significant.

Example 1: Identification of Potent and Selective TLR8 Inhibitors

Figure 2:
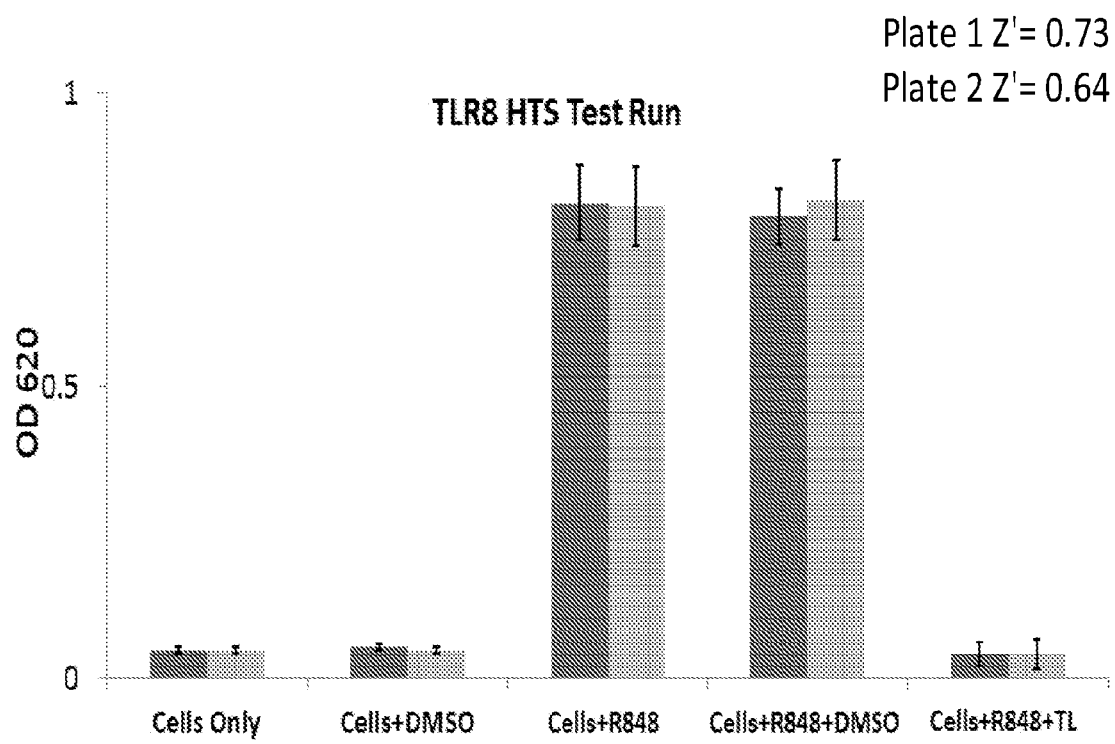
FIG. 2 shows an average Z'-factor of 0.68 was determined with two independent replicates, demonstrating that the HTS assay is robust. A previously established NF-κB inhibitor, triptolide (TL.

To establish a robust high throughput assay for TLR8 inhibitors, the inventors first engineered a cell line stably overexpressing the human TLR8 whose activation can be reported by the Secreted Embryonic Alkaline Phosphatase (SEAP) assay. TLR8-overexpresing HEK-Blue cells were prepared by lentiviral infection of HEK-Blue Null1 cells that have null or low basal expression of endogenous TLR genes. The overexpression and endosomal localization of human TLR8 was confirmed using confocal microscopy. The TLR8-mediated NF-κB activation can be assessed by measuring the SEAP activity. Using a previously established NF-κB inhibitor, triptolide (FIG. 1), as the positive control, a Z'-factor of 0.68 was determined (FIG. 2), demonstrating that this assay is robust for high throughput screening (HTS).

The inventors next screened a 14,400-membered commercial library (Maybridge HitFinder V11) of diverse, drug-like compounds, which led to 72 compounds identified as "hits" inhibiting TLR8 signaling by >85% at 4 μM. The small molecule screening data is shown in the following Table:

| Category | Parameter | Description |
|---|---|---|
| Assay | Type of assay | Cell-based |
| | Target | Toll-like Receptor 8 signaling pathway |
| | Primary measurement | Detection of TLR8-inducted secreted embryonic alkaline phosphatase (SEAP) concentration in the culture media |
| | Key reagents | R848, QUANTI-Blue ™, Triptolide (Invitrogen) |
| | Assay protocol | invivogen.com/quanti-blue |
| Library | Library size | 14,400 |
| | Library composition | Drug-like molecules |
| | Source | Maybridge |
| Screen | Format | 384-well plate |
| | Concentration(s) tested | 4 μM, 0.04% DMSO |
| | Plate controls | DMSO (0.04%) was used as negative control. Triptolide (30 nM) was used as positive control. The screening was performed in 2 biological replicates. |
| | Reagent/compound dispensing system | BioTek Precision Microplate Pipetting System |

-continued

| Category | Parameter | Description |
|---|---|---|
| | Detection instrument and software | PerkinElmer EnVision 2102 Multilabel Plate Reader, Version: 1.13.3009.1409 |
| | Assay validation/QC | Z' score = 0.68 Standard deviation of positive control = 0.01 |
| | Correction factors | Background absorbance from the dye was subtracted from screening raw data. |
| | Normalization | Data were normalized as percentage activity relative to positive control. |
| | Additional comments | University of Colorado Boulder HTS Core Facility |
| Post-HTS analysis | Hit criteria | Compounds that inhibited TLR8-mediated SEAP production greater than 85% were considered active. |
| | Hit rate | 0.5% |
| | Additional assay(s) | Toxicity Assay (WST-1), Specificity Assay |
| | Confirmation of hit purity and structure | Compounds were purchased from Fisher Scientific/Maybridge for validation |

Cytotoxicity testing at 100 μM further narrowed down these initial hits to 13. Four compounds (SB1723, SEW04865, BTB08278, and BTB08295) were eventually selected, as they had proven to be specific TLR8 signaling inhibitors over other homologous TLRs. Interestingly, these four compounds present two distinct chemical scaffolds: SB1723 and SEW04865 both share a 7-phenylpyrazolo[1,5-a]pyrimidine backbone, while BTB08278 and BTB08295 both contain a 4-phenyl-1-(2H)-phthalazinone core structure.

Figure 3:
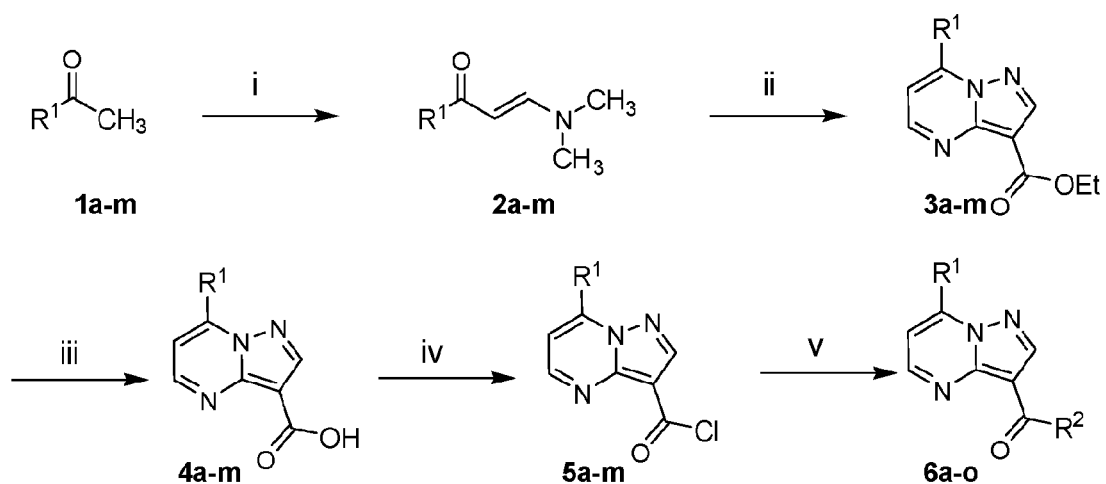
FIG. 3 shows the scheme for synthesis of pyrazolo[1,5-a]pyrimidine derivatives. Reagents and conditions: (i) 1,1-dimethoxy-N,N-dimethylmethanamine (DMF-DMA), reflux; (ii) 5-amino-4-ethoxycarbonyl-1H-pyrazole, AcOH, reflux; (iii) NaOH, $H_2O$/EtOH, 80° C.; then acidify with 1M hydrochloric acid; (iv) $SOCl_2$, reflux; (v) DCM, $NH_3$ in THF, or DCM, methylamine in THF (6n), or DCM, diethylamine in THF (6o).
Figure 4A:
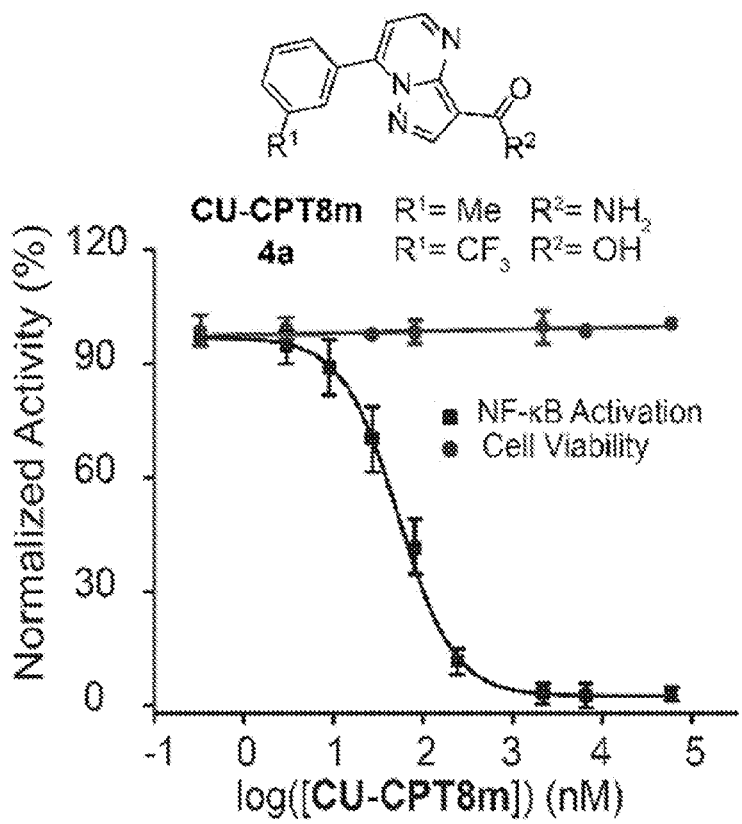
FIGS. 4A-4F show that CU-CPT8m potently and selectively inhibits TLR8.

In order to obtain a more potent small molecule probe for TLR8, the inventors developed a concise synthetic route for the 7-phenylpyrazolo[1,5-a]pyrimidine scaffold for optimization (FIG. 3). SAR studies led to the identification of compound 6b (later given the laboratory designation CU-CPT8m) with an IC$_{50}$ of 67±10 nM and negligible cytotoxicity (FIG. 4A). Representative structure-activity relationship (SAR) results for inhibitory activities of pyrazolo[1,5-a]pyrimidine derivatives in HEK-Blue hTLR8 cells are provided in the following table:

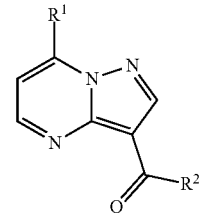

| Compound No. | R$^1$ | R$^2$ | IC$_{50}$ [nM]$^a$ |
|---|---|---|---|
| 3a | 3-CF$_3$—C$_6$H$_4$— | —OEt | 210 ± 43 |
| 3b | 3-Me—C$_6$H$_4$— | —OEt | 92 ± 15 |
| 4a | 3-CF$_3$—C$_6$H$_4$— | —OH | >20,000 |
| 4b | 3-Me—C$_6$H$_4$— | —OH | >20,000 |
| 6a | 3-CF$_3$—C$_6$H$_4$— | —NH$_2$ | 130 ± 30 |
| 6b (CU-CPT8m) | 3-Me—C$_6$H$_4$— | —NH$_2$ | 67 ± 10 |
| 6c | 2-CF$_3$—C$_6$H$_4$— | —NH$_2$ | 230 ± 140 |
| 6d | 4-CF$_3$—C$_6$H$_4$— | —NH$_2$ | 1,220 ± 200 |
| 6e | Phenyl— | —NH$_2$ | 760 ± 230 |
| 6f | 3-NO$_2$—C$_6$H$_4$— | —NH$_2$ | 220 ± 70 |
| 6g | 3-F—C$_6$H$_4$— | —NH$_2$ | 450 ± 90 |
| 6h | 3-Cl—C$_6$H$_4$— | —NH$_2$ | 280 ± 100 |
| 6i | 3,5-diCF$_3$—C$_6$H$_3$— | —NH$_2$ | 250 ± 130 |
| 6j | 2-OMe—C$_6$H$_4$— | —NH$_2$ | 2,310 ± 220 |

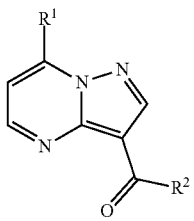

| Compound No. | R¹ | R² | IC$_{50}$ [nM]$^a$ |
|---|---|---|---|
| 6k | 3-OMe—C$_6$H$_4$— | —NH$_2$ | 1,200 ± 200 |
| 6l | 3-Pyridyl | —NH$_2$ | >20,000 |
| 6m | 3-Et—C$_6$H$_4$— | —NH$_2$ | 120 ± 23 |
| 6n | 3-CF$_3$—C$_6$H$_4$— | —NHMe | 1,700 ± 300 |
| 6o | 3-CF$_3$—C$_6$H$_4$— | —NEt$_2$ | >20,000 |

$^a$IC$_{50}$ values and corresponding standard deviations were determined from at least three biological replicates.

For this pyrazolo[1,5-a]pryrimidine series compounds, the ester analogs were first evaluated. Comparing with the corresponding amide (6a, 6b), the ethyl esters analogs (3a, 3b) are slightly less potent. The carboxylic acid derivatives (4a, 4b) did not show any inhibitory activity (up to 20 μM) against TLR8 signaling. For this reason, 4a was used as a negative control in the other biological evaluations. The influence of different substituents in the ortho-, meta-, and para-positions of 7-phenyl group on TLR8 inhibition was also explored: analogs with substituent in the meta-position of the phenyl ring show higher potency than the analogues with para- or ortho-substitutions. Compound 6a with trifluoromethyl substituent in the meta-position of the phenyl ring shows a 2-fold higher potency than that of 6c, and 10-fold higher potency than that of 6d. Introduction of a second trifluoromethyl group at the 5-position (6i) however did not change the activity of 6a. The replacement of the phenyl ring of 6e with pyridinyl (8l) resulted in a substantial decrease in potency (IC$_{50}$ 760 nM to more than 20 μM). A variety of substituents replacing the trifluoromethyl group at the meta-position were synthesized and tested. Substituents with varying electron-withdrawing properties similar to the trifluoromethyl group (such as nitro (8f), chloro (6h) and fluoro (6g)) led to less potent compounds. The presence of methoxy group both on ortho-position (6j) and the meta-position (6k) weaken activity. Interestingly, the introduction of a methyl group at the meta-position (8m) showed a 2-fold stronger inhibitory activity (IC$_{50}$: 67 nM) than the hit compound 6a (IC$_{50}$: 130 nM). It is also observed that the replacement of trifluoromethyl group with ethyl (6m) resulted in comparable inhibitory activity. Furthermore, introduction of alkyl substitutions on the amide nitrogen led to significant reduction of activity. The secondary amide analog (6n) showed a 25-fold reduction in potency, while the tertiary amide analog (6o) had no significant activity even at 20 μM. Altogether, these results demonstrated that pyrazolo[1,5-a]pryrimidine derivatives present a consistent SAR. Compound 8m ("CU-CPT8m") was found to be the most active compound with an IC$_{50}$ of 67±10 nM.

The direct binding of CU-CPT8m to the ectodomain of human TLR8 was confirmed with isothermal titration calorimetry (ITC). The dissociation constant (K$_d$) value of CU-CPT8m was determined to be 220 nM (FIG. 4C), which is comparable to that of R848 (K$_d$=200 nM), a previously established, potent, non-selective TLR7/8 activator.

Figure 4B:
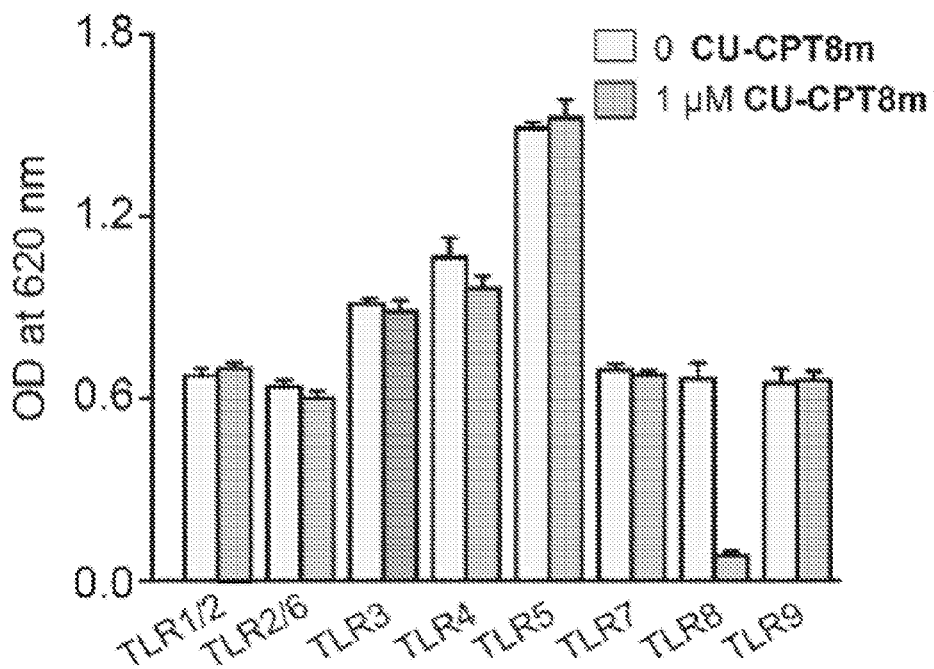
Figure 4C:
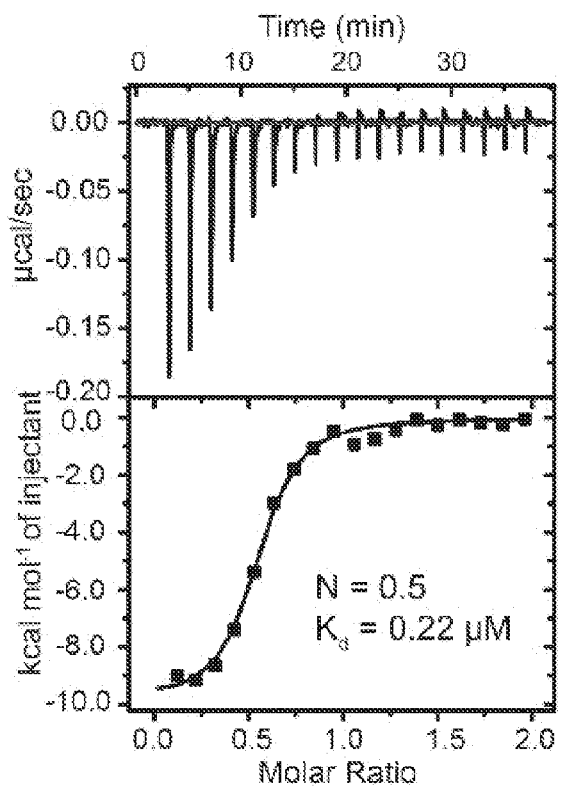
Figure 5:
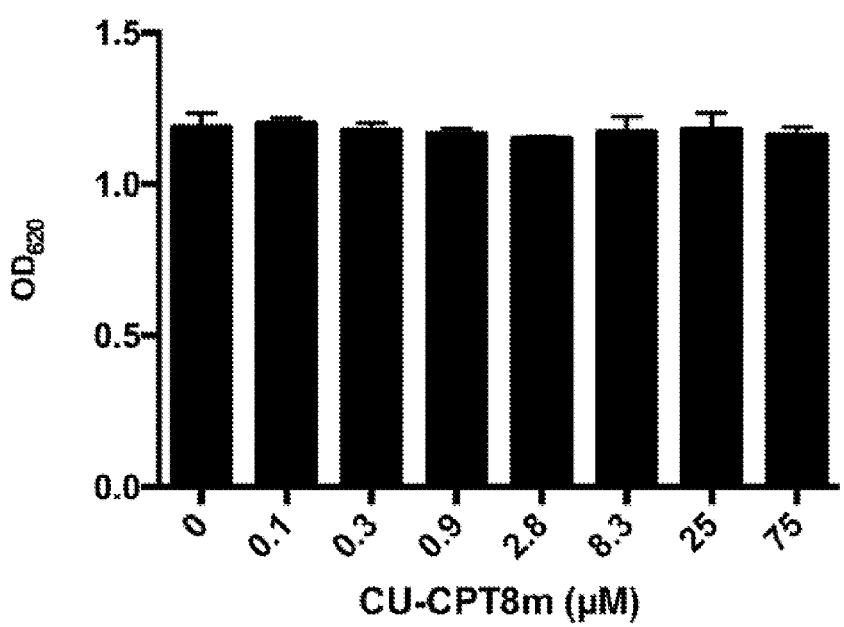
FIG. 5 shows the inhibitory activity of compound CU-CPT8m in HEK-Blue TLR7 cells activated by R848. TLR7-mediated NF-κB activation was not affected by CU-CPT8m at concentrations up to 75 μM. Results shown as mean±s.e.m.

Given that TLR family proteins are homologous membrane receptors, achieving a high degree of selectivity among TLRs is challenging. To determine if CU-CPT8m selectively inhibits TLR8 signaling, the inventors tested CU-CPT8m against all human TLRs. At a concentration of 1 μM, CU-CPT8m did not show significant inhibition of any TLR other than TLR8 in HEK-Blue cells overexpressing each individual TLR (FIG. 4B). These TLR-overexpressing HEK cells (TLR1/2/6, TLR3, TLR4, TLR5, TLR7, and TLR9 HEK-Blue) present distinct ectodomains, but share common downstream effectors. The fact that CU-CPT8m only reduced the proinflammatory response in the TLR8-overexpressing cells strongly supports that CU-CPT8m directly recognizes TLR8 in cells. It is particularly notable that TLR7 signaling was not affected at concentrations up to 75 μM (FIG. 5). TLR7 and TLR8 are closely related and share many common ligands (e.g. R848). The ability of CU-CPT8m to distinguish between TLR8 and TLR7 is the first reported in literature, and implies that a novel molecular recognition mechanism is involved in the inhibition of TLR8 by CU-CPT8m.

Example 2: CU-CPT8m Inhibited TLR8-Mediated Inflammatory Cytokine Production

Figure 4D:
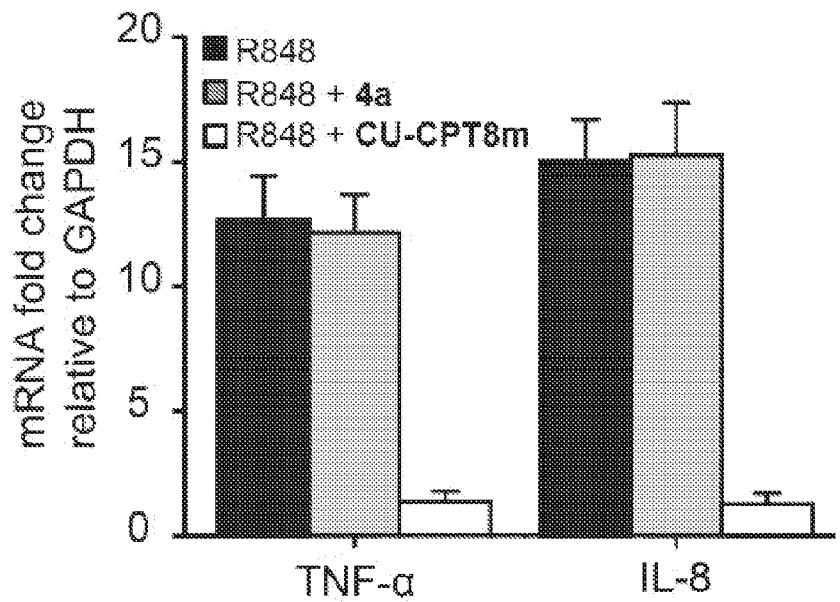

R848-induced TLR8 activation results in increased production of the proinflammatory cytokines, such as TNF-α, IL-6 and IL-8. Next, the inventors examined the inhibitory effects of CU-CPT8m in various cell lines. First, the inhibitory effects of CU-CPT8m on the mRNA level of proinflammatory cytokines by quantitative real-time PCR (RT-PCR) were investigated. As shown in FIG. 4D, treatment of 1 μM CU-CPT8m completely abolished the elevation of TNF-α and IL-8 mRNA levels induced by R848. By contrast, the inactive analog, 4a showed negligible inhibition.

Figure 4E:
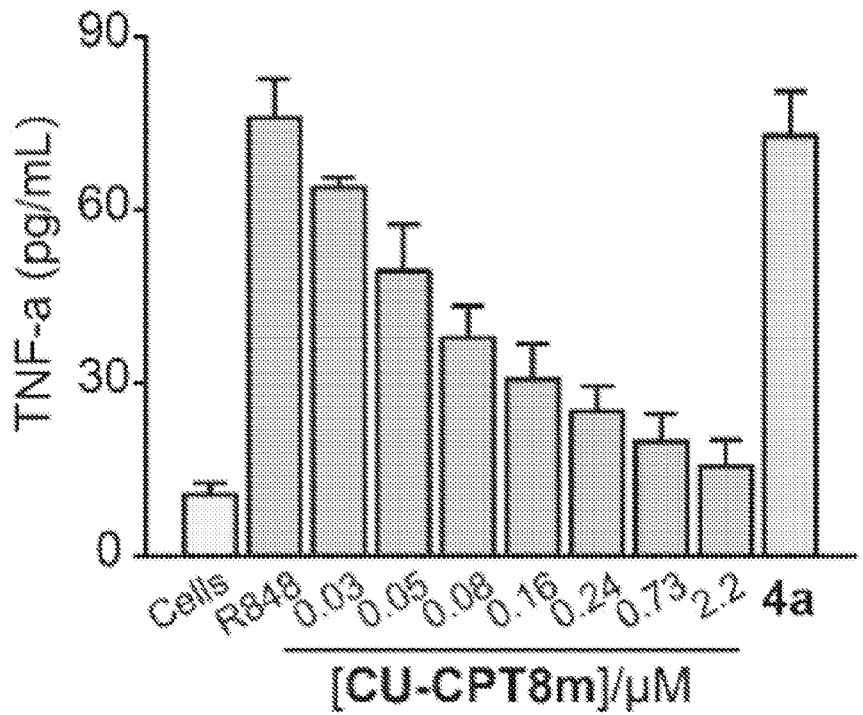

The inventor then showed that CU-CPT8m significantly suppressed the protein level of various cytokines. R848 treatment resulted in a significant elevation of the TNF-α production, reaching a maximum of approximately 10-fold after 24 h. FIG. 4E demonstrates that CU-CPT8m inhibited R848-induced TNF-α production in the differentiated THP-1 monocytes cells in a dose-dependent manner with an IC$_{50}$ value of 90±10 nM, which is in good agreement with its IC$_{50}$ value determined in HEK-Blue TLR8 cells. The negative control, compound 4a, failed to show significant inhibition at 10 μM.

Figure 4F:
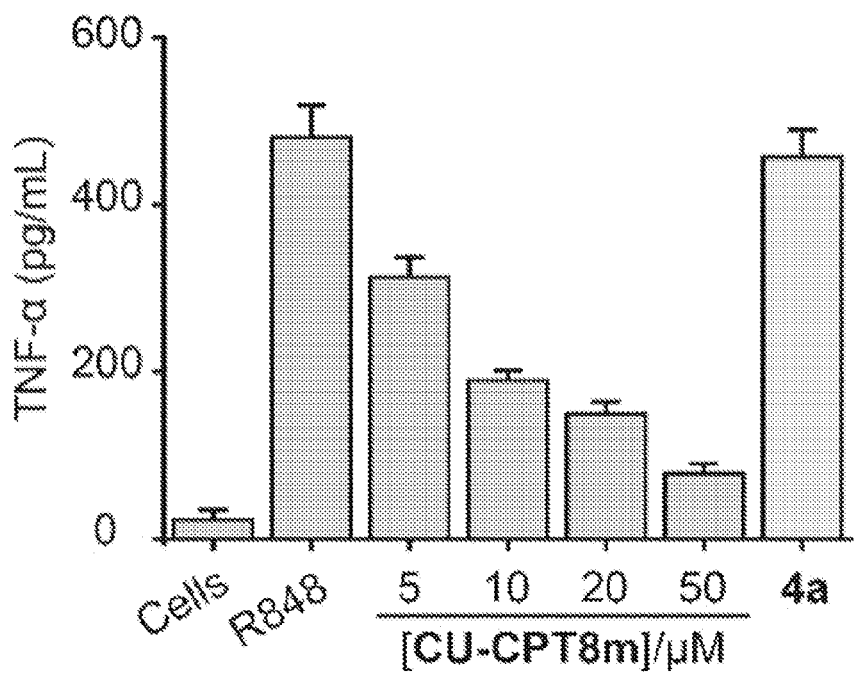

Having identified potent and selective inhibitors of TLR8 in cultured cell lines, we then investigated if CU-CPT8m could regulate TLR8 in primary human cells. Peripheral blood mononuclear cells (PBMCs) include lymphocytes (T cells, B cells, and NK cells), monocytes, and dendritic cells expressing various TLRs. TLR7 and TLR8 are both expressed on B cells and monocytes, while DC plasmacytoids (DCps) express only TLR7 and immature DCs (DC11c$^+$) express only TLR8. R848 treatment of PBMCs induced TNF-α secretion, which was reversed by CU-CPT8m, but not by compound 4a, in a dose-dependent manner (FIG. 4F). Notably, the TNF-α level was not reduced to baseline by CU-CPT8m, presumably because both TLR7 and TLR8 were activated by R848.

Example 3: High-Resolution Crystal Structure of the CU-CPT8m-TLR8 Complex

Previously, two ligand-binding sites have been identified for TLR7 and TLR8. In TLR8, Site 1 is the binding site for the RNA degradant uridine and tricyclic imidazoquinoline ligands such as R848 and CL097, whereas Site 2 is bound by the dinucleotide UG (Cheng, K., et al. J. Am. Chem. Soc.

Figure 6:
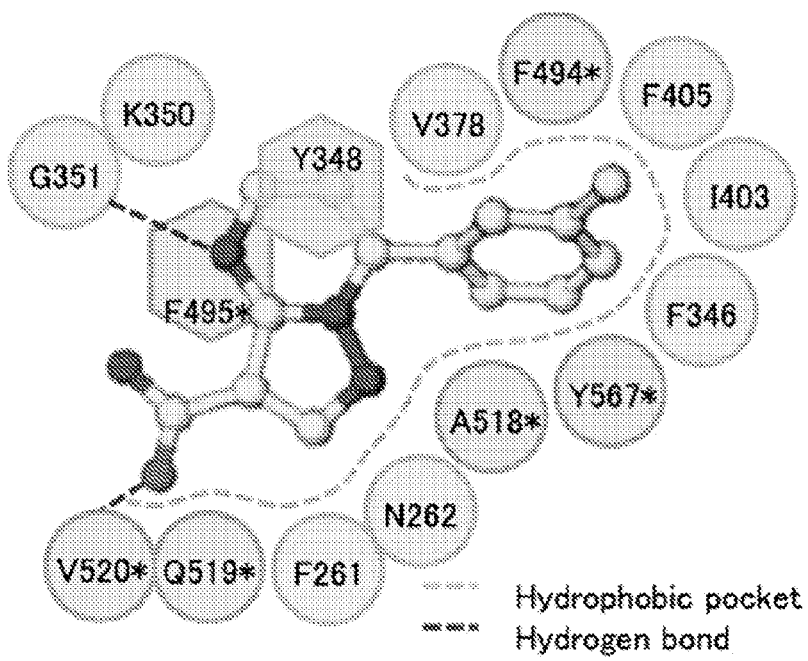
FIG. 6 shows a schematic representation of interactions between CU-CPT8m and the TLR8 protein. The hydrophobic pocket and hydrogen bonds are shown as dashed gray arcs and dashed red lines, respectively.

133:3764-67 (2011); Hennessy, E. J., et al., Nat. Rev. Drug Discov. 9:293-307 (2010)). The inventors determined the high-resolution X-ray crystal structure of the TLR8/CU-CPT8m complex. Interestingly, the crystal structure showed that CU-CPT8m is sandwiched between two protomers (TLR8 and TLR8*, throughout this disclosure, asterisks are used to indicate the second TLR8 and its residues) and is accommodated in a hydrophobic pocket on the protein-protein interface of TLR8 and TLR8*. This pocket is only formed in the preformed dimer in the resting state, and is partially filled with several water molecules in the unliganded form. CU-CPT8m forms several interactions with TLR8; van der Waals interactions with hydrophobic residues (F261, F346, V378, I403, F405, F494*, A518*, V520*, and Y567*), π-π stacking with Y348 and F495*, and hydrogen bonds with G351 and V520* (FIG. 6). Upon CU-CPT8m binding, large conformational changes of the loop regions of leucine-rich repeat (LRR) 8 (F261 and N262) and LRR18 (Y567*) are induced to interact with CU-CPT8m, while the other regions are not significantly changed. Note that TLR8 utilizes LRR11-13 for both agonist and antagonist binding on one side of the interface, while on the other side LRR17*-18* and LRR15*-16* are used for agonist and antagonist binding, respectively. Therefore, this new binding site is close to but distinct from Site 1 previously identified for the agonist, implying a unique inhibitory mechanism for compound CU-CPT8m. Additionally, the superimposition of antagonistic binding sites of TLR7 and TLR8 reveals structural difference, which may explain why inhibitory activity of CU-CPT8m specifically targets TLR8 but not TLR7.

Upon ligand-induced activation, the ectodomains of TLR8 undergo conformational changes, resulting in less separation of their C-termini. The distances between the C-termini of the two protomers of TLR8 dimer are 49 Å in TLR8/CU-CPT8m and 51 Å in unliganded TLR8 dimer (PDB ID: 3W3G), respectively. These values are obviously larger than that of agonist-bound activated dimer (34 Å; TLR8/R848, PDB ID: 3W3N), in which the two C-termini come closer to allow dimerization of intracellular domains and downstream signaling. Taken together, these data indicate that CU-CPT8m recognizes a novel binding site on the TLR8-TLR8* interface, distinct from Site 1, whose occupation prevents TLR8 activation.

Example 4: Inhibitors Stabilize TLR8 in Resting State by Recognizing Unique Binding Site Despite being potent and selective for TLR8, the existence of the unutilized residues (e.g. S516 and Q519) in the binding pocket suggests that it is possible to further optimize the binding affinity of CU-CPT8m. Therefore, we started another SAR study of 4-phenyl-1-(2H)-phthalazinone, the second, distinct scaffold identified from the HTS, as an alternative seed structure. The structural optimization led to two new, approx. pM, TLR8 inhibitors that are structurally similar to CU-CPT8m: CU-CPT9a (IC$_{50}$=0.5±0.1 nM) and CU-CPT9b (IC$_{50}$=0.7 0.2 nM). Representative structure-activity relationship (SAR) results for inhibitory activities of quinoline derivatives in HEK-Blue hTLR8 cells follows:

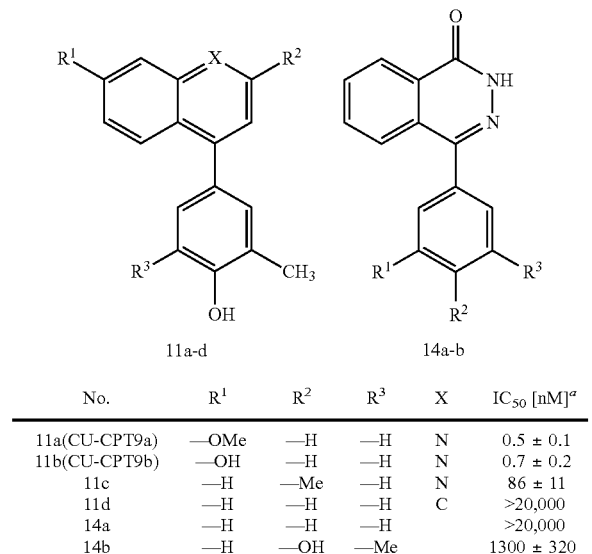

| No. | R$^1$ | R$^2$ | R$^3$ | X | IC$_{50}$ [nM]$^a$ |
|---|---|---|---|---|---|
| 11a(CU-CPT9a) | —OMe | —H | —H | N | 0.5 ± 0.1 |
| 11b(CU-CPT9b) | —OH | —H | —H | N | 0.7 ± 0.2 |
| 11c | —H | —Me | —H | N | 86 ± 11 |
| 11d | —H | —H | —H | C | >20,000 |
| 14a | —H | —H | —H | | >20,000 |
| 14b | —H | —OH | —Me | | 1300 ± 320 |

$^a$IC$_{50}$ values and corresponding standard deviations were determined from at least three biological replicates.

Replacing the phthalazinone with a quinoline motif dramatically increased the inhibitor potency. The nitrogen atom in quinoline motif may play a critical role in binding to TLR8 as its removal significantly decreased the potency (11c vs 11d). Methoxyl (11a) or hydroxyl (11b) substitution at the 7-positon also showed a significant improvement of inhibitory potency.

Because SARs starting with distinct seeds led to a similar scaffold suggesting that such a scaffold is nearly optimal. Accordingly, ITC experiments confirmed the strong binding of CU-CPT9b with a K$_d$ of 21 nM. These compounds have demonstrated excellent potency in blocking TLR8 activation induced by either R848 or ssRNA (FIGS. 7A-7D) with negligible effects in wild type HEK 293 cells or HEK-Blue 293 cells expressing other TLRs.

Figure 8A:
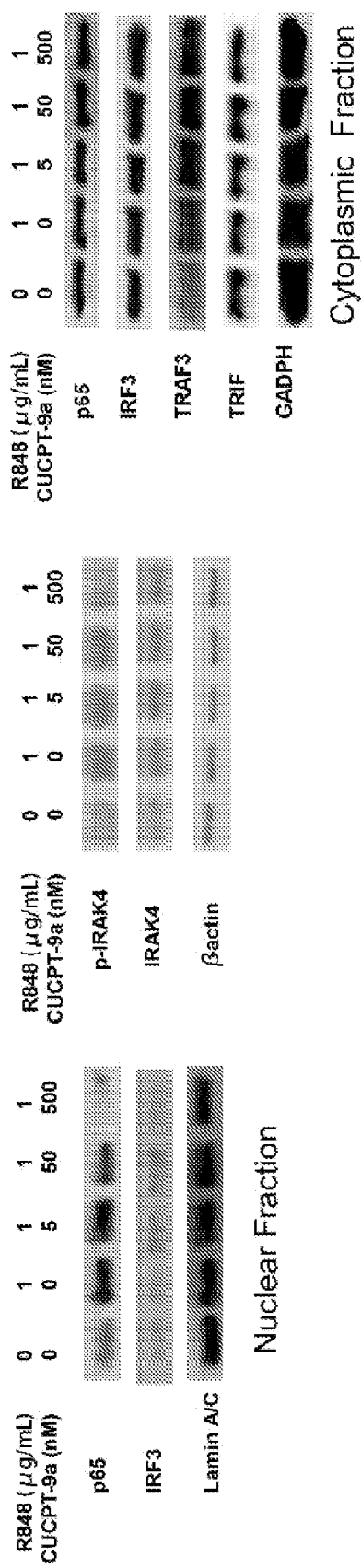
FIGS. 8A and 8B show the effects of CU-CPT9a on selected TLR downstream signaling pathway protein expression levels.
Figure 8B:
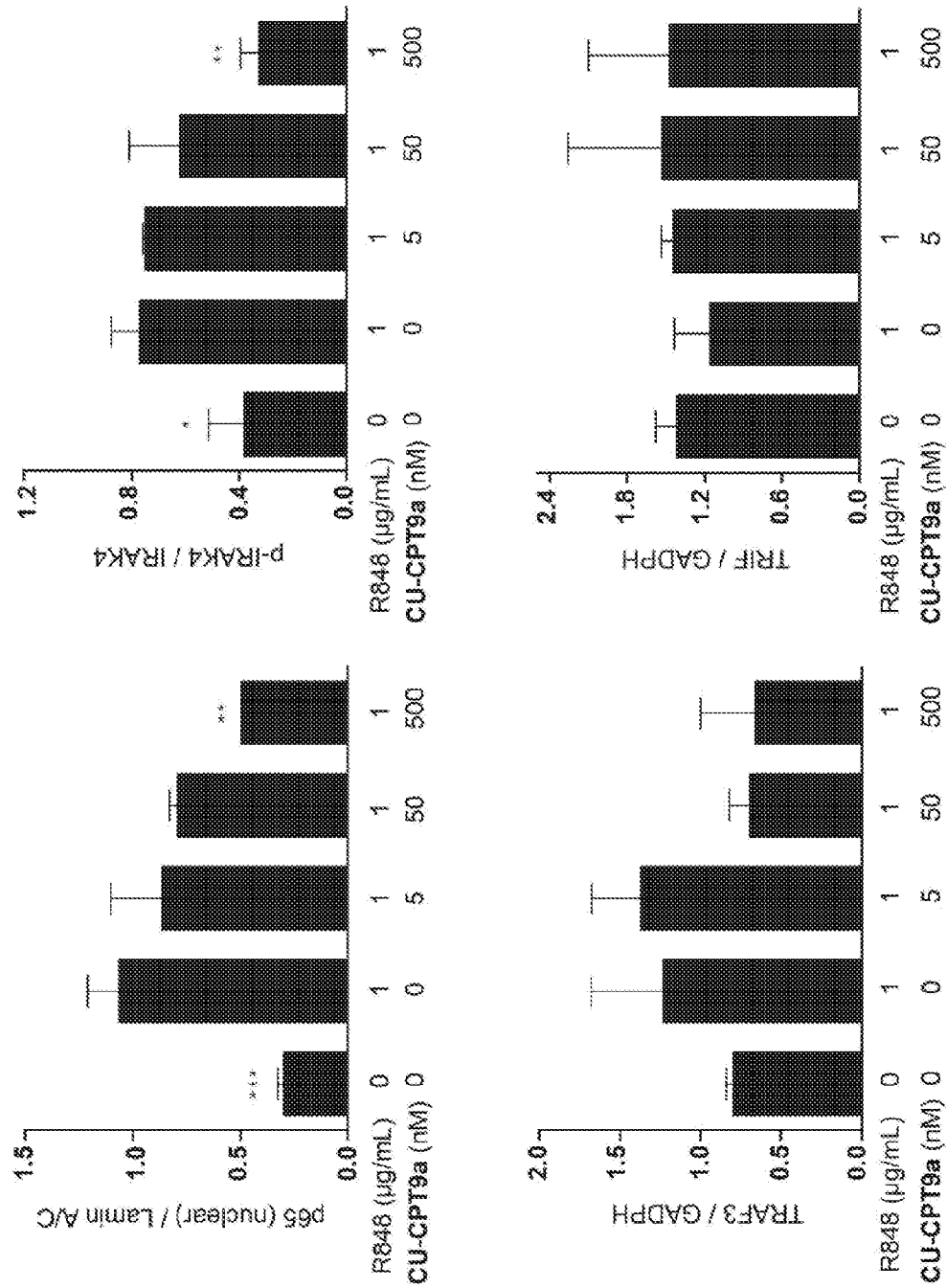

Next, the inventors carried out on-target validation for CU-CPT9a. The downstream protein levels were determined using immunoblot analysis in cells treated with R848 in the presence or absence of CU-CPT9a (FIGS. 8A and 8B). The p65 component of NF-κB, phosphorylated IRAK-4 (p-IRAK4), and TRAF3, all downstream to TLR8, showed elevation upon R848 treatment in both THP-1 and HEK-Blue TLR8 cells (data not shown). This elevation of the downstream protein levels induced by R848 can be reversed by CU-CPT9a in a dose-dependent manner. By contrast, the expression of TRIF and IRF3 (cytoplasmic and nuclear) were only responsive to TLR4 and TLR3, independent of TLR8. The expression levels of TRIF and IRF3 did not show significant change in THP-1 cells upon treatment of R848, nor do they change with the treatment of CU-CPT9a. Taken together, these immunoblot analyses suggest that the inhibitory effects of CU-CPT9a in cells occurs specifically through TLR8.

Figure 9A:
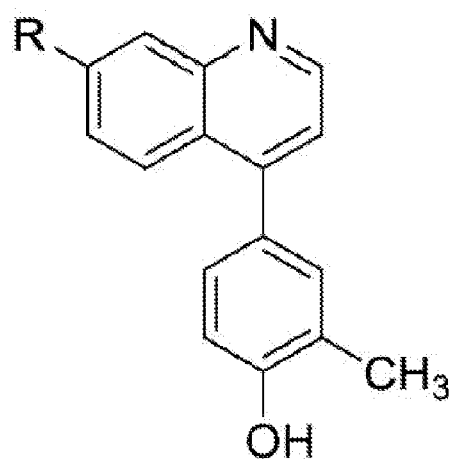
FIGS. 9A and 9B shows TLR8 inhibitors consistently recognize an allosteric pocket on the protein-protein interface, stabilizing the inactive TLR8 dimer.
Figure 9B:
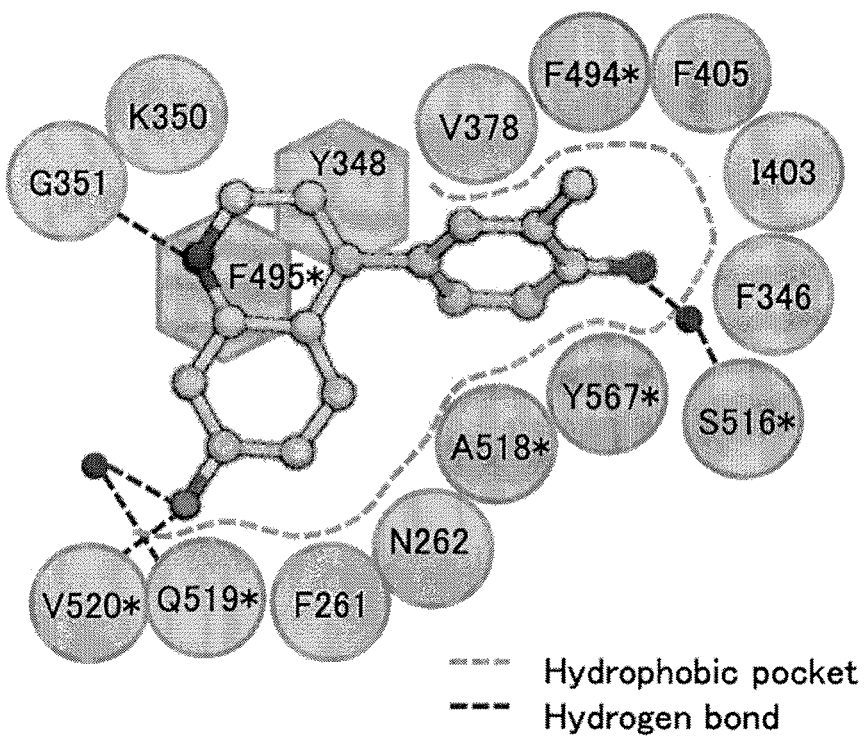

To further explore the molecular mechanism of inhibition, the inventors obtained the crystal structure of the TLR8/CU-CPT9b complex, which showed that CU-CPT9b binds to the inactive TLR8 dimer in a similar way to CU-CPT8m. CU-CPT9b hydrogen bonds with G351 and V520*, which are conserved among TLR8/antagonist structures (FIGS. 9A and 9B). Additionally, CU-CPT9b forms water-mediated contacts with S516* and Q519*, which are not observed in the TLR8/CU-CPT8m structure, suggesting that the enhanced potency of CU-CPT9b derives from the new interactions with these polar residues. The orientation of Y567* also changes to facilitate van der Waals interactions with CU-CPT9b as compared to TLR8/CU-CPT8m.

Figure 10A:
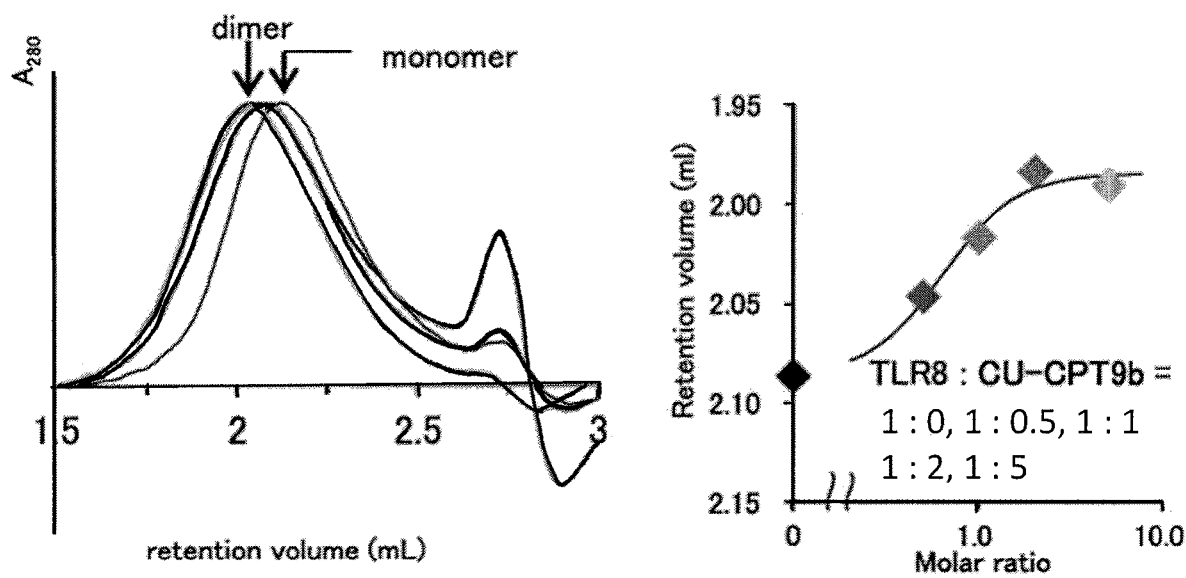
FIGS. 10A and 10B shows the dose dependent dimerization of TLR8. Elution profiles of gel filtration chromatography of TLR8 with CU-CPT9b (FIG. 10A) and R848 (FIG. 10B) at various concentrations. For each figure, retention volume and normalized absorbance at 280 nm ($A_{280}$) are shown on the left, and retention volume of TLR8 peak is plotted against its molar ratio (ligand/TLR8) on the right.
Figure 10B:
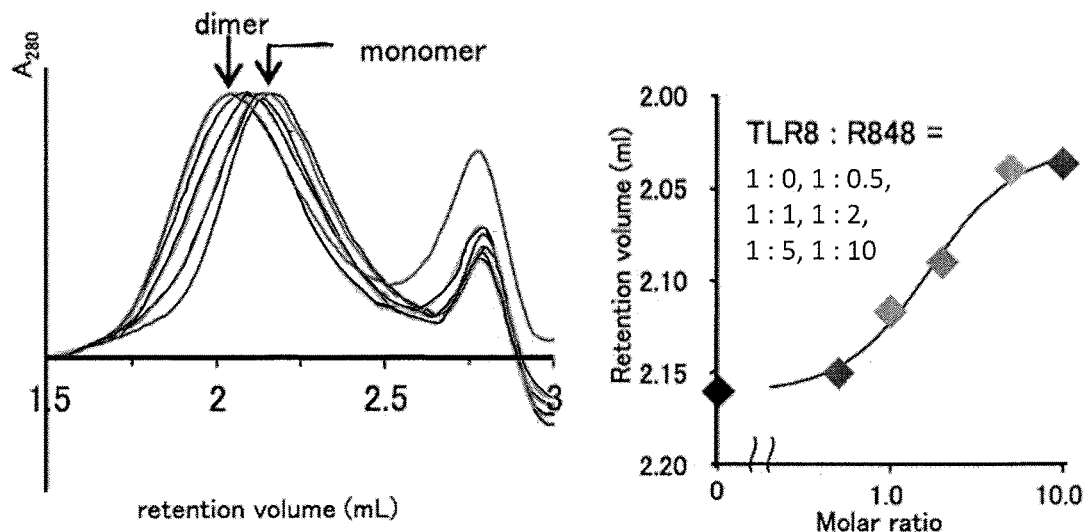

Gel filtration chromatography with diluted TLR8 proteins, in which TLR8 exists as a monomer, was conducted to determine the dimerization state of TLR8 in the absence and presence of different ligands (FIGS. 10A and 10B). TLR8 with R848 or CU-CPT9b was shown to elute at a smaller retention volume, suggesting these ligands bind to TLR8 in a dose-dependent manner and stabilize the TLR8 dimer in solution. Furthermore, the binding of these CU-CPT derivatives prevented further agonist binding, which was confirmed by ITC.

Collective evidence from CU-CPT8m, CU-CPT9a, and CU-CPT9b demonstrate this new class of inhibitor binds to TLR8 at a different site from other known small molecule agonists (e.g. uridine, R848). The inventors therefore propose the following mechanism of these TLR8 inhibitors: upon agonist binding (e.g. R848, uridine with ssRNA), two TLR8 protomers are brought closer to initiate downstream signaling. Binding of the antagonist at the new unique site stabilizes the TLR8 dimer in its resting state, preventing TLR8 activation.

Figure 11A:
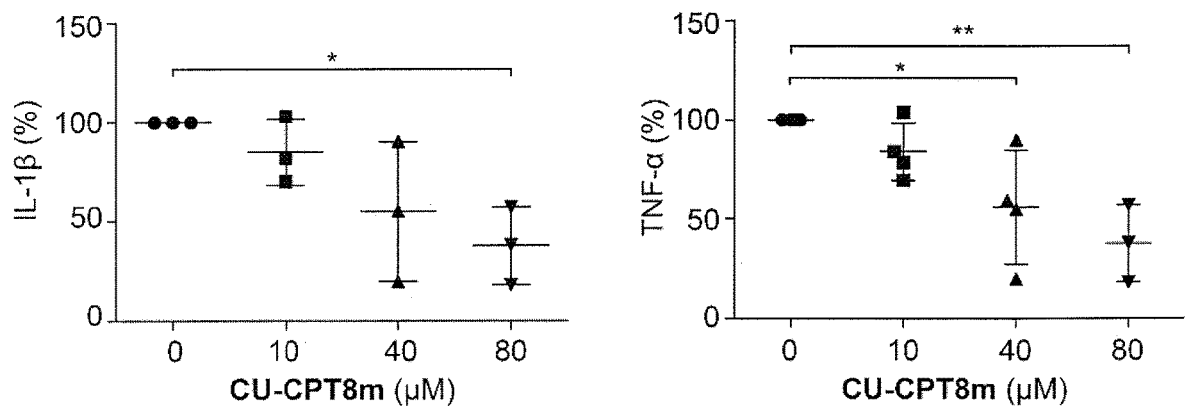
FIGS. 11A and 11B show that TLR8 inhibitors suppress the proinflammatory cytokine production in multiple human primary cells derived from different patients.
Figure 11B:
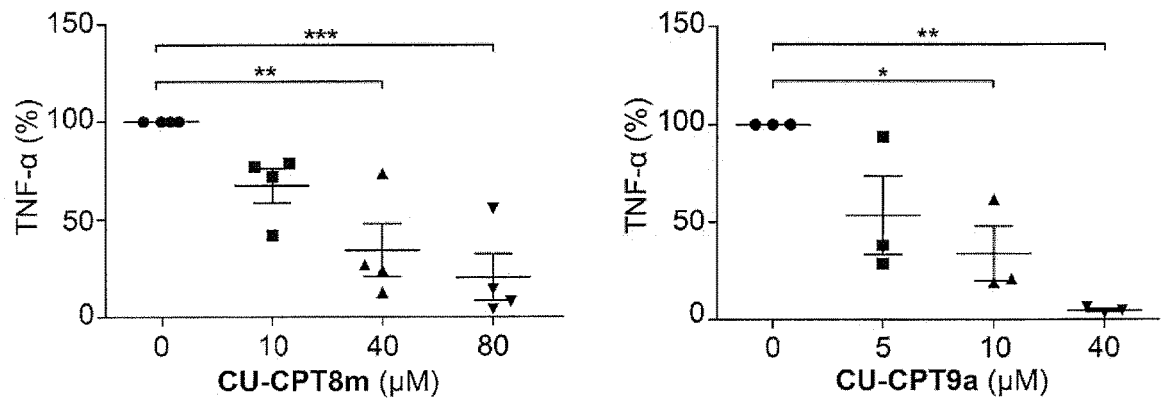
Figure 12:
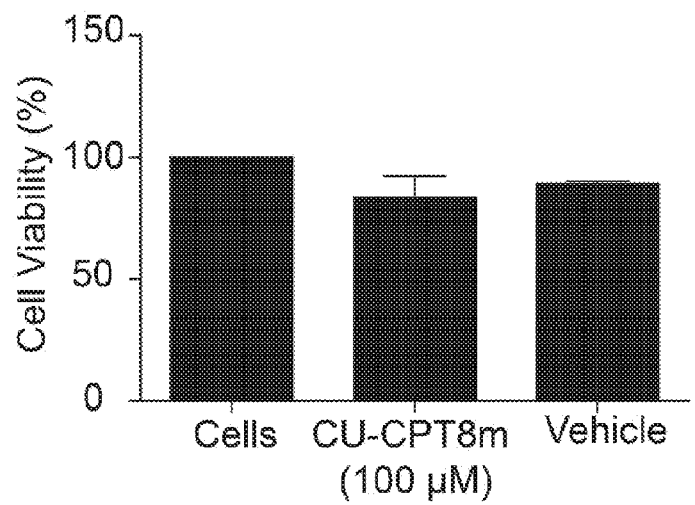
FIG. 12 shows the cytotoxicity of CU-CPT8m on synovial cells. CU-CPT8m showed little cytotoxicity at concentrations up to 100 μM in synovial cells isolated from osteoarthritis (OA) patients. Results shown as mean s.e.m. The data was determined in duplicate.
Figure 13:
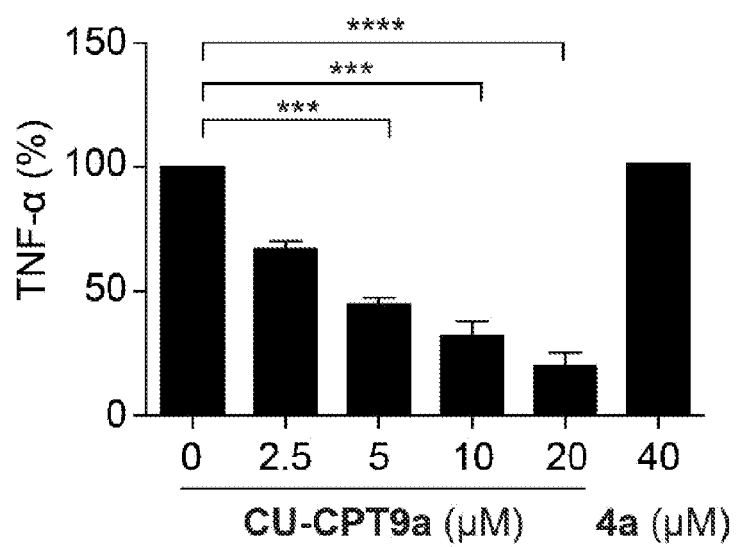
FIG. 13 shows the dose-dependent suppression of the TNF-α level by CU-CPT9a in PBMCs harvested from an adult onset-Still's disease (AOSD) patient. Negative control compound (4a) did not show notable inhibitory activity at 40 μM. Results shown as mean s.e.m. *P<0.05; P<0.01; *P<0.001; ****P<0.0001.
Figure 14:
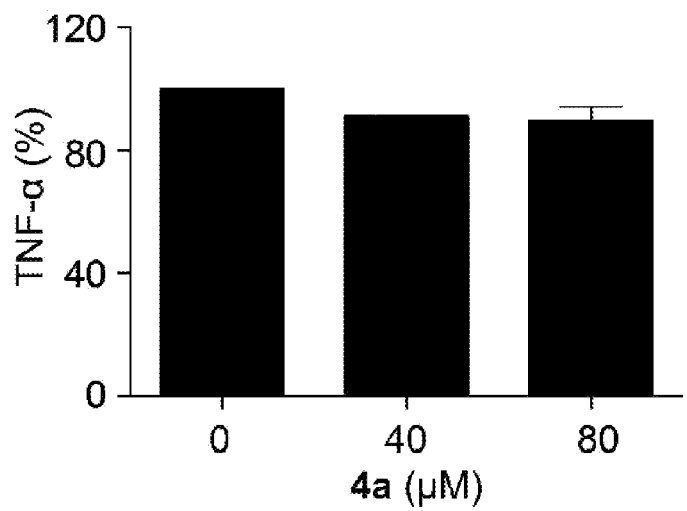
FIG. 14 shows the suppression of the TNF-α level by negative control compound (4a) in PBMCs harvested from RA patients (n=2). 4a did not show notable inhibitory activity up to 80 μM. Results shown as mean s.e.m.

Example 5: Small Molecule TLR8 Inhibitors Provide a Lead for Therapeutic Development While previous evidence suggests that TLR8 plays an important role in autoimmune disorders, the feasibility of targeting these diseases by suppressing TLR8 has not been firmly established. After identifying highly potent and selective TLR8 inhibitors, the inventors aimed to validate their therapeutic potential using a more pathologically relevant system. But there is a lack of appropriate rodent models because TLR8 is not functional in either mice or rats. Therefore, the TLR8 inhibitors of this disclosure were tested in human specimens harvested from patients with osteoarthritis (OA), rheumatoid arthritis (RA), and adult onset-Still's disease (AOSD). It is well established that TNF-α and IL-1β are key cytokines in the process of chronic joint inflammation in cartilage. Therefore, synovial cells were isolated from synovial tissue of patients who underwent joint replacement surgery due to severe OA. Previous studies have indicated these pathological tissues express both TLR7 and TLR8 with elevated production of various cytokines, contributing to extensive articular destruction and functional decline. CU-CPT8m showed significant inhibitory effects in suppressing the spontaneous release of TNF-α and IL-1β from synovial membrane cultures (FIGS. 11A and 11B) with little cytotoxicity up to 100 μM (FIG. 12). In parallel, we also tested whether CU-CPT8m and CU-CPT9a could reduce the cytokine elevation in PMBCs derived from four patients with rheumatoid arthritis (RA) and one with adult onset-Still's disease (AOSD), a rare systemic inflammatory disease characterized by the classic triad of persistent high spiking fevers, joint pain, and a distinctive salmon-colored bumpy rash. CU-CPT8m and CU-CPT9a both significantly suppressed the TNF-α level in a dose-dependent manner (FIGS. 11B, 13), which is in agreement with previous reports of TLR8 involvement in these autoimmune diseases. The negative control compound 4a did not show significant inhibition up to 80 μM (FIG. 14). Although the inhibition of cytokine production by these inhibitors does not necessarily indicate a role for TLR8 in the pathogenesis of these diseases, our results suggest a novel potential therapeutic development strategy for patients' symptom relief.

Figure 15A:
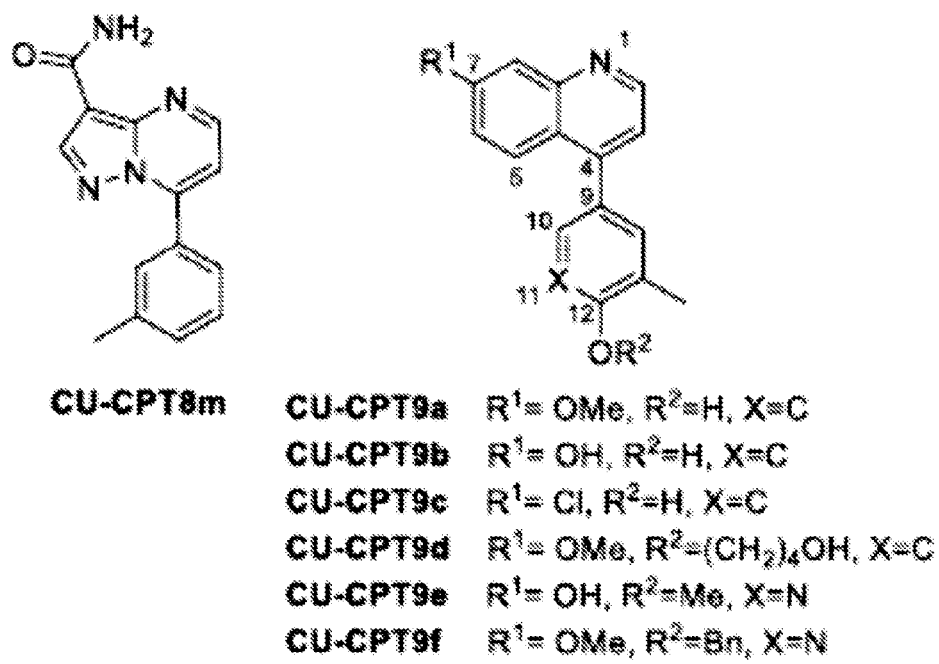
FIG. 15A shows the chemical structures of compounds CU-CPT8m and CU-CPT9a-9f.
Figure 19A:
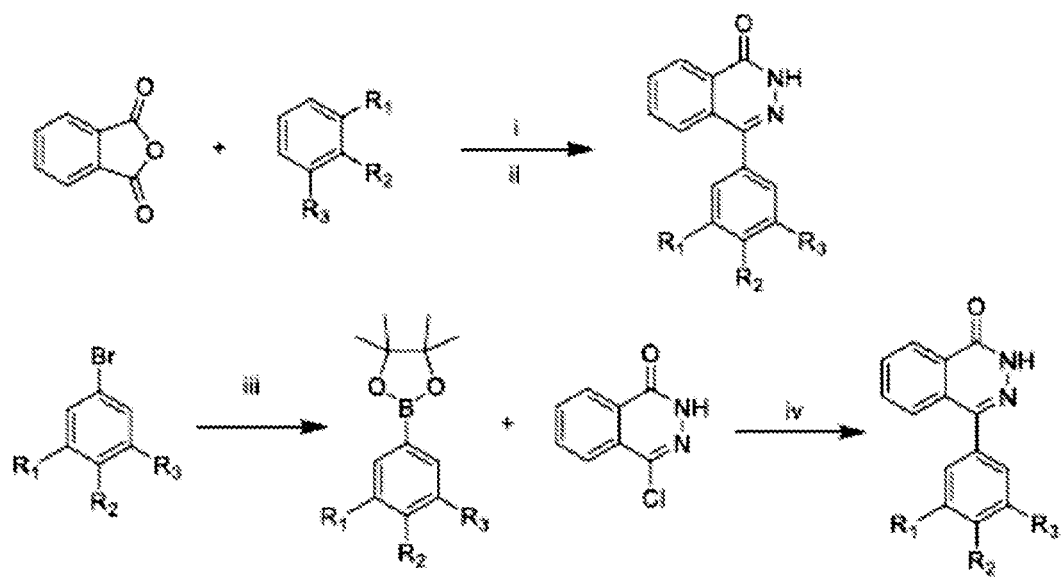
FIG. 19A shows a representative synthesis route for the phthalazinone derivatives. Reagents and conditions: (i) $AlCl_3$, dichloroethane, reflux overnight; (ii) Hydrazine, EtOH, reflux overnight; (iii) $B_2Pin_2$, KOAc, $PdCl_2$dppf-$CH_2Cl_2$, 1,4-dioxane, 90° C.; (iv) $K_2CO_3$, $PdCl_2$dppf.$CH_2Cl_2$, 1,4-dioxane, $H_2O$, 90° C., overnight.
Figure 19B:
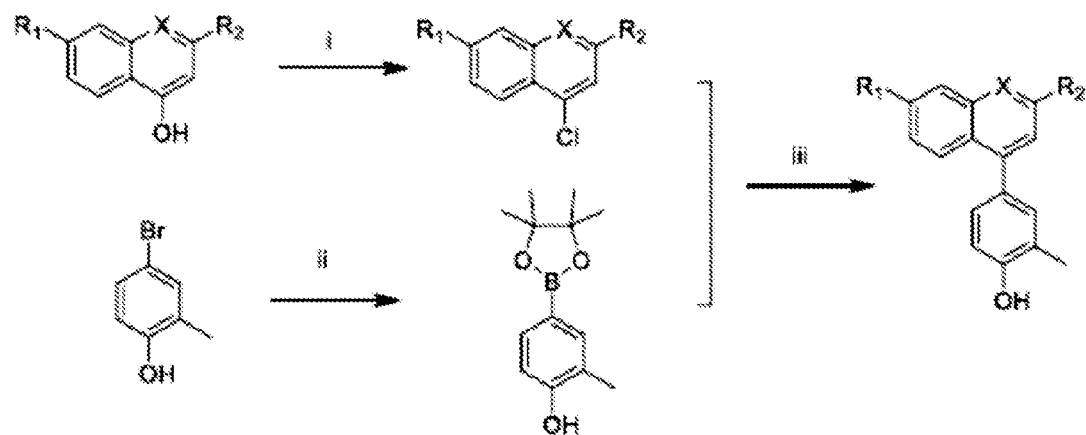
FIG. 19B shows a representative synthesis route for the quinoline derivatives. Reagents and conditions: (i) $POCl_3$, reflux overnight; (ii) $B_2Pin_2$, KOAc, $PdCl_2$dppf.$CHCl_2$, 1,4-dioxane, 90° C., overnight; (iii) $K_2CO_3$, $PdCl_2$dppf-$CH_2Cl_2$, 1,4-dioxane, $H_2O$, 90° C., overnight.

Example 6: Structure-Based Rational Design of Exceptionally Potent TLR8 Inhibitors The inventors set out to optimize the TLR8 inhibitors by installing new functionalities, aiming to further utilize additional interactions with residues at the newly identified binding site on the TLR8 dimeric interface. Multiple synthetic routes were developed to prepare structurally comparable chemical scaffolds (FIGS. 19A, 19B). More than 100 different compounds were synthesized to demonstrate a consistent structure-activity relationship. In particular, to utilize the hydrogen bond with G351, a variety of heterocycles were synthesized. The quinoline core yielded the most potent inhibitors as shown in FIG. 15A and the following table:

Structure-Activity Relationship Results for Inhibitory Activities of 1(2H)-Phthalazinone and Quinoline Derivatives in HEK-Blue hTLR8 Cells.

| Name | $R^1$ | $R^2$ | $R^3$ | $R^4$ | $R^5$ | $IC_{50}$ (μM) |
|---|---|---|---|---|---|---|
| 1 | —OMe | | | | | 7.03 ± 0.36 |
| 2 | —OH | | | | | 0.48 ± 0.43 |
| 3 | —$NH_2$ | | | | | 2.72 ± 0.31 |
| 4 | —Me | —OH | —Me | —H | —Me | 0.17 ± 0.02 |

-continued
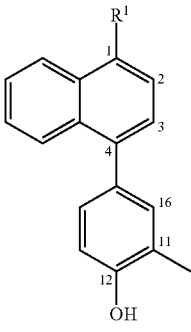
| Name | R¹ | R² | R³ | R⁴ | R⁵ | IC$_{50}$ (μM) |
|---|---|---|---|---|---|---|
| 5 | —H | —H | —H | —H | —H | >20 |
| 6 | —H | —H | —H | —H | —Me | >20 |
| 7 | —Me | —H | —H | —Me | —H | >20 |
| 8 | —Me | —H | —Me | —H | —H | >20 |
| 9 | —H | —OMe | —H | —H | —H | >20 |
| 10 | —H | —OMe | —H | —H | —Me | >20 |
| 11 | —Me | —OMe | —Me | —H | —H | >20 |
| 12 | —Me | —OCF$_3$ | —Me | —H | —H | >20 |
| 13 | —Me | —COOH | —Me | —H | —H | >20 |
| 14 | —Me | —COOH | —H | —H | —H | >20 |
| 15 | —Me | —NH$_2$ | —Me | —H | —H | >20 |
| 16 | —Me | —COOMe | —H | —H | —H | 8.51 ± 3.15 |
| 17 | —Me | —OCOCH$_3$ | —Me | —H | —H | 4.76 ± 0.42 |
| 18 | —Me | —OCOCH$_3$ | —H | —H | —H | 3.77 ± 0.45 |
| 19 | —H | —OH | —H | —H | —H | >20 |
| 20 | —Me | —OH | —Me | —H | —H | 3.91 ± 0.20 |
| 21 | —Me | —OH | —H | —H | —H | 1.30 ± 0.32 |
| 22 | —CH$_2$CH$_3$ | —OH | —H | —H | —H | 2.73 ± 0.85 |
| 23 | —iPr | —OH | —iPr | —H | —H | >20 |
| 24 | —Me | —OH | —Me | —Me | —H | >20 |
| 25 | | | | | —H | >20 |
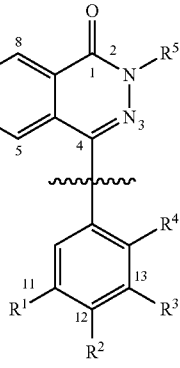
| | | | | | | |
|---|---|---|---|---|---|---|
| 26 | —CF$_3$ | —OH | —H | —H | —H | >20 |
| 27 | —CF$_3$ | —OMe | —H | —H | —H | >20 |
| 28 | —CN | —OH | —H | —H | —H | >20 |
| 29 | —NO$_2$ | —OMe | —H | —H | —H | >20 |
| 30 | —Me | —OH | —H | —H | —Me | 0.33 ± 0.04 |
| 31 | —Me | —OH | —H | —H | —Et | >20 |
| 32 | —Me | —OEt | —H | —H | —Et | >20 |
| 33 | —H | —H | —H | —H | —Ph | >20 |
| 34 | —Me | —H | —H | —H | | >20 |
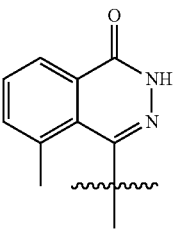

-continued
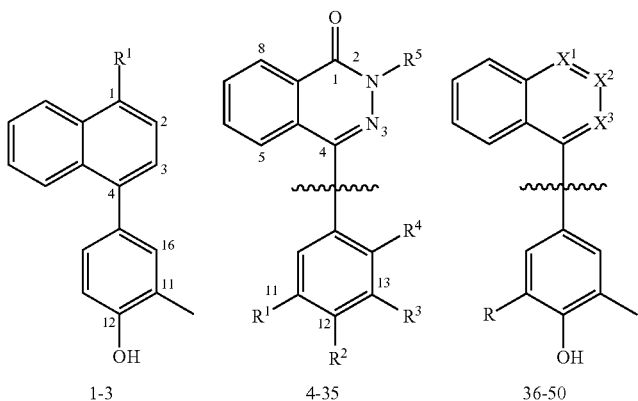
1-3, 4-35, 36-50
| Name | R¹ | R² | R³ | R⁴ | R⁵ | IC$_{50}$ (μM) |
|---|---|---|---|---|---|---|
| 35 | —Me | —H | —Me | —H | (pyrido-phthalazinone) | 13.04 ± 2.14 |
| 36 | —Me | —N | —C | —C | | 25.5 ± 10.7 (nM) |
| 37 | —H | —N | —C | —C | | 38.6 ± 5.75 (nM) |
| 38 | —H | —N | —C | —N | | 0.35 ± 0.12 |
| 39 | —H | —C | —N | —C | | 0.16 ± 0.02 |
| 40 | —Me | —C | —N | —N | | 11.42 ± 0.36 |
| 41 | —H | —C | —N | —N | | 6.75 ± 1.30 |
| 42 | —Me | —C | —C | —C | | 1.22 ± 0.10 |
| 43 | —H | —C | —C | —C | | >20 |
| 44 | —Me | —N | —N | —C | | N/A* |
| 45 | —H | —N | —N | —C | | 0.34 ± 0.02 |
| 46 | N-Boc-indol-3-yl | | | | | >20 |
| 47 | 1H-indol-3-yl | | | | | 2.80 ± 0.69 |
| 48 | 1H-indazol-3-yl | | | | | >20 |

-continued

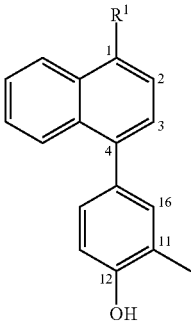

| Name | R¹ | R² | R³ | R⁴ | R⁵ | IC$_{50}$ (μM) |
|------|----|----|----|----|----|----------------|
| 49 | 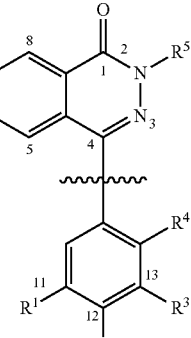 | | | | | 0.09 ± 0.03 |
| 50 | 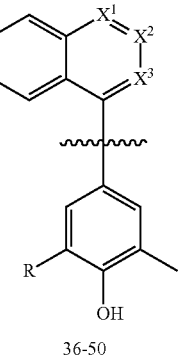 | | | | | 0.30 ± 0.07 |

*No IC$_{50}$ calculated due to cytotoxicity.

In a similar way, the installment of substituents at the 7-position was used to establish interactions with V520* and Q519*. Next, a hydroxyl group was introduced at the 12-position to explore extra contacts with S516* through a potential H-bond. These modifications resulted in several extremely potent compounds (FIG. 15A) with subnanomolar IC$_{50}$ values (compounds CU-CPT9a-9c, with IC$_{50}$ of 0.5±0.1 nM, 0.7±0.2 nM and 1.0±0.2 nM, respectively). Given that the binding of CU-CPT8m is primarily driven by size and shape complementarity, larger substitutes on the quinoline and phenol backbones mostly compromised its inhibitory effect. However, the relatively open space on the bottom of the hydrophobic pocket recognized by CU-CPT8m suggested the possibility to engineer additional intermolecular contacts. Thus, installment of long-chain substituents at 12-position was applied, which yielded several extremely potent inhibitors (FIG. 15A). In particular, compounds CU-CPT9d and 9f showed IC$_{50}$ values of 0.1±0.02 nM and 0.8±0.2 nM, respectively. This increased inhibitory effect suggested possible additional hydrophobic interactions with TLR8.

Figure 7A:
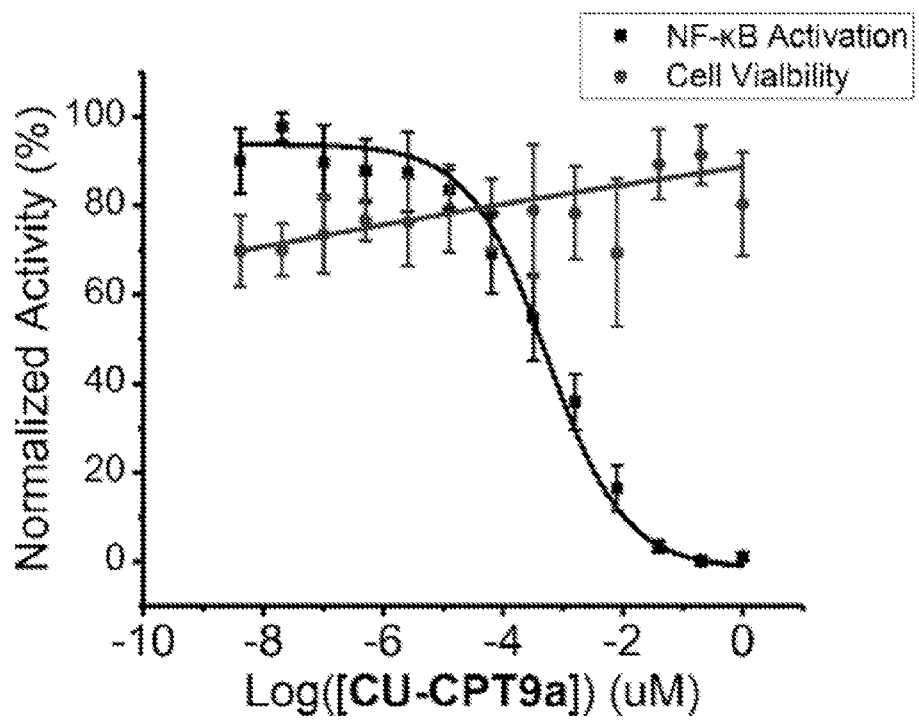
FIGS. 7A-7D show cellular activities of CU-CPT9a and CU-CPT9b.
Figure 7B:
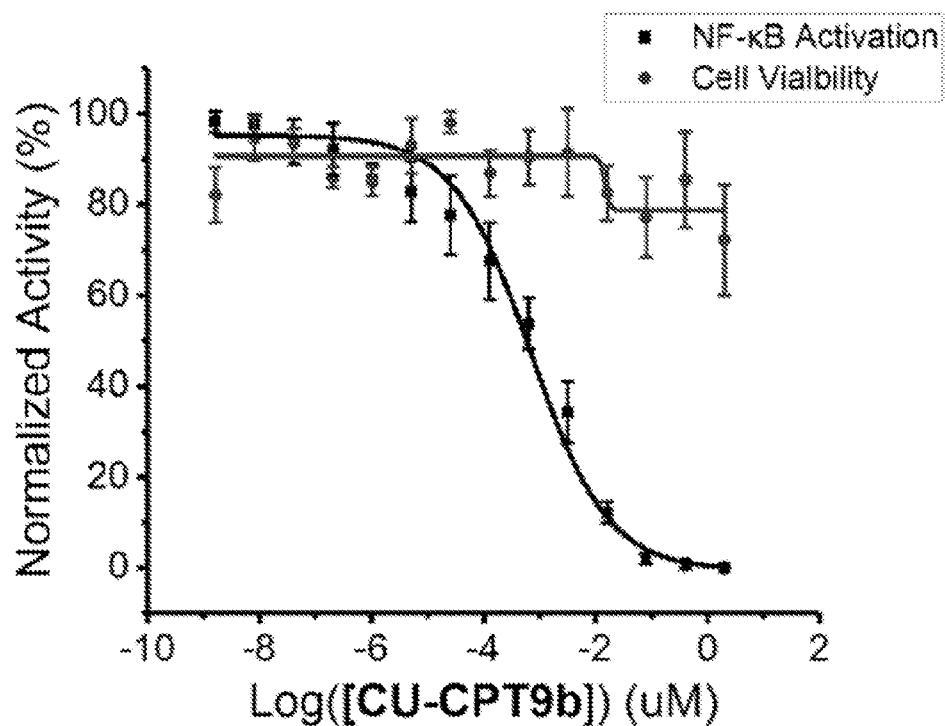
Figure 7C:
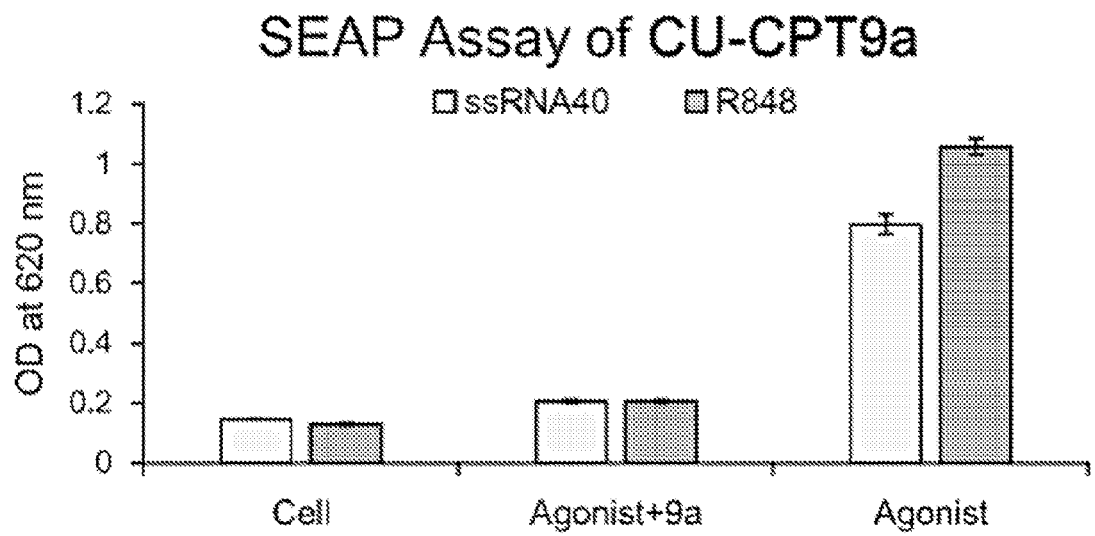
Figure 7D:
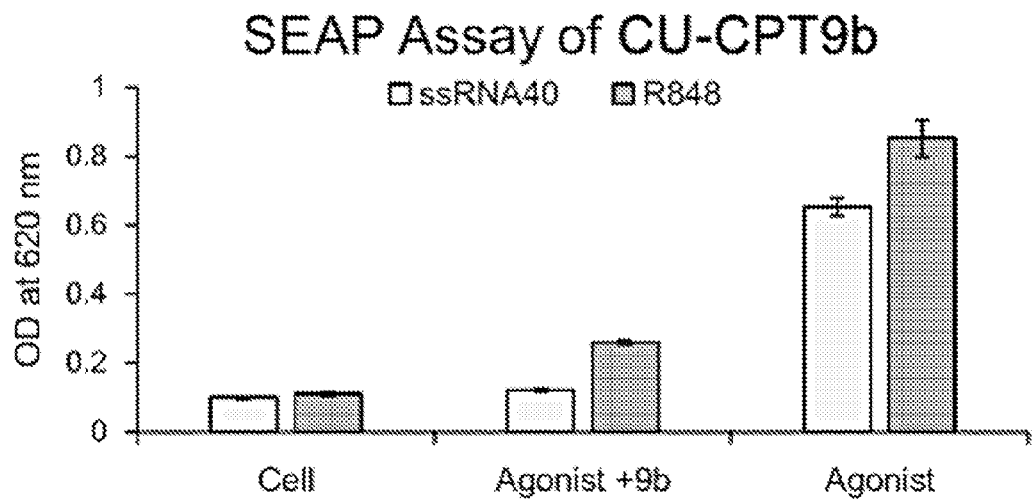
Figure 15B:
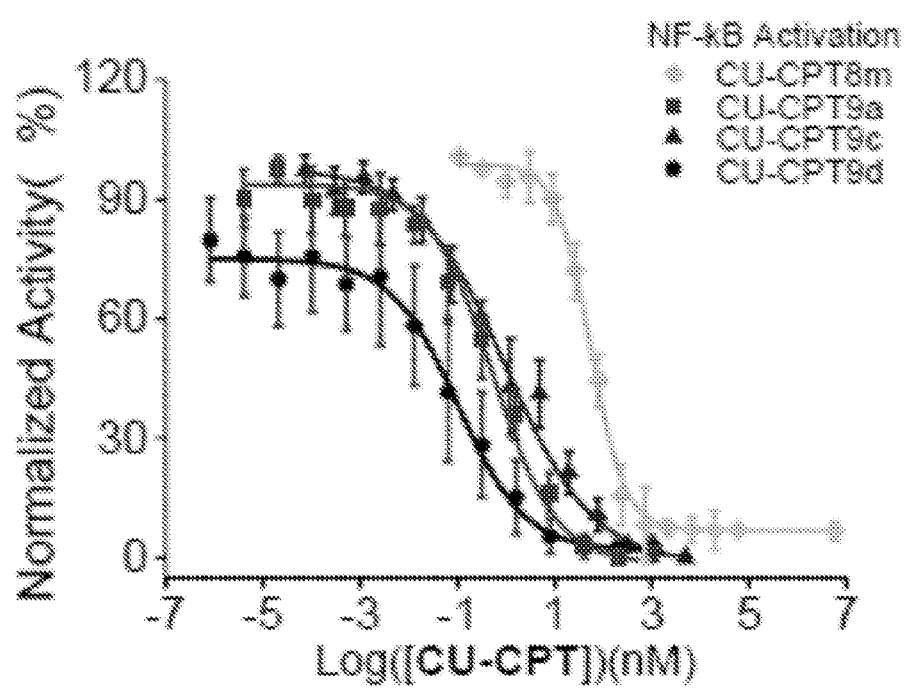
FIG. 15B shows the dose-dependent inhibitory effects of TLR8 signaling by compounds CU-CPT8m, CU-CPT9a, CU-CPT9c, and CU-CPT9d in hTLR8 HEK-Blue cell using R848 (1 g/mL) as agonist (data are mean SD; n=3 independent experiments).

Taken together, six approx. pM inhibitors (designated CU-CPT9a-9f) were identified with IC$_{50}$ values as low as 0.1±0.02 nM (FIGS. 15A, 15B) in blocking TLR8 signaling induced by its synthetic agonist, R848. Moreover, they also showed comparable inhibitory effects toward single-stranded RNA, the native ligand of TLR8 (FIGS. 7C, 7D). Isothermal titration calorimetry (ITC) confirmed the direct binding between CU-CPT9b and the ectodomain of human TLR8 with a dissociation constant (K$_d$) of 21 nM. As a comparison, the K$_d$ between TLR8 and R848 was determined as 200 nM, highlighting the superior affinity of CU-CPT9b. ITC results also showed that binding of CU-CPT9 derivatives prevented further binding of R848, supporting the design of targeting an allosteric, competitive binding site. The anti-inflammatory effect of CU-CPTs was further confirmed with the down-regulation of NF-κB, a key downstream target for TLR8 signaling. CU-CPT9a showed significant reduction of nuclear NF-κB at concentration of 500 nM. Finally, these compounds all demonstrated minimal cytotoxicity, suggesting promising potential for further therapeutic development (FIGS. 8A, 8B).

Figure 16A:
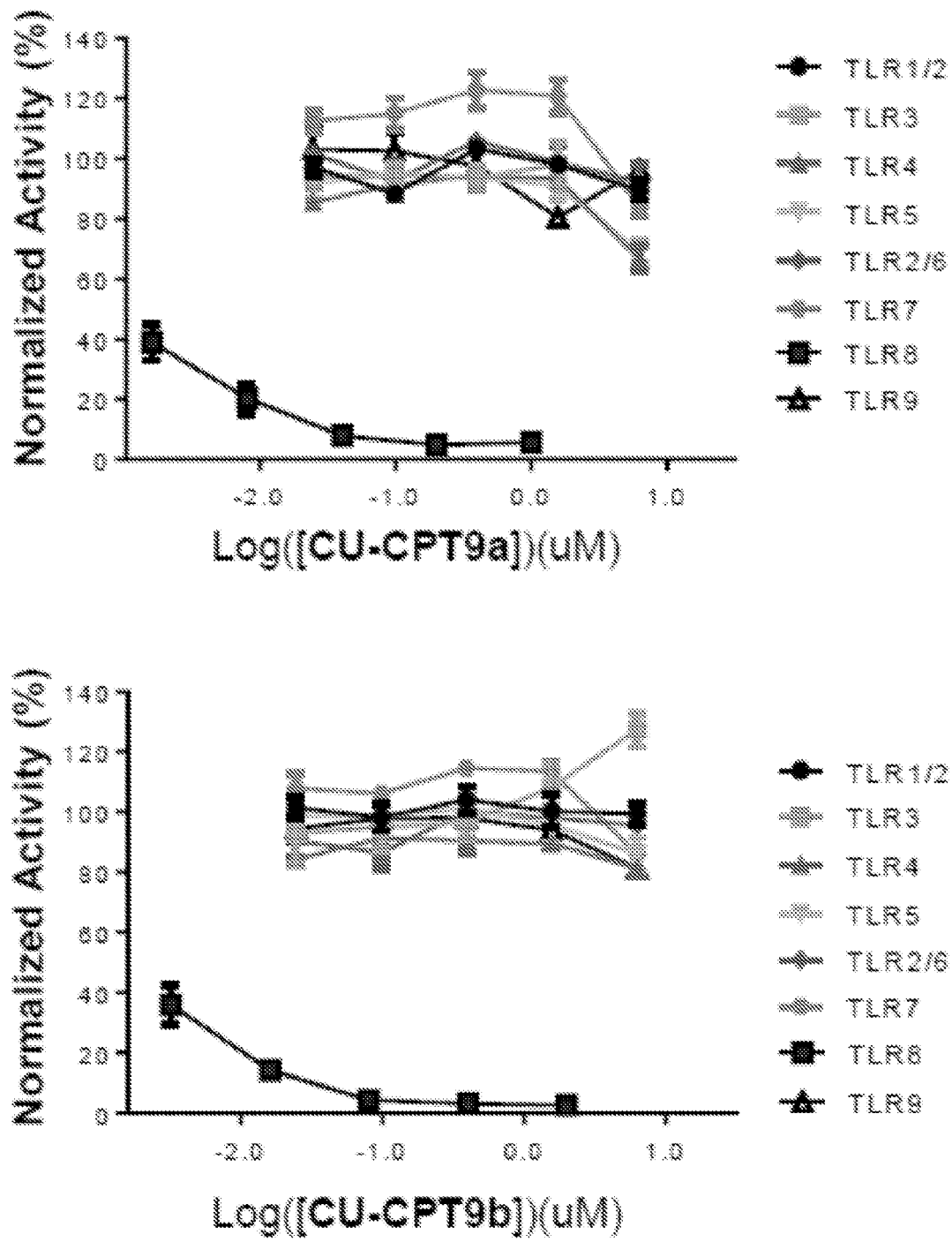
FIGS. 16A and 16B shows specificity tests of CU-CPT compounds.
Figure 16B:
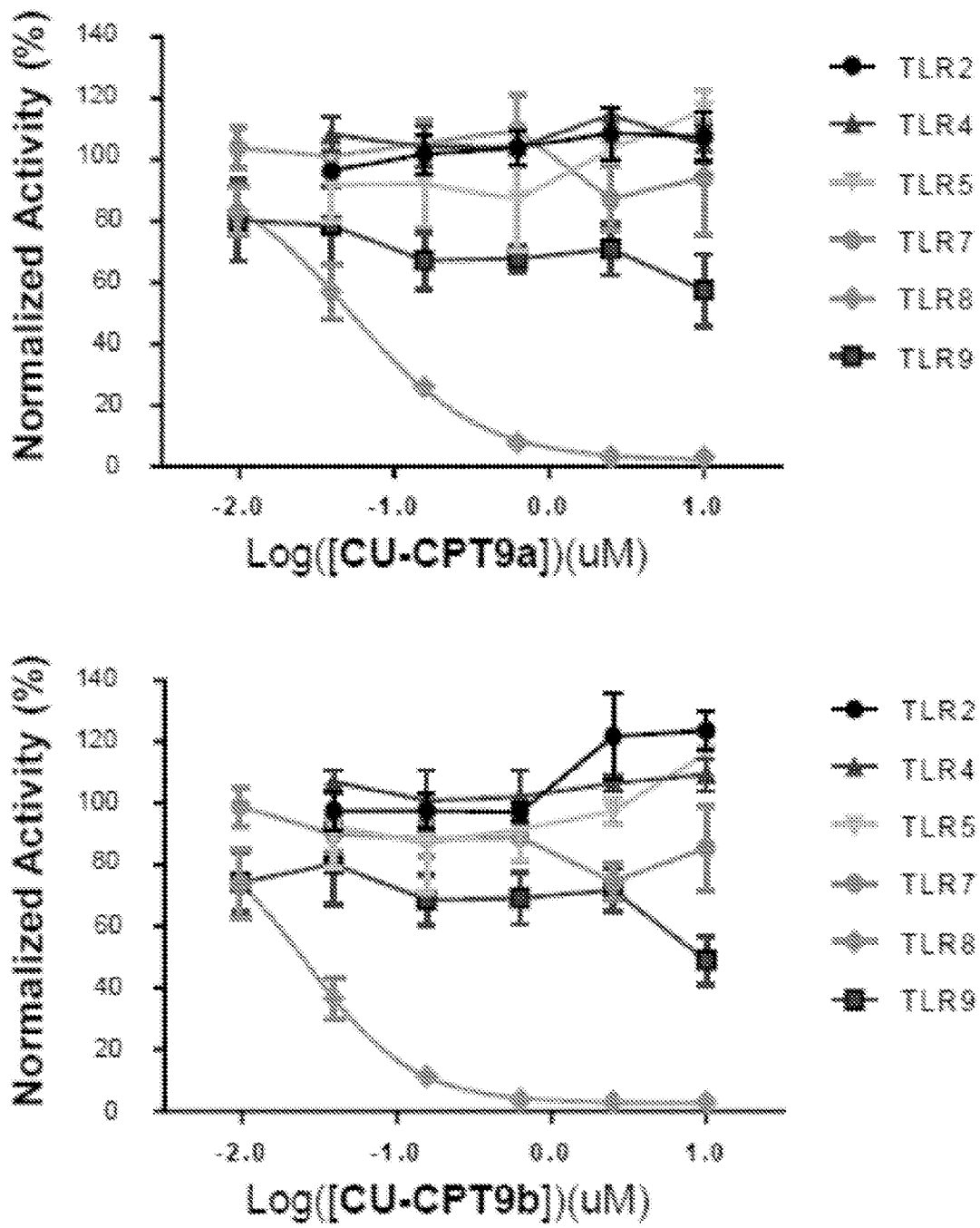

A major challenge in developing TLR inhibitors is to achieve selectivity among the highly analogous TLR family proteins. This is especially true for TLR7 and TLR8 because they both recognize single-stranded RNA as well as non-selective small-molecule agonists (e.g. R848). The specificity of compounds CU-CPT9a and CU-CPT9b was tested using HEK-Blue cells individually overexpressing each human TLR. CU-CPT9a and CU-CPT9b showed good selectivity towards TLR8 over other TLRs (FIG. 16A). In particular, TLR7 was not affected below approx. micromolar concentration, showing more than 10,000 fold difference in selectivity. The specificity of CU-CPT9s against human TLRs was also tested using PBMCs and their subsets that express multiple TLRs. In these cells, CU-CPT9s specifically inhibited cytokine production induced by TLR8, but not by TLR2, 4, 5, 7 or 9 (FIG. 16B).

To validate our structure-based designs and the mechanism of action of these compounds, the inventors successfully solved two structures of TLR8/CU-CPT complexes, TLR8/CU-CPT9a and TLR8/9c (FIG. 17), using X-ray crystallography. In an agreement with the previously reported structure of TLR8/CU-CPT9b (FIG. 17), all CU-CPT9 series compounds recognize the allosteric pocket identified by CU-CPT8m between two TLR8 protomers, thereby stabilizing the dimer at resting state (FIG. 17, top). This hydrophobic pocket only exists in the resting state of preformed TLR8 dimer, with several water molecules filling inside. All CU-CPT9 compounds showed similar binding pattern: 7-71 stacking with Y348 and F495*, van der Waals interactions with hydrophobic residues (F261, F346, V378, I403, F405, F494*, A518*, V520*, and Y567*), H-bonds with G351 and V520*. Also, CU-CPT9 compounds formed water mediated H-bonds with 5516*, although only weak electron density corresponding to water molecule was observed in TLR8/CU-CPT9a and 9c complexes due to their lower crystallographic resolutions. Water mediated H-bonds with Q519* was also formed in TLR8/CU-CPT9b, but not in TLR8/CU-CPT9a/9c because of the hindrance of 7-methoxyl group and chlorine atom. The results of co-crystal structures are in accordance with our SAR study and confirmed our rational design: quinoline motif showed optimal inhibition for its 7-7 stacking with Y348 and F495* and H-bonds with G351; 7-substituents increased inhibitory effect because of their H-bonds with V520* and Q519*; 12-hydroxyl group was involved in water mediated H-bond with 5516* (FIG. 17, middle and bottom).

Figure 18A:
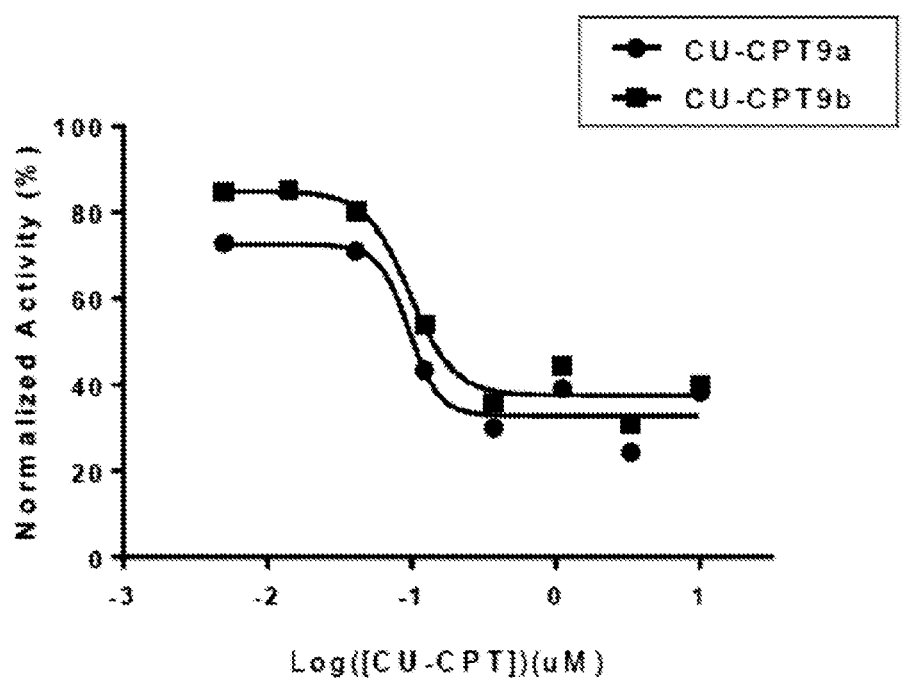
FIGS. 18A and 18B show the inhibitory effect of CU-CPT compounds in splenocytes. CU-CPT9a and CU-CPT9b demonstrated inhibition of IL-12p40 production as a monitor of TLR8 signaling (FIG. 18A) with no activity against mouse TLR9 (FIG. 18B) in the splenocytes harvested from hTLR8tg/TLR7-KO mice. ORN8L (100 ug/mL) and 1018 (7.1 ug/mL) were used as TLR8 and TLR9 agonists, respectively.
Figure 18B:
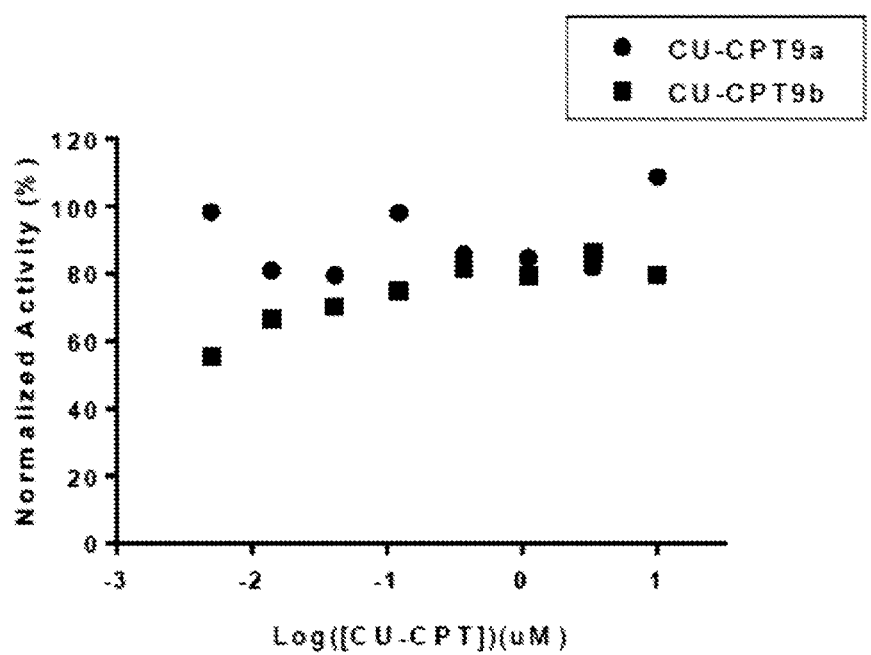

TLR8 is a potential therapeutic target for autoimmune diseases. Although previous work demonstrated the effects of TLR7 and TLR9 in autoimmunity in mice models Lau, et al. (2005) J. Exp. Med. 202, 1171-77; Leadbetter, et al., (2002) Nature 416, 603-07), a similar evaluation of TLR8 was not possible because murine TLR8 is thought to be nonfunctional (Jurk, et al., (2002) Nat. Immunol. 3, 499). Therefore, the CU-CPT9 compounds were tested on splenocytes isolated from mice harboring a human TLR8 transgene in a TLR7 knock-out background (hTLR8tg/TLR7-KO). The results from mouse splenocytes were consistent with those from human cells, CU-CPT9 compounds demonstrated antagonist activity against the human TLR8 transgene with no activity against mouse TLR9 when using ORN8L (100 ug/mL) and 1018 (7.1 ug/mL) as TLR8 and TLR9 agonists, respectively (FIGS. 18A, 18B).

General chemistry methods NMR spectra were acquired on Bruker 400 spectrometer, running at 400 MHz for 1H and 101 MHz for $^{13}$C respectively. $^1$H NMR spectra were recorded at 400 MHz in CHCl$_3$-d, (CH$_3$)$_2$SO-d$_6$ and CH$_3$OH-d$_4$ using residual CHCl$_3$, DMSO and CH$_3$OH as the internal standard. $^{13}$C NMR spectra were recorded at 101 MHz in CHCl$_3$-d, (CH$_3$)$_2$SO-d$_6$ and CH$_3$OH-d$_4$ using residual CHCl$_3$, DMSO and CH$_3$OH as the internal standard. Thin layer chromatography was performed on Merck Kieselgel 60 Å F254 plates eluting with the solvent indicated, visualized by a 254 nm UV lamp. Compounds were purified using flash chromatography, (Silica gel 60 Å, 230-400 mesh, Sorbent Tech.). Mass spectrometry was performed at the mass spectrometry facility of the Department of Chemistry at University of Colorado Boulder on a double focusing high-resolution mass spectrometer. Unless otherwise noted, analytical grade solvents and commercially available reagents were used without further purification. The purity of tested compounds was evaluated by HPLC (Agilent Technologies 1200 serials) using UV detector at 254 nm.

Synthesis

1-Bromo-4-methoxynaphthalene (96)

To a solution of 4-bromo-1-naphthol (223 mg, 1.00 mmol) in dioxane was added sodium hydride (72 mg, 3.00 mmol), then methyl iodide (75 uL, 1.20 mmol), the reaction mixture was refluxed overnight. 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give light yellow solid. (211 mg, 89%). $^1$H NMR (400 MHz, Chloroform-d) δ 8.27 (d, J=8.6 Hz, 1H), 8.20-8.13 (m, 1H), 7.66 (d, J=8.2 Hz, 1H), 7.64-7.58 (m, 1H), 7.56-7.50 (m, 1H), 6.69 (d, J=8.3 Hz, 1H), 4.00 (s, 3H).

2-Methyl-4-(4,4,5,5-tetramethyl-1,3,2-dioxaborolan-2-yl)-phenol (97)

General procedure A: Potassium acetate (2.94 g, 30.0 mmol), bis-(pinacolato)-diboron (3.05 g, 12.0 mmol) and bis(diphenylphosphine) ferrocene dichloropalladium (II) complex with dichloromethane (0.36 g, 0.5 mmol) was added to an anhydrous solution of 4-bromo-2-methylphenol (1.87 g, 10.0 mmol) in dioxane (180 mL) under anhydrous conditions in an atmosphere of nitrogen. The mixture was stirred at 90° C. overnight. The reaction was then quenched with water and extracted with ethyl acetate. The combined organic layers were dried over magnesium sulfate, filtered and concentrated. The residue was purified by flash column chromatography on silica gel (eluent: dichloromethane/ethyl acetate, 10-100%) to give the title compound (12) as a white solid (1.75 g, 75%). ESI-MS m/z: 235.1508 [M+H]$^+$; $^1$H NMR (400 MHz, CDCl$_3$) δ 7.60 (s, 1H), 7.55 (d, J=7.9 Hz, 1H), 6.76 (d, J=7.9 Hz, 1H), 4.97 (s, 1H), 2.25 (s, 3H), 1.33 (s, 12H); $^{13}$C NMR (101 MHz, CDCl$_3$) δ 156.77, 138.04, 134.46, 123.20, 114.56, 83.71, 24.99, 15.56.

1-Methoxy-4-(4-hydroxy-3-methylphenyl)-naphthalene (1)

General procedure B: a mixture of 1-bromo-4-methoxynaphthalene (166 mg, 0.70 mmol), 2-methyl-4-(4,4,5,5-tetramethyl-1,3,2-dioxaborolan-2-yl)-phenol (164 mg, 0.70 mmol), K$_2$CO$_3$ (290 mg, 2.10 mmol) and [1,1'-bis (diphenylphosphino)ferrocene]palladium(II) dichloride (29 mg, 0.04 mmol) in dioxane (10 mL) and H$_2$O (2 mL) was heated at 100° C. overnight in an atmosphere of nitrogen. The reaction was then quenched with water and extracted with ethyl acetate. The combined organic layers were dried over magnesium sulfate, filtered and concentrated. The residue was purified by flash column chromatography on silica gel (eluent: dichloromethane/methanol, 0-10%) to give the title compound as light yellow solid (143 mg, 77% yield). ESI-MS m/z: 263.1075 [M−H]$^−$; Purity: 93.6%. $^1$H NMR (400 MHz, Chloroform-d) δ 8.35-8.28 (m, 1H), 7.91-7.84 (m, 1H), 7.52-7.40 (m, 2H), 7.30 (d, J=7.9 Hz, 1H), 7.25-7.21 (m, 1H), 7.18 (dd, J=8.0, 2.2 Hz, 1H), 6.87 (t, J=8.0 Hz, 2H), 4.04 (s, 3H), 2.33 (s, 3H). $^{13}$C NMR (101 MHz, CDCl$_3$) δ 154.82, 153.02, 133.56, 132.98, 132.84, 132.58, 129.03, 126.82, 126.50, 126.02, 125.81, 125.16, 123.58, 122.27, 114.83, 103.56, 55.71, 15.99.

4-(4-Hydroxy-3-methylphenyl)-1-naphthol (2)

A solution of compound 1 (120 mg, 0.51 mmol) in anhydrous dichloromethane (7 mL) was cooled to −78° C.

and treated dropwise with a 1 M solution of BBr$_3$ in dichloromethane (0.80 mL, 0.80 mmol), and the resulting solution was stirred at the same temperature for 5 min and at 0° C. for 1 h. The mixture was then diluted with water and extracted with ethyl acetate. The organic phase was dried and concentrated. The crude product was purified by flash chromatography (dichloromethane/ethyl acetate 0-10%) to yield light yellow compound (87 mg, 68% yield). ESI-MS m/z: 273.0896 [M+Na]$^+$; Purity: 82.7%. $^1$H NMR (400 MHz, DMSO-d$_6$) δ 10.10 (s, 1H), 9.35 (s, 1H), 8.24-8.12 (m, 1H), 7.82-7.72 (m, 1H), 7.48-7.35 (m, 2H), 7.15 (d, J=7.7 Hz, 1H), 7.12-7.07 (m, 1H), 7.02 (dd, J=8.2, 2.3 Hz, 1H), 6.88 (dd, J=7.9, 6.6 Hz, 2H), 2.18 (s, 3H). $^{13}$C NMR (101 MHz, DMSO) δ 154.38, 152.16, 132.23, 132.08, 130.96, 130.60, 128.10, 126.99, 126.05, 125.32, 124.62, 124.29, 123.63, 122.26, 114.42, 107.64, 16.08.

1-Amino-4-(4-hydroxy-3-methylphenyl)-naphthalene (3)

General procedure B was applied using 4-bromo-1-naphthylamine (45 mg, 0.20 mmol), 2-methyl-4-(4,4,5,5-tetramethyl-1,3,2-dioxaborolan-2-yl)-phenol (47 mg, 0.20 mmol), K$_2$CO$_3$ (83 mg, 0.60 mmol) and [1,1'-bis(diphenylphosphino)ferrocene]palladium(II) dichloride (9 mg, 0.01 mmol), to give light yellow solid (37 mg, 74% yield). ESI-MS m/z: 248.1083 [M−H]$^-$; Purity: 99.3%. $^1$H NMR (400 MHz, Chloroform-d) δ 7.96-7.81 (m, 2H), 7.44 (dddd, J=22.8, 8.2, 6.7, 1.4 Hz, 2H), 7.23-7.20 (m, 2H), 7.17 (ddd, J=8.1, 2.2, 0.6 Hz, 1H), 6.87 (d, J=8.1 Hz, 1H), 6.83 (d, J=7.6 Hz, 1H), 2.32 (s, 3H). $^{13}$C NMR (101 MHz, CDCl$_3$) δ 152.89, 141.43, 133.90, 133.06, 132.68, 131.44, 129.10, 127.44, 126.95, 125.96, 124.88, 123.93, 123.53, 121.15, 114.80, 109.60, 15.99.

4-(4-Hydroxy-3,5-dimethylphenyl)-2-methyl-1(2H)-Phthalazinone (4)

General procedure C: to a solution of phthalic anhydride (222 mg, 1.50 mmol) in dichloroethane (10 mL) was added reactant 2,6-dimethylanisole (122 mg, 1.00 mmol). The solution was cooled in an ice bath. Aluminum chloride (400 mg, 3.00 mmol) was added portionwise. The ice bath was removed after 10 min and warmed to room temperature over 1 h. The reaction mixture was refluxed overnight (16 h), cooled to room temperature, and poured carefully into a stirred solution of ice/1 N HCl (500 mL). The organic layer was separated, and the aqueous layer was extracted with EA (250 mL×3). The combined organic layers were dried over magnesium sulfate, filtered, concentrated, and redissolved in EtOH (15 mL). Methyhydrazine (157 µL, 3.00 mmol) was added, the mixture was refluxed overnight, cooled to room temperature and concentrated. The residue was purified by flash column chromatography on silica gel (eluent: dichloromethane/methanol, 0-10%) to give the title compound as white solid (186 mg, 66%). ESI-MS m/z: 281.1298 [M+H]$^+$; Purity: 90.5%. $^1$NMR (400 MHz, DMSO-d$_6$) δ 8.64 (s, 1H), 8.40-8.28 (m, 1H), 7.94-7.82 (m, 2H), 7.82-7.70 (m, 1H), 7.14 (s, 2H), 3.75 (s, 3H), 2.24 (s, 6H). $^{13}$C NMR (101 MHz, DMSO) δ 158.17, 154.10, 146.27, 133.21, 131.63, 129.29, 128.90, 127.37, 126.91, 126.20, 125.48, 124.27, 48.61, 16.67.

4-Phenyl-1(2H)-phthalazinone (5)

General procedure C was applied using phthalic anhydride (347 mg, 2.36 mmol) in dichloroethane (10 mL), benzene (188 mg, 2.41 mmol), aluminum chloride (640 mg, 4.80 mmol) and hydrazine monohydrate (250 µL, 5.22 mmol). Product was obtained as white solid (376 mg, 72%). Purity: 95.4%. $^1$H NMR (400 MHz, CDCl$_3$) δ 10.49 (s, 1H), 8.62-8.45 (m, 1H), 7.86-7.69 (m, 3H), 7.62-7.57 (m, 2H), 7.56-7.50 (m, 3H).

2-Methyl-4-phenyl-1(2H)-Phthalazinone (6)

To a solution of 5 (22 mg 0.1 mmol) in DMF was added potassium carbonate (28 mg, 0.2 mmol), and methyl iodide (19 µL, 0.3 mmol). The reaction mixture was refluxed overnight, cooled to room temperature, 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give the title compound as white solid (12 mg, 51%). Purity: 98.8%. $^1$H NMR (400 MHz, Chloroform-d) δ 8.54 (ddd, J=7.8, 1.5, 0.8 Hz, 1H), 7.85-7.70 (m, 3H), 7.63-7.47 (m, 5H), 3.93 (s, 3H).

4-(2,5-Dimethylphenyl)-1(2H)-Phthalazinone (7)

General procedure C was applied using phthalic anhydride (500 mg, 3.38 mmol), p-xylene (358 mg, 3.37 mmol), aluminum chloride (846 mg, 6.45 mmol), and hydrazine monohydrate (750 µL, 15.65 mmol). Product was obtained as light yellow solid (540 mg, 64%). ESI-MS m/z: 251.1185 [M+H]$^+$; Purity: 93.0%. $^1$H NMR (400 MHz, DMSO-d$_6$) δ 12.80 (s, 1H), 8.36-8.28 (m, 1H), 7.91-7.81 (m, 2H), 7.30-7.18 (m, 3H), 7.15-7.10 (s, 1H), 2.32 (s, 3H), 2.01 (s, 3H). $^{13}$C NMR (101 MHz, DMSO) δ 159.35, 146.65, 134.95, 134.30, 133.72, 133.28, 131.65, 130.26, 130.18, 129.66, 129.62, 127.67, 126.38, 125.94, 20.45, 18.84.

2,3-Dihydro-1,4-phthalazine (98)

To a solution of phthalic anhydride (500 mg, 3.38 mmol) in acetic acid (5 mL) was added hydrazine monohydrate (200 µL, 4.17 mmol) was added, the mixture was refluxed overnight, cooled to room temperature. The reaction mixture was diluted with water, participation was filtered out and washed with water and DCM, then dried by vacuum to yield white solid (376 mg 69%). $^1$H NMR (400 MHz, DMSO-d$_6$) δ 11.55 (s, 2H), 8.25-7.99 (m, 2H), 7.88 (m, 2H).

1,4-Dichlorophthalazine (99)

Compound 98 (100 mg, 0.51 mmol) was reflux in POCl$_3$ overnight, then poured on ice and neutralized, filtered out, the light yellow solid was dried by pulling air through (112 mg, 84%)$^1$H NMR (400 MHz, Chloroform-d) δ 8.38-8.34 (m, 2H), 8.15-8.09 (m, 2H).

4-Chloro-1-hydroxyphthalazine (100)

Compound 99 (100 mg, 0.55 mmol) was dissolved in 10 ml dioxane and 4 ml 1M NaOH solution. The reaction mixture was stirred at 50° C. for 2 h. The precipitate was filtered out, dried by pulling air through to yield white solid. (82 mg, 90% yield). $^1$H NMR (400 MHz, DMSO-d$_6$) δ 12.88 (s, 1H), 8.28 (ddd, J=7.8, 1.4, 0.7 Hz, 1H), 8.08-7.94 (m, 3H).

4-(3,5-Dimethylphenyl)-1(2H)-phthalazinone (8)

General procedure B: a mixture of 4-chloro-1(2H)-phthalazinone (200 mg, 1.11 mmol), 3,5-dimethylphenylboronic acid (166 mg, 1.11 mmol), Na$_2$CO$_3$ (350 mg, 3.30 mmol) and [1,1'-bis(diphenylphosphino)ferrocene]palladium(II) dichloride (62 mg, 0.05 mmol) in dioxane (10 mL) and H$_2$O (2 mL) was heated at 100° C. overnight in an atmosphere of nitrogen. The reaction was then quenched with water and extracted with ethyl acetate. The combined organic layers were dried over magnesium sulfate, filtered and concentrated. The residue was purified by flash column chromatography on silica gel (eluent: dichloromethane/methanol, 0-10%) to give the title compound as white solid (182 mg, 66%). ESI-MS m/z: 251.1190 [M+H]$^+$; Purity: 96.8%. $^1$H NMR (400 MHz, DMSO-d$_6$) δ 12.81 (s, 1H), 8.43-8.27 (m, 1H), 7.97-7.82 (m, 2H), 7.73-7.64 (m, 1H), 7.17 (s, 3H), 2.36 (s, 6H). $^{13}$C NMR (101 MHz, DMSO) δ 159.22, 146.59, 137.65, 134.96, 133.57, 131.56, 130.27, 129.05, 127.85, 126.99, 126.66, 126.03, 20.90.

4-(4-Methoxyphenyl)-1(2H)-phthalazinone (9)

General procedure C was applied. To a solution of phthalic anhydride (95 mg, 0.64 mmol) in dichloroethane (10 mL) was added methoxylbenzene (50 mg, 0.46 mmol). The solution was cooled in an ice bath. Aluminum chloride (185 mg, 1.39 mmol) was added portionwise. The ice bath was removed after 10 min and warmed to room temperature over 1 h. The reaction mixture was refluxed overnight, cooled to room temperature, and poured carefully into a stirred solution of ice/1 N HCl (150 mL). The organic layer was separated, and the aqueous layer was extracted with ethyl acetate (100 mL×3). The combined organic layers were dried over magnesium sulfate, filtered, concentrated, and redissolved in EtOH (15 mL). Hydrazine monohydrate (150 μL, 3.13 mmol) was added, the mixture was refluxed overnight, cooled to room temperature and concentrated. The residue was purified by flash column chromatography on silica gel (eluent: dichloromethane/methanol, 0-10%) to give the title compound as white solid (102 mg, 63%). Purity: 99.1%. $^1$H NMR (400 MHz, DMSO-d$_6$) δ 12.79 (s, 1H), 8.36-8.30 (m, 1H), 7.95-7.82 (m, 2H), 7.73-7.66 (m, 1H), 7.58-7.48 (m, 2H), 7.14-7.06 (m, 2H), 3.84 (s, 3H). 4-(4-Methoxyphenyl)-2-methyl-1(2H)-phthalazinone (10) To a solution of 9 (22 mg 0.1 mmol) in DMF was added potassium carbonate (28 mg, 0.2 mmol), and methyl iodide (19 μL, 0.3 mmol). The reaction mixture was refluxed overnight, cooled to room temperature, 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give the title compound as white solid (12 mg, 51%). Purity: 97.2%. $^1$H NMR (400 MHz, DMSO-d$_6$) δ 8.41-8.28 (m, 1H), 7.91-7.88 (m, 2H), 7.75-7.69 (m, 1H), 7.58-7.52 (m, 2H), 7.14-7.09 (m, 2H), 3.85 (s, 3H), 3.77 (s, 3H).

4-(4-Methoxy-3,5-dimethylphenyl)-1(2H)-phthalazinone (11)

General procedure C was applied using phthalic anhydride (100 mg, 0.68 mmol), 2,6-dimethylanisole (96 mg, 0.70 mmol), aluminum chloride (185 mg, 1.39 mmol), and hydrazine monohydrate (150 μL, 3.13 mmol). Product was obtained as light yellow solid (128 mg, 67%). ESI-MS m/z: 281.1296 [M+H]$^+$; Purity: 93.9%. $^1$H NMR (400 MHz, DMSO-d$_6$) δ 12.79 (s, 1H), 8.37-8.29 (m, 1H), 7.95-7.84 (m, 2H), 7.75-7.67 (m, 1H), 7.24 (s, 2H), 3.73 (s, 3H), 2.30 (s, 6H). $^{13}$C NMR (101 MHz, DMSO) δ 159.21, 157.15, 146.23, 133.57, 131.53, 130.58, 130.45, 129.70, 129.07, 127.85, 126.73, 126.03, 59.38, 15.88.

4-(4-Trifluoromethoxyl-3-methylphenyl)-1(2H)-phthalazinone (12)

To a solution of 4-(4-hydroxy-3-methylphenyl)-1(2H)-phthalazinone (100 mg 0.40 mmol) in THF was added pyridine (96 ul, 0.50 mmol), and trifluoromethanesulfonic anhydride (80 μL, 0.48 mmol). The reaction mixture was refluxed overnight, cooled to room temperature, 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give the title compound as white solid (66 mg, 52%). ESI-MS m/z: 319.0695 [M−H]$^-$; Purity: 99.9%. $^1$H NMR (400 MHz, DMSO-d$_6$) δ 12.95 (s, 1H), 8.38-8.32 (m, 1H), 7.97-7.88 (m, 2H), 7.76-7.72 (m, 1H), 7.71-7.65 (m, 1H), 7.64-7.60 (m, 1H), 7.57 (d, J=8.5 Hz, 1H), 2.43 (s, 3H). $^{13}$C NMR (101 MHz, DMSO) δ 159.71, 148.75, 145.38, 136.06, 134.30, 133.81, 132.31, 131.23, 129.76, 129.15, 128.28, 126.87, 126.62, 121.98, 117.01, 16.28.

2,6-Dimethyl-4-(4,4,5,5-tetramethyl-[1,3,2]dioxaborolan-2-yl)-benzoic acid (101)

Potassium acetate (385 mg g, 3.9 mmol), bis-(pinacolato)-diboron (165 mg, 0.65 mmol) and bis(diphenylphosphine) ferrocene dichloropalladium (II) complex with dichloromethane (16 mg, 0.02 mmol) was added to an anhydrous solution of 4-bromo-2,6-dimethylbenzoic acid (100 mg, 0.44 mmol) in dioxane (180 mL) under anhydrous conditions in an atmosphere of nitrogen. The mixture was stirred at 90° C. overnight. The reaction was then quenched with water and extracted with ethyl acetate. The combined organic layers were dried over magnesium sulfate, filtered and concentrated. The residue was purified by flash column chromatography on silica gel (eluent: dichloromethane/ethyl acetate, 10-100%) to give the title compound as a white solid (70 mg, 57%). $^1$H NMR (400 MHz, Chloroform-d) δ 7.63-7.47 (s, 2H), 2.48-2.40 (s, 6H), 1.35 (s, 12H).

4-(4-Carboxylic-3,5-dimethylphenyl)-1(2H)-phthalazinone (13)

General procedure B was applied using 4-chloro-1(2H)-phthalazinone (200 mg, 1.11 mmol), 3,5-Dimethylphenylboronic acid (166 mg, 1.11 mmol), Na$_2$CO$_3$ (350 mg, 3.30 mmol) and [1,1'-bis(diphenylphosphino)ferrocene]palladium(II) dichloride (62 mg, 0.05 mmol) in dioxane (10 mL) and H$_2$O (2 mL) to give light yellow solid (164 mg, 50% yield). ESI-MS m/z: 295.1089 [M+H]$^+$; Purity: 99.7%. $^1$H NMR (400 MHz, DMSO-d$_6$) δ 12.80 (s, 1H), 8.33 (dd, J=7.3, 1.9 Hz, 1H), 7.89 (tt, J=7.5, 5.6 Hz, 2H), 7.76-7.68 (m, 1H), 7.15 (s, 2H), 2.32 (s, 6H). $^{13}$C NMR (101 MHz, DMSO) δ 159.23, 146.54, 142.39, 141.22, 133.58, 132.89, 132.63, 131.56, 129.13, 127.86, 127.68, 126.72, 126.04, 19.53.

1-Methyl-4-(4,4,5,5-tetramethyl-[1,3,2]dioxaborolan-2-yl)-benzoic acid (102)

Potassium acetate (1473 mg, 15.00 mmol), bis-(pinacolato)-diboron (1523 mg, 6.00 mmol) and bis(diphenylphosphine) ferrocene dichloropalladium (II) complex with dichloromethane (183 mg, 0.25 mmol) was added to an anhydrous solution of 4-bromo-2-methylbenzoic acid (1075 mg, 5.00 mmol) in dioxane (180 mL) under anhydrous conditions in an atmosphere of nitrogen. The mixture was stirred at 90° C. overnight. The reaction was then quenched with water and extracted with ethyl acetate. The combined organic layers were dried over magnesium sulfate, filtered and concentrated. The residue was purified by flash column chromatography on silica gel (eluent: dichloromethane/ethyl acetate, 10-100%) to give the title compound as a white solid (970 mg, 73%). ESI-MS m/z: 285.1284 [M+H]$^+$; $^1$H NMR (400 MHz, DMSO-d$_6$) δ 7.79 (d, J=7.6 Hz, 1H), 7.59-7.54 (m, 2H), 2.52 (s, 3H), 1.30 (s, 12H). $^{13}$C NMR (101 MHz, DMSO) δ 168.70, 162.31, 137.91, 137.42, 133.30, 131.70, 129.35, 83.94, 24.67, 20.94.

4-(4-Carboxylic-3-methylphenyl)-1(2H)-phthalazinone (14)

General procedure B was applied using 4-chloro-1(2H)-phthalazinone (83 mg, 0.46 mmol), 2-methyl-4-(4,4,5,5-tetramethyl-[1,3,2]dioxaborolan-2-yl)-benzoic acid (100 mg, 0.38 mmol), Na$_2$CO$_3$ (193 mg, 2.30 mmol) and [1,1'-bis(diphenylphosphino)ferrocene]palladium(II) dichloride (18 mg, 0.03 mmol), to give light yellow solid (87 mg, 82% yield). ESI-MS m/z: 303.0752 [M+H]$^+$; Purity: 96.4%. $^1$H NMR (400 MHz, DMSO-d$_6$) δ 12.91 (s, 1H), 8.36-8.32 (m, 1H), 7.94 (d, J=7.9 Hz, 1H), 7.92-7.88 (m, 2H), 7.72-7.67 (m, 1H), 7.52-7.45 (m, 2H), 2.60 (s, 3H). $^{13}$C NMR (101 MHz, DMSO) δ 169.11, 159.22, 145.73, 138.95, 137.51, 137.16, 133.71, 132.11, 131.73, 130.19, 128.80, 127.85, 126.68, 126.48, 126.11, 21.21.

2,6-Dimethyl-4-(4,4,5,5-tetramethyl-1,3,2-dioxaborolan-2-yl)aniline (103)

General procedure A was applied using potassium acetate (884 mg g, 9.01 mmol), bis-(pinacolato)-diboron (254 mg, 1.00 mmol) and bis(diphenylphosphine) ferrocene dichloropalladium (II) complex with dichloromethane (74 mg, 0.05 mmol) was added to an anhydrous solution of 4-bromo-1-methoxyl-2-nitrobenzene (100 mg, 0.50 mmol). Product was obtained as light yellow solid (97 mg, 78%). $^1$H NMR (400 MHz, Chloroform-d) 7.15-7.12 (m, 2H), 2.23 (d, J=0.7 Hz, 6H), 1.23 (s, 12H).

4-(4-Amino-3-methylphenyl)-1(2H)-phthalazinone (15)

General procedure B was applied using 4-chloro-1(2H)-phthalazinone (109 mg, 0.60 mmol), 2,6-dimethyl-4-(4,4,5,5-tetramethyl-1,3,2-dioxaborolan-2-yl)aniline (124 mg, 0.50 mmol), Na$_2$CO$_3$ (160 mg, 1.51 mmol) and [1,1'-bis(diphenylphosphino)ferrocene]palladium(II) dichloride (18 mg, 0.02 mmol). ESI-MS m/z: 266.1295 [M+H]$^+$; Purity: 92.9%. $^1$H NMR (400 MHz, Chloroform-d) δ 9.94 (s, 1H), 8.50 (ddd, J=6.0, 3.4, 0.7 Hz, 1H), 7.91-7.84 (m, 1H), 7.83-7.76 (m, 2H), 7.18 (p, J=0.7 Hz, 2H), 3.82 (s, 2H), 2.26 (s, 6H). $^{13}$C NMR (101 MHz, DMSO) δ 159.41, 147.40, 145.18, 133.60, 131.51, 129.59, 129.00, 128.01, 127.19, 126.14, 122.47, 120.72, 18.04. $^{13}$C NMR (101 MHz, DMSO) δ 159.41, 147.40, 145.18, 133.60, 131.51, 129.59, 129.00, 128.01, 127.19, 126.14, 122.47, 120.72, 18.04.

Methyl-2-methyl-4-(4,4,5,5-tetramethyl-1,3,2-dioxaborolan-2-yl)benzoate (104)

General procedure A was applied using potassium acetate (884 mg g, 9.00 mmol), bis-(pinacolato)-diboron (305 mg, 1.20 mmol) and bis(diphenylphosphine) ferrocene dichloropalladium (I) complex with dichloromethane (37 mg, 0.05 mmol) and 4-bromo-2-methyl-benzoic acid methyl ester (229 mg, 1.00 mmol). Product was obtained as white solid (222 mg, 80%). $^1$H NMR (400 MHz, Chloroform-d) δ 7.88 (d, J=7.7 Hz, 1H), 7.70-7.64 (m, 2H), 3.89 (s, 3H), 2.59 (d, J=0.7 Hz, 3H), 1.35 (s, 12H).

4-(4-Carbomethoxyl-3-methylphenyl)-1(2H)-phthalazinone (16)

General procedure B was applied using 4-chloro-1(2H)-phthalazinone (147 mg, 0.81 mmol), 2-methyl-4-(4,4,5,5-tetramethyl-[1,3,2]dioxaborolan-2-yl)-benzoic acid methyl ester (222 mg, 0.81 mmol), Na$_2$CO$_3$ (259 mg, 2.44 mmol) and [1,1'-bis(diphenylphosphino)ferrocene]palladium(II) dichloride (14 mg, 0.02 mmol). Product was obtained as light yellow solid (157 mg, 66%). ESI-MS m/z: 317.0911 [M+Na]$^+$; Purity: 99.6%. $^1$H NMR (400 MHz, DMSO-d$_6$) δ 12.93 (s, 1H), 8.46-8.31 (m, 1H), 7.98 (d, J=8.0 Hz, 1H), 7.94-7.85 (m, 2H), 7.73-7.66 (m, 1H), 7.59-7.56 (m, 1H), 7.53 (dd, J=8.0, 1.8 Hz, 1H), 3.88 (s, 3H), 2.60 (s, 3H). $^{13}$C NMR (101 MHz, DMSO) δ 167.02, 159.23, 145.46, 139.51, 138.48, 133.76, 132.40, 131.79, 130.30, 129.74, 128.70, 127.84, 126.97, 126.40, 126.14, 52.08, 21.07.

4-(4-Acetoxy-3,5-dimethylphenyl)-1(2H)-phthalazinone (17)

4-(4-hydroxy-3,5-dimethylphenyl)-1(2H)-phthalazinone (133 mg, 0.50 mmol) was reflux in dioxane (6 mL) with acetic anhydride (72 uL, 0.75 mmol) and TEA (208 uL, 1.50 mmol). The reaction mixture was refluxed overnight, cooled to room temperature, 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give the title compound as white solid (121 mg, 78%). ESI-MS m/z: 309.1240 [M+H]$^+$; Purity: 92.7%. H NMR (400 MHz, DMSO-d$_6$) δ 12.85 (s, 1H), 8.36-8.29 (m, 1H), 7.90 (pd, J=7.1, 1.7 Hz, 2H), 7.71 (dd, J=7.6, 1.6 Hz, 1H), 7.33 (s, 2H), 2.39 (s, 3H), 2.18 (s, 6H). $^{13}$C NMR (101 MHz, DMSO) δ 168.53, 159.22, 148.43, 145.88, 133.66, 132.50, 131.62, 130.27, 129.38, 128.95, 127.83, 126.64, 126.06, 20.26, 15.96.

4-(4-Acetoxy-3-methylphenyl)-1(2H)-phthalazinone (18)

4-(4-Hydroxy-3-methylphenyl)-1(2H)-phthalazinone (133 mg, 0.50 mmol) was reflux in dioxane (6 mL) with acetic anhydride (72 uL, 0.75 mmol) and TEA (208 uL, 1.50 mmol). The reaction mixture was refluxed overnight, cooled to room temperature, 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give light yellow solid (71 mg, 46% yield). ESI-MS m/z: 295.1084 [M+H]$^+$; Purity: 90.0%. $^1$H NMR (400 MHz, DMSO-d$_6$) δ 12.87 (s, 1H), 8.37-8.29 (m, 1H), 7.90 (m, 2H), 7.73-7.68 (m, 1H), 7.52 (d, J=2.1 Hz, 1H), 7.33 (dd, J=8.2, 2.2 Hz, 1H), 7.24 (d, J=8.2 Hz, 1H), 2.35 (s, 3H), 2.21 (s, 3H). $^{13}$C NMR (101 MHz, DMSO) δ 168.95, 159.24, 149.64, 145.81, 133.69, 132.76, 131.90, 131.68, 130.31, 128.96, 128.04, 127.86, 126.58, 126.10, 122.36, 20.63, 15.77.

4-(4-Hydroxyphenyl)phthalazin-1(2H)-one (19)

To a solution of phthalic anhydride (100 mg, 0.68 mmol) in dichloroethane (10 mL) was added phenol (50 µL, 0.57 mmol). The solution was cooled in an ice bath. Aluminum chloride (185 mg, 1.39 mmol) was added portionwise. The ice bath was removed after 10 min and warmed to room temperature over 1 h. The reaction mixture was refluxed overnight, cooled to room temperature, and poured carefully into a stirred solution of ice/1 N HCl (150 mL). The organic layer was separated, and the aqueous layer was extracted with ethyl acetate (100 mL×3). The combined organic layers were dried over magnesium sulfate, filtered, concentrated, and redissolved in EtOH (15 mL). Hydrazine monohydrate (150 µL, 3.13 mmol) was added, the mixture was refluxed overnight, cooled to room temperature and concentrated. The residue was purified by flash column chromatography on silica gel (eluent: dichloromethane/methanol, 0-10%) to give the title compound as white solid (120 mg, 88%). Purity: 98.5%. $^1$H NMR (400 MHz, DMSO-$d_6$) δ 12.74 (s, 1H), 9.82 (s, 1H), 8.32 (d, J=7.5 Hz, 1H), 7.88 (t, J=6.6 Hz, 2H), 7.73 (d, J=7.6 Hz, 1H), 7.40 (d, J=8.2 Hz, 2H), 6.92 (d, J=8.2 Hz, 2H).

4-(4-Hydroxy-3,5-dimethylphenyl)-1(2H)-phthalazinone (20)

General procedure C was applied using phthalic anhydride (100 mg, 0.68 mmol), 2,6-dimethylphenol (96 mg, 0.70 mmol), aluminum chloride (185 mg, 1.39 mmol), and hydrazine monohydrate (150 µL, 3.13 mmol). Product was obtained as light yellow solid (98 mg, 54%). Purity: 95.7%. $^1$H NMR (400 MHz, DMSO-$d_6$) δ 12.71 (s, 1H), 8.35-8.28 (m, 1H), 7.92-7.83 (m, 2H), 7.76-7.71 (m, 1H), 7.13 (s, 2H), 2.24 (s, 6H).

4-(4-Hydroxy-3-methylphenyl)-1(2H)-phthalazinone (21)

General procedure C was applied using phthalic anhydride (100 mg, 0.68 mmol), 2,6-dimethylphenol (96 mg, 0.70 mmol), aluminum chloride (185 mg, 1.39 mmol), and hydrazine monohydrate (150 µL, 3.13 mmol). Product was obtained as light yellow solid (98 mg, 54%). Purity: 97.1%. $^1$H NMR (400 MHz, DMSO-$d_6$) δ 12.72 (s, 1H), 9.69 (s, 1H), 8.38-8.20 (m, 1H), 7.95-7.81 (m, 2H), 7.79-7.70 (m, 1H), 7.37-7.25 (m, 1H), 7.24-7.12 (m, 1H), 6.92 (d, J=8.2 Hz, 1H), 2.19 (s, 3H).

4-(4-Hydroxy-3-ethylphenyl)-1(2H)-phthalazinone (22)

General procedure C was applied using phthalic anhydride (100 mg, 0.68 mmol), 2-ethylphenol (96 mg, 0.70 mmol), aluminum chloride (185 mg, 1.39 mmol), and hydrazine monohydrate (150 L, 3.13 mmol). Product was obtained as light yellow solid (143 mg, 79%). ESI-MS m/z: 267.1140 [M+H]$^+$; Purity: 96.6%. $^1$H NMR (400 MHz, DMSO-$d_6$) δ 12.72 (s, 1H), 9.69 (s, 1H), 8.36-8.28 (m, 1H), 7.94-7.82 (m, 2H), 7.79-7.72 (m, 1H), 7.28 (d, J=2.3 Hz, 1H), 7.22 (dd, J=8.2, 2.3 Hz, 1H), 6.93 (d, J=8.2 Hz, 1H), 2.61 (q, J=7.5 Hz, 2H), 1.17 (t, J=7.5 Hz, 3H). $^{13}$C NMR (101 MHz, DMSO) δ 159.16, 155.77, 146.68, 133.48, 131.42, 130.03, 130.00, 129.28, 127.92, 127.87, 126.82, 126.02, 125.72, 114.65, 22.71, 14.14.

4-(4-Hydroxy-3,5-diisopropylphenyl)-1(2H)-phthalazinone (23)

General procedure C was applied using phthalic anhydride (500 mg, 3.38 mmol), 2,6-diisopropylphenol (608 mg, 3.41 mmol), aluminum chloride (846 mg, 6.45 mmol), and hydrazine monohydrate (750 µL, 15.65 mmol). Product was obtained as light yellow solid (528 mg, 48.5%). ESI-MS m/z: 323.1762 [M+H]$^+$; Purity: 92.9%. $^1$H NMR (400 MHz, DMSO-$d_6$) δ 12.71 (s, 1H), 8.48 (s, 1H), 8.37-8.28 (m, 1H), 7.98-7.83 (m, 2H), 7.76-7.67 (m, 1H), 7.18 (s, 2H), 3.39 (h, J=6.9 Hz, 2H), 1.19 (d, J=6.8 Hz, 12H). $^{13}$C NMR (101 MHz, DMSO) δ 159.14, 151.50, 147.07, 135.22, 133.51, 131.40, 129.32, 127.98, 126.72, 126.46, 126.07, 124.26, 26.19, 22.93.

4-(4-Hydroxy-2,3,5-trimethylphenyl)-1(2H)-phthalazinone (24)

General procedure C was applied using phthalic anhydride (200 mg, 1.35 mmol), 2,5,6-trimethylphenol (367 mg, 3.00 mmol), aluminum chloride (373 mg, 2.80 mmol), and hydrazine monohydrate (300 µL, 6.26 mmol). Product was obtained as light yellow solid (225 mg, 64%). ESI-MS m/z: 281.1290 [M+H]$^+$; Purity: 99.9%. $^1$H NMR (400 MHz, DMSO-$d_6$) δ 12.70 (s, 1H), 8.33-8.27 (m, 1H), 8.24 (s, 1H), 7.86-7.70 (m, 2H), 7.18-7.07 (m, 1H), 6.73-6.67 (m, 1H), 2.25 (s, 3H), 2.09 (s, 3H), 1.87 (s, 3H). $^{13}$C NMR (101 MHz, DMSO) δ 159.72, 153.04, 144.49, 137.65, 134.00, 133.39, 131.24, 130.63, 128.00, 126.01, 125.65, 122.63, 120.75, 119.77, 19.96, 19.01, 11.96.

4-(4-Hydroxy-naphthyl)-1(2H)-phthalazinone (25)

General procedure C was applied using phthalic anhydride (200 mg, 1.35 mmol), 1-naphthol (292 mg, 2.02 mmol), aluminum chloride (270 mg, 2.02 mmol), and hydrazine monohydrate (300 µL, 6.26 mmol). Product was obtained as light yellow solid (133 mg, 34%). ESI-MS m/z: 289.0986 [M+H]$^+$; Purity: 97.9%. $^1$H NMR (400 MHz, DMSO-$d_6$) δ 12.82 (s, 1H), 9.64 (s, 1H), 8.35-8.31 (m, 1H), 8.28 (ddd, J=7.7, 2.0, 0.8 Hz, 1H), 7.97-7.90 (m, 1H), 7.87-7.78 (m, 2H), 7.62-7.51 (m, 3H), 7.39-7.33 (m, 2H). $^{13}$C NMR (101 MHz, DMSO) δ 159.88, 150.91, 145.28, 134.69, 133.46, 131.46, 130.38, 128.22, 128.02, 127.75, 127.01, 126.88, 125.83, 125.57, 125.25, 122.65, 119.26, 116.16.

4-(4,4,5,5-tetramethyl-1,3,2-dioxaborolan-2-yl)-2-(trifluoromethyl)phenol (105)

General procedure A was applied using potassium acetate (371 mg g, 3.77 mmol), bis-(pinacolato)-diboron (127 mg, 0.50 mmol) and bis(diphenylphosphine) ferrocene dichloropalladium (II) complex with dichloromethane (19 mg, 0.03 mmol) was added to an anhydrous solution of 4-bromo-2-trifluoromethyl)phenol (100 mg, 0.42 mmol). Product was obtained as white solid (70 mg, 55%). $^1$H NMR (400 MHz, Chloroform-d) δ 7.97 (s, 1H), 7.86-7.82 (m, 1H), 6.95 (d, J=8.1 Hz, 1H), 1.34 (s, 12H).

4-(4-Hydroxy-3-trifluoromethylphenyl)-1(2H)-phthalazinone (26)

General procedure B was applied using 4-Chloro-1(2H)-phthalazinone (44 mg, 0.24 mmol), 4-(4,4,5,5-tetramethyl- 1,3,2-dioxaborolan-2-yl)-2-(trifluoromethyl)phenol (70 mg, 0.24 mmol), Na$_2$CO$_3$ (78 mg, 0.74 mmol) and [1,1'-bis(diphenylphosphino)ferrocene]palladium(II) dichloride (14 mg, 0.02 mmol). Product was obtained as white solid (37 mg, 50%). ESI-MS m/z: 305.0546 [M−H]$^−$; Purity: 99.3%. $^1$H NMR (400 MHz, DMSO-d$_6$) δ 12.72 (s, 1H), 8.36-8.29 (m, 1H), 7.96-7.85 (m, 3H), 7.75 (dd, J=8.1, 1.2 Hz, 1H), 7.39 (dd, J=8.3, 2.4 Hz, 1H), 6.80 (d, J=8.4 Hz, 1H). $^{13}$C NMR (101 MHz, DMSO) δ 171.21, 163.91, 162.31, 159.17, 146.74, 133.43, 132.57, 131.40, 131.10, 129.29, 127.97, 126.77, 126.05, 122.74, 116.21.

4-(4-Methoxyl-3-trifluoromethylphenyl)-1(2H)-phthalazinone (27)

To a solution of 26 (20 mg 0.1 mmol) in DMF was added potassium carbonate (28 mg, 0.2 mmol), and methyl iodide (19 μL, 0.3 mmol). The reaction mixture was refluxed overnight, cooled to room temperature, 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give the title compound as white solid (13 mg, 63%). ESI-MS m/z: 321.0857 [M+H]$^+$; Purity: 97.0%. $^1$H NMR (400 MHz, DMSO-d$_6$) δ 12.87 (s, 1H), 8.39-8.31 (m, 1H), 7.94-7.86 (m, 3H), 7.81 (d, J=2.2 Hz, 1H), 7.70-7.64 (m, 1H), 7.45 (d, J=8.6 Hz, 1H), 3.99 (s, 3H). $^{13}$C NMR (101 MHz, DMSO) δ 159.78, 157.90, 145.57, 135.72, 134.27, 132.25, 129.39, 128.27, 128.10, 127.55, 126.81, 126.62, 122.65, 117.59, 113.52, 56.88.

2-Hydroxy-5-(4,4,5,5-tetramethyl-[1,3,2]dioxaborolan-2-yl)-benzonitrile (106)

General procedure A was applied using potassium acetate (446 mg g, 4.54 mmol), bis-(pinacolato)-diboron (192 mg, 0.76 mmol) and bis(diphenylphosphine) ferrocene dichloropalladium (II) complex with dichloromethane (19 mg, 0.03 mmol) was added to an anhydrous solution of 5-bromo-2-hydroxybenzonitrile (100 mg, 0.51 mmol). Product was obtained as light yellow solid (88 mg, 70%). $^1$H NMR (400 MHz, Chloroform-d) δ 7.98 (dd, J=1.6, 0.5 Hz, 1H), 7.88 (dd, J=8.4, 1.6 Hz, 1H), 6.96 (dd, J=8.3, 0.5 Hz, 1H), 1.33 (s, 12H).

4-(4-Hydroxy-3-cyanophenyl)-1(2H)-phthalazinone (28)

General procedure B was applied using 4-chloro-1(2H)-phthalazinone (186 mg, 1.03 mmol), 104 (153 mg, 1.02 mmol), Na$_2$CO$_3$ (433 mg, 4.08 mmol) and [1,1'-bis(diphenylphosphino) ferrocene]palladium(II) dichloride (58 mg, 0.05 mmol). ESI-MS m/z: 264.0779 [M+H]$^+$; Purity: 95.6%. $^1$H NMR (400 MHz, DMSO-d$_6$) δ 12.85 (s, 1H), 11.52 (s, 1H), 8.39-8.29 (m, 1H), 7.95-7.86 (m, 2H), 7.84 (d, J=2.2 Hz, 1H), 7.76-7.66 (m, 2H), 7.17 (d, J=8.7 Hz, 1H). $^{13}$C NMR (101 MHz, DMSO) δ 160.70, 159.22, 144.81, 135.76, 134.03, 133.73, 131.72, 128.92, 127.84, 126.53, 126.09, 116.59, 116.39, 99.11, 30.70.

2-Nitro-4-(4,4,5,5-tetramethyl-[1,3,2]dioxaborolan-2-yl)-anisole (107)

General procedure A was applied using potassium acetate (884 mg g, 9.01 mmol), bis-(pinacolato)-diboron (381 mg, 2.48 mmol) and bis(diphenylphosphine) ferrocene dichloropalladium (II) complex with dichloromethane (37 mg, 0.03 mmol) was added to an anhydrous solution of 4-bromo-1-methoxyl-2-nitrobenzene (232 mg, 1.00 mmol). Product was obtained as light yellow solid (232 mg, 83%). ESI-MS m/z: 280.1356 [M+H]$^+$; $^1$H NMR (400 MHz, Chloroform-d) δ 8.25 (d, J=1.6 Hz, 1H), 7.94 (dd, J=8.4, 1.6 Hz, 1H), 7.06 (d, J=8.4 Hz, 1H), 3.98 (s, 3H), 1.34 (s, 12H). $^{13}$C NMR (101 MHz, CDCl$_3$) δ 155.03, 140.64, 132.02, 132.01, 112.74, 84.40, 56.56, 24.93.

4-(4-Methoxyl-3-nitrophenyl)-1(2H)-phthalazinone (29)

General procedure B was applied using 4-chloro-1(2H)-phthalazinone (86 mg, 0.48 mmol), 105 (132 mg, 0.48 mmol), Na$_2$CO$_3$ (153 mg, 1.44 mmol) and [1,1'-bis(diphenylphosphino) ferrocene]palladium(II) dichloride (17 mg, 0.03 mmol). ESI-MS m/z: 298.0830 [M+H]$^+$; Purity: 96.5%. $^1$H NMR (400 MHz, DMSO-d$_6$) δ 12.93 (s, 1H), 8.39-8.28 (m, 1H), 8.12 (d, J=2.3 Hz, 1H), 8.01-7.85 (m, 3H), 7.77-7.64 (m, 1H), 7.55 (d, J=8.8 Hz, 1H), 4.03 (s, 3H). $^{13}$C NMR (101 MHz, DMSO) δ 159.70, 152.78, 144.74, 139.60, 135.70, 134.25, 132.28, 129.27, 128.32, 127.81, 126.78, 126.64, 126.22, 115.01, 57.42.

4-(4-Hydroxy-3-methylphenyl)-2-methyl-1(2H)-phthalazinone (30)

To a solution of 21 (80 mg 0.32 mmol) in THF was added sodium hydride (20 mg, 0.50 mmol), and methyl iodide (30 μL, 0.45 mmol). The reaction mixture was refluxed overnight, cooled to room temperature, 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give the title compound as white solid (63 mg, 73% yield). ESI-MS m/z: 267.1143 [M+H]$^+$; Purity: 97.5%. $^1$H NMR (400 MHz, DMSO-d$_6$) δ 9.73 (s, 1H), 8.37-8.30 (m, 1H), 7.95-7.84 (m, 2H), 7.78-7.70 (m, 1H), 7.30 (dd, J=2.4, 0.9 Hz, 1H), 7.23 (ddd, J=8.2, 2.3, 0.7 Hz, 1H), 6.93 (d, J=8.2 Hz, 1H), 3.76 (s, 3H), 2.20 (s, 3H). $^{13}$C NMR (101 MHz, DMSO) δ 158.17, 156.30, 146.22, 133.22, 131.66, 131.62, 128.89, 127.99, 127.39, 126.86, 126.23, 125.23, 124.11, 114.42, 55.43, 15.99.

4-(4-Hydroxy-3-methylphenyl)-2-ethyl-1(2H)-phthalazinone (31)

Compound 21 (100 mg, 0.40 mmol) was reflux in DMF (6 mL) with ethylbromide (36 uL, 0.48 mmol) and sodium hydride (20 mg, 0.50 mmol). The reaction mixture was refluxed overnight, cooled to room temperature, 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give light yellow solid (12 mg, 11%). ESI-MS m/z: 281.1288 [M+H]$^+$; Purity: 94.8%. $^1$H NMR (400 MHz, DMSO-d$_6$) δ 9.73 (s, 1H), 8.38-8.29 (m, 1H), 7.97-7.81 (m, 2H), 7.81-7.68 (m, 1H), 7.31 (dd, J=2.3, 0.9 Hz, 1H), 7.24 (dd, J=8.1, 2.3 Hz, 1H), 6.93 (d, J=8.2 Hz, 1H), 4.20 (q, J=7.1 Hz, 2H), 2.20 (s, 3H), 1.32 (t, J=7.1 Hz, 3H). $^{13}$C NMR (101 MHz, CDCl$_3$) δ 159.05, 155.14, 132.74, 132.24, 131.36, 129.58, 128.51, 128.46, 127.67, 127.22, 126.96, 124.55, 115.16, 77.48, 77.16, 76.84, 46.73, 16.06, 13.94.

4-(4-Ethoxyl-3-methylphenyl)-2-ethyl-1(2H)-phthalazinone (32)

Compound 21 (100 mg, 0.40 mmol) was reflux in DMF (6 mL) with ethylbromide (36 uL, 0.48 mmol) and sodium hydride (20 mg, 0.50 mmol). The reaction mixture was refluxed overnight, cooled to room temperature, 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give light yellow solid (47 mg, 38%). ESI-MS m/z: 309.1602 [M+H]$^+$; Purity: 97.2%. $^1$H NMR (400 MHz, Chloroform-d) δ 8.57-8.48 (m, 1H), 7.80-7.69 (m, 3H), 7.37 (m, 2H), 6.94 (d, J=9.0 Hz, 1H), 4.36 (q, J=7.2 Hz, 2H), 4.12 (q, J=7.0 Hz, 2H), 2.31 (s, 3H), 1.47 (m, 6H). $^{13}$C NMR (101 MHz, CDCl$_3$) δ 158.95, 158.06, 147.27, 132.63, 131.75, 131.24, 129.60, 128.51, 128.18, 127.40, 127.18, 127.15, 126.97, 110.95, 63.86, 46.64, 16.54, 15.07, 13.94.

2,4-Diphenyl-1(2H)-phthalazinone (33)

Compound 5 (100 mg, 0.40 mmol) was reflux in DMF (6 mL) with phenylbromide (36 uL, 0.48 mmol) and sodium hydride (20 mg, 0.50 mmol). The reaction mixture was refluxed overnight, cooled to room temperature, 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give light yellow solid (12 mg, 11%). Purity: 95.7%. $^1$H NMR (400 MHz, Chloroform-d) δ 8.68 (ddd, J=8.0, 1.3, 0.6 Hz, 1H), 7.95 (ddd, J=8.2, 7.1, 1.2 Hz, 1H), 7.72 (ddd, J=8.4, 7.1, 1.3 Hz, 1H), 7.51 (ddd, J=8.2, 1.2, 0.7 Hz, 1H), 7.40-7.35 (m, 3H), 7.32-7.21 (m, 7H).

4-(4-Hydroxy-3-methylphenyl)-5-methyl-1(2H)-phthalazinone (34)

General procedure C was applied using 3-methylphthalic acid anhydride (162 mg, 1.00 mmol), 1-naphthol (147 mg, 1.20 mmol), aluminum chloride (800 mg, 6.00 mmol), and hydrazine monohydrate (100 μL, 2.05 mmol). Product was obtained as light yellow solid (123 mg, 46%). ESI-MS m/z: 265.0979 [M−H]$^-$; Purity: 96.1%. $^1$H NMR (400 MHz, DMSO-d$_6$) δ 12.67 (s, 1H), 9.57 (s, 1H), 8.25-8.17 (m, 1H), 7.72 (t, J=7.6 Hz, 1H), 7.65 (ddd, J=7.4, 1.6, 0.8 Hz, 1H), 7.07 (dd, J=2.2, 0.9 Hz, 1H), 6.99 (dd, J=8.1, 2.2 Hz, 1H), 6.84 (d, J=8.1 Hz, 1H), 2.16 (s, 3H), 1.92 (s, 3H). $^{13}$C NMR (101 MHz, DMSO) δ 159.34, 155.55, 146.61, 136.97, 136.13, 131.06, 131.04, 130.03, 128.94, 128.46, 127.23, 124.27, 123.75, 114.24, 22.95, 15.89.

8-(4-Ethoxyl-3,5-dimethylphenyl)-pyrido[2,3-d]pyridazin-5(6H)-one (35)

General procedure C was applied using 2,3-pyridinedicarboxylic anhydride (100 mg, 0.68 mmol), 2,6-dimethylphenol (96 mg, 0.70 mmol), aluminum chloride (185 mg, 1.39 mmol), and hydrazine monohydrate (150 μL, 3.13 mmol). Product was obtained as light yellow solid (122 mg, 67%). ESI-MS m/z: 268.1091 [M+H]$^+$; Purity: 99.9%. $^1$H NMR (400 MHz, DMSO-d$_6$) δ 12.98 (s, 1H), 9.16 (dd, J=4.5, 1.8 Hz, 1H), 8.64 (dd, J=8.1, 1.8 Hz, 1H), 7.86 (dd, J=8.1, 4.5 Hz, 1H), 7.44 (s, 2H), 2.23 (s, 6H). $^{13}$C NMR (101 MHz, DMSO) δ 160.10, 155.54, 154.48, 146.89, 146.05, 135.04, 130.48, 126.52, 125.92, 124.78, 123.79, 17.24.

4-(3,5-Dimethyl-4-Hydroxyphenyl)quinoline (36) General procedure B was applied using 4-bromo-quinoline (104 mg, 0.50 mmol), 2,6-dimethyl-4-(4,4,5,5-tetramethyl-1,3,2-dioxaborolan-2-yl)-phenol (117 mg, 0.50 mmol), K$_2$CO$_3$ (207 mg, 1.50 mmol) and [1,1'-bis(diphenylphosphino)ferrocene]palladium(II) dichloride (20 mg, 0.03 mmol), to give light yellow solid (40 mg, 32%). ESI-MS m/z: 250.1239 [M+H]$^+$; Purity: 99.9%. $^1$H NMR (400 MHz, Chloroform-d) δ 8.91 (dd, J=4.4, 1.0 Hz, 1H), 8.16 (d, J=8.5 Hz, 1H), 8.00 (d, J=8.5 Hz, 1H), 7.72 (ddt, J=8.2, 6.8, 1.2 Hz, 1H), 7.51 (ddt, J=8.2, 6.8, 1.1 Hz, 1H), 7.30 (dd, J=4.5, 0.9 Hz, 1H), 7.15 (s, 2H), 2.32 (s, 6H). $^{13}$C NMR (101 MHz, CDCl$_3$) δ 156.64, 152.80, 150.09, 148.82, 148.73, 129.99, 129.87, 129.33, 127.17, 126.54, 126.26, 123.44, 121.39, 16.21.

4-(3-Methyl-4-Hydroxyphenyl)quinoline (37)

General procedure B was applied using 4-bromo-quinoline (104 mg, 0.50 mmol), 2-methyl-4-(4,4,5,5-tetramethyl-1,3,2-dioxaborolan-2-yl)-phenol (110 mg, 0.50 mmol), K$_2$CO$_3$ (207 mg, 1.50 mmol) and [1,1'-bis(diphenylphosphino)ferrocene]palladium(II) dichloride (21 mg, 0.03 mmol), to give light yellow solid (92 mg, 74% yield). ESI-MS m/z: 236.1073 [M+H]$^+$; Purity: 97.2%. $^1$H NMR (400 MHz, DMSO-d$_6$) δ 8.87 (d, J=4.4 Hz, 1H), 8.06 (dd, J=8.5, 1.2 Hz, 1H), 7.96 (dd, J=8.6, 1.3 Hz, 1H), 7.76 (ddd, J=8.4, 6.8, 1.4 Hz, 1H), 7.58 (ddd, J=8.3, 6.8, 1.4 Hz, 1H), 7.38 (d, J=4.5 Hz, 1H), 7.27 (dd, J=2.3, 0.9 Hz, 1H), 7.20 (dd, J=8.2, 2.4 Hz, 1H), 6.96 (d, J=8.2 Hz, 1H), 2.20 (s, 3H). $^{13}$C NMR (101 MHz, DMSO) δ 156.18, 150.25, 148.37, 147.96, 131.93, 129.56, 129.48, 128.24, 127.88, 126.85, 126.34, 125.86, 124.60, 121.39, 114.93, 16.20.

4-Chloroquinazoline (108)

4-Quinazolinol (292 mg, 2.00 mmol) was refluxed in POCl$_3$ overnight. It was cooled to room temperature and poured into ice water, neutralized with Na$_2$CO$_3$. The precipitation was filtered out and washed with water, dried by pulling air through. Product was obtained as light yellow solid. (224 mg, 68% yield). $^1$H NMR (400 MHz, Chloroform-d) δ 9.06 (s, 1H), 8.30 (ddd, J=8.4, 1.4, 0.7 Hz, 1H), 8.15-8.07 (m, 1H), 7.99 (ddd, J=8.5, 7.0, 1.4 Hz, 1H), 7.76 (ddd, J=8.3, 6.9, 1.2 Hz, 1H).

4-(3-Methyl-4-Hydroxyphenyl)quinazoline (38)

General procedure B was applied using 4-chloroquinazoline (82 mg, 0.50 mmol), 2-methyl-4-(4,4,5,5-tetramethyl-1,3,2-dioxaborolan-2-yl)-phenol (117 mg, 0.50 mmol), K$_2$CO$_3$ (208 mg, 1.50 mmol) and [1,1'-bis(diphenylphosphino)ferrocene]palladium(II) dichloride (19 mg, 0.03 mmol), to give light yellow solid (88 mg, 75% yield). ESI-MS m/z: 237.1034 [M+H]$^+$; Purity: 74.7%. $^1$H NMR (400 MHz, DMSO-d$_6$) δ 9.99 (s, 1H), 9.25 (s, 1H), 8.19 (ddd, J=8.5, 1.3, 0.7 Hz, 1H), 8.07-7.96 (m, 2H), 7.73 (ddd, J=8.3, 6.6, 1.6 Hz, 1H), 7.59 (dd, J=2.3, 0.9 Hz, 1H), 7.51 (ddd, J=8.3, 2.4, 0.6 Hz, 1H), 7.00 (d, J=8.3 Hz, 1H), 2.24 (s, 3H). $^{13}$C NMR (101 MHz, DMSO) δ 167.29, 157.69, 154.33, 150.54, 133.83, 132.62, 129.27, 128.31, 127.95, 127.26, 127.10, 124.34, 122.22, 114.55, 16.01.

4-Isoquinolin-4-yl-2-methylphenol (39)

General procedure B was applied using 4-bromoisoquinoline (105 mg, 0.50 mmol), 2-methyl-4-(4,4,5,5-tetramethyl-1,3,2-dioxaborolan-2-yl)-phenol (117 mg, 0.50 mmol), $K_2CO_3$ (208 mg, 1.50 mmol) and [1,1'-bis(diphenylphosphino)ferrocene]palladium(II) dichloride (19 mg, 0.03 mmol), to give light yellow solid (78 mg, 66% yield). ESI-MS m/z: 236.1077 [M+H]$^+$; Purity: 98.4%. $^1$H NMR (400 MHz, DMSO-d$_6$) δ 9.27 (s, 1H), 8.36 (s, 1H), 8.18 (ddd, J=8.1, 1.5, 0.7 Hz, 1H), 7.90 (dt, J=8.5, 1.0 Hz, 1H), 7.74 (dddd, J=28.7, 8.0, 6.9, 1.3 Hz, 2H), 7.24 (dd, J=2.3, 0.9 Hz, 1H), 7.16 (dd, J=8.2, 2.3 Hz, 1H), 6.95 (d, J=8.2 Hz, 1H), 2.20 (s, 3H). $^{13}$C NMR (101 MHz, DMSO) δ 155.66, 151.34, 142.36, 133.61, 132.96, 132.27, 131.04, 128.48, 128.28, 128.19, 127.55, 126.87, 124.53, 124.50, 114.99, 16.25.

1-Chlorophthalazine (109)

1-Hydroxy-2,3-benzodiazine (300 mg, 2.05 mmol) was refluxed in POCl$_3$ overnight. It was cooled to room temperature and poured into ice water, neutralized with Na$_2$CO$_3$. The precipitation was filtered out and washed with water, dried by pulling air through. Product was obtained as light yellow solid (242 mg, 73% yield). $^1$H NMR (400 MHz, Chloroform-d) δ 9.45 (d, J=0.9 Hz, 1H), 8.37-8.29 (m, 1H), 8.09-7.97 (m, 3H). 1-(3,5-Dimethyl-4-Hydroxyphenyl)-phthalazine (40) General procedure B was applied using 1-chlorophthalazine (83 mg, 0.50 mmol), 2,6-dimethyl-4-(4,4,5,5-tetramethyl-1,3,2-dioxaborolan-2-yl)-phenol (117 mg, 0.50 mmol), Cs$_2$CO$_3$ (489 mg, 1.50 mmol) and [1,1'-bis(diphenylphosphino)ferrocene]palladium(II) dichloride (20 mg, 0.03 mmol), to give light yellow solid (50 mg, 40%). ESI-MS m/z: 251.1183 [M+H]$^+$; Purity: 99.9%. $^1$H NMR (400 MHz, Chloroform-d) δ 9.49 (d, J=0.9 Hz, 1H), 8.20-8.11 (m, 1H), 8.03-7.99 (m, 1H), 7.95-7.85 (m, 2H), 7.35 (s, 2H), 2.33 (s, 6H). $^{13}$C NMR (101 MHz, CDCl$_3$) δ 160.21, 154.08, 150.29, 132.60, 132.27, 130.37, 127.69, 127.29, 126.81, 126.68, 125.81, 124.26, 16.41.

1-(3-Methyl-4-Hydroxyphenyl)-phthalazine (41)

General procedure B was applied using 1-chlorophthalazine (33 mg, 0.20 mmol), 2-methyl-4-(4,4,5,5-tetramethyl-1,3,2-dioxaborolan-2-yl)-phenol (47 mg, 0.20 mmol), K$_2$CO$_3$ (84 mg, 0.60 mmol) and [1,1'-bis(diphenylphosphino)ferrocene]palladium(II) dichloride (9 mg, 0.01 mmol), to give light yellow solid (31 mg, 66%). ESI-MS m/z: 237.1029 [M+H]$^+$; Purity: 94.3%. $^1$H NMR (400 MHz, DMSO-d$_6$) δ 9.81 (s, 1H), 9.62 (s, 1H), 8.21 (d, J=7.6 Hz, 1H), 8.13-7.91 (m, 3H), 7.48 (d, J=2.1 Hz, 1H), 7.40 (dd, J=8.2, 2.3 Hz, 1H), 7.00 (d, J=8.2 Hz, 1H), 2.24 (s, 3H). $^{13}$C NMR (101 MHz, DMSO) δ 158.90, 156.71, 149.92, 133.01, 132.38, 132.28, 128.67, 126.87, 126.58, 126.52, 125.71, 124.41, 124.15, 114.51, 16.01.

1-(4-Hydroxy-3,5-dimethylphenyl)naphthalene (42)

General procedure B was applied using 1-Bromonaphthalene (104 mg, 0.50 mmol), 2,6-dimethyl-4-(4,4,5,5-tetramethyl-1,3,2-dioxaborolan-2-yl)-phenol (117 mg, 0.50 mmol), K$_2$CO$_3$ (207 mg, 1.50 mmol) and [1,1'-bis(diphenylphosphino)ferrocene]palladium(II) dichloride (20 mg, 0.03 mmol), to give light yellow solid (67 mg, 54%). ESI-MS m/z: 247.1123 [M−H]$^−$; Purity: 90.0%. $^1$H NMR (400 MHz, Chloroform-d) δ 7.95 (ddt, J=8.3, 1.6, 0.8 Hz, 1H), 7.89 (ddt, J=8.1, 1.3, 0.6 Hz, TH), 7.82 (dd, J=8.3, 1.2 Hz, 1H), 7.54-7.37 (m, 4H), 7.12 (s, 2H), 2.34 (s, 6H). $^{13}$C NMR (101 MHz, CDCl$_3$) δ 151.58, 140.17, 133.81, 132.71, 131.85, 130.25, 128.22, 127.16, 126.81, 126.23, 125.82, 125.63, 125.38, 122.78, 16.04.

1-(4-Hydroxy-3-methylphenyl)naphthalene (43)

General procedure B was applied using 1-Bromonaphthalene (104 mg, 0.50 mmol), 2-methyl-4-(4,4,5,5-tetramethyl-1,3,2-dioxaborolan-2-yl)-phenol (110 mg, 0.50 mmol), K$_2$CO$_3$ (207 mg, 1.50 mmol) and [1,1'-bis(diphenylphosphino)ferrocene]palladium(I) dichloride (21 mg, 0.03 mmol), to give light yellow solid (82 mg, 65% yield). ESI-MS m/z: 235.1118 [M+H]$^+$; Purity: 95.9%. $^1$H NMR (400 MHz, Chloroform-d) δ 7.98-7.86 (m, 2H), 7.87-7.80 (m, 1H), 7.56-7.35 (m, 4H), 7.31-7.23 (m, 1H), 7.22 (dd, J=8.1, 2.2 Hz, 1H), 6.90 (d, J=8.1 Hz, 1H), 2.34 (s, 3H). $^{13}$C NMR (101 MHz, CDCl$_3$) δ 153.33, 140.14, 133.95, 133.36, 132.81, 131.96, 128.88, 128.37, 127.38, 126.98, 126.27, 126.00, 125.80, 125.52, 123.69, 114.85, 16.01.

Cinnolin-4-ol (110)

A mixture of 2-aminoacetophenone (295 μL, 1.55 mol) in concentrated HCl (2 mL) is cooled to −5° C. A solution of sodium nitrite (129 g, 1.87 mol) in water (5 mL) is added slowly maintaining the temperature below 0° C. After that the mixture is stirred at 65° C. for 3 h. The mixture is cooled to room temperature. The precipitate is filtered off, washed with ether, dried and dissolved in water (minimal amount). Sodium hydrocarbonate (1 g) is carefully added to the solution, the mixture is stirred for 1 h and filtered. The precipitate is washed with water and dried on air to give of the title compound (218 mg, 96% yield). $^1$H NMR (400 MHz, Methanol-d$_4$) δ 8.18 (ddd, J=8.3, 1.4, 0.7 Hz, 1H), 7.86 (s, TH), 7.83 (ddd, J=8.5, 6.9, 1.4 Hz, 1H), 7.64 (dt, J=8.6, 0.9 Hz, 1H), 7.50 (ddd, J=8.1, 7.0, 1.0 Hz, 1H).

4-Chlorocinnoline (111)

Compound 110 (292 mg, 2.00 mmol) was refluxed in POCl$_3$ overnight. It was cooled to room temperature and poured into ice water, neutralized with Na$_2$CO$_3$. The precipitation was filtered out and washed with water, dried by pulling air through. Product was obtained as light yellow solid. (243 mg, 74%). $^1$H NMR (400 MHz, Chloroform-d) δ 9.35 (s, 1H), 8.57 (ddd, J=8.5, 1.4, 0.7 Hz, 1H), 8.20 (ddd, J=8.2, 1.6, 0.7 Hz, 1H), 7.97-7.83 (m, 2H).

4-(4-Hydroxy-3,5-dimethylphenyl)-cinnolin (44)

General procedure B was applied using 110 (146 mg, 0.89 mmol), 2,6-dimethyl-4-(4,4,5,5-tetramethyl-1,3,2-dioxaborolan-2-yl)-phenol (208 mg, 0.89 mmol), K$_2$CO$_3$ (368 mg, 2.66 mmol) and [1,1'-bis(diphenylphosphino)ferrocene]palladium(II) dichloride (37 mg, 0.05 mmol), to give light yellow solid (132 mg, 59% yield). ESI-MS m/z: 523.2110 [2M+Na]$^+$; Purity: 90.7%. $^1$H NMR (400 MHz, Chloroform-d) δ 9.24 (s, 1H), 8.62-8.54 (m, 1H), 8.12-8.01 (m, 1H), 7.85 (ddd, J=8.5, 6.8, 1.4 Hz, 1H), 7.73 (ddd, J=8.3, 6.8, 1.3 Hz, 1H), 7.21 (s, 2H), 2.38 (s, 6H). $^{13}$C NMR (101

MHz, CDCl₃) δ 153.61, 150.68, 144.85, 135.49, 131.07, 130.37, 130.31, 130.20, 126.06, 125.10, 124.04, 124.04, 16.24.

4-(4-Hydroxy-3-methylphenyl)-cinnolin (45)

General procedure B was applied using 111 (50 mg, 0.30 mmol), 2-methyl-4-(4,4,5,5-tetramethyl-1,3,2-dioxaborolan-2-yl)-phenol (72 mg, 0.31 mmol), K₂CO₃ (125 mg, 0.90 mmol) and [1,1'-bis(diphenylphosphino)ferrocene]palladium(II) dichloride (13 mg, 0.02 mmol), to give light yellow solid (51 mg, 72% yield). ESI-MS m/z: 237.1031 [M+H]⁺; Purity: 99.9%. ¹H NMR (400 MHz, DMSO-d₆) δ 9.90 (s, 1H), 9.27 (s, 1H), 8.50 (ddd, J=8.5, 1.3, 0.7 Hz, 1H), 8.08 (ddd, J=8.5, 1.4, 0.7 Hz, 1H), 7.97 (ddd, J=8.4, 6.8, 1.4 Hz, 1H), 7.87 (ddd, J=8.2, 6.8, 1.3 Hz, 1H), 7.42 (dd, J=2.4, 0.9 Hz, 1H), 7.34 (ddd, J=8.3, 2.4, 0.7 Hz, 1H), 7.02 (d, J=8.2 Hz, 1H), 2.23 (s, 3H). ¹³C NMR (101 MHz, DMSO) δ 156.83, 149.95, 144.27, 134.59, 132.24, 131.46, 130.74, 129.36, 128.75, 124.91, 124.80, 123.82, 123.65, 115.13, 16.02.

N-tert-butoxycarbonyl-3-(4-Hydroxy-3-methylphenyl)-indole (46)

General procedure B was applied using 3-bromoindole-1-carboxylic acid tert-butyl ester (150 mg, 0.51 mmol), 2-methyl-4-(4,4,5,5-tetramethyl-1,3,2-dioxaborolan-2-yl)-phenol (117 mg, 0.50 mmol), K₂CO₃ (207 mg, 1.50 mmol) and [1,1'-bis(diphenylphosphino)ferrocene]palladium(II) dichloride (20 mg, 0.02 mmol), to give light yellow solid (132 mg, 82%) ESI-MS m/z: 324.1610 [M+H]⁺; Purity: 92.2%. ¹H NMR (400 MHz, Chloroform-d) δ 8.26-8.15 (m, 1H), 7.78 (ddd, J=7.8, 1.4, 0.7 Hz, 1H), 7.63 (s, 1H), 7.41 (m, 1H), 7.39-7.34 (m, 2H), 7.32-7.26 (m, 1H), 6.88 (d, J=8.2 Hz, 1H), 2.34 (s, 3H), 1.69 (s, 9H). ¹³C NMR (101 MHz, CDCl₃) δ 153.32, 135.93, 134.46, 130.77, 129.37, 126.85, 126.48, 124.61, 124.32, 122.94, 122.27, 122.08, 120.08, 115.53, 115.42, 83.86, 28.39, 16.05.

3-(4-Hydroxy-3-methylphenyl)-indole (47)

Compound 46 (32 mg 0.10 mmol) was dissolved in chloroform in ice bath, TFA was added dropwise, and stirred in ice bath for 2 h. The mixture was then diluted with water and adjusted to pH 6 with NaHCO₃ and extracted with ethyl acetate. The combined organic layers were dried over magnesium sulfate, filtered and concentrated. The residue was purified by flash column chromatography on silica gel (eluent: dichloromethane/methanol, 0-20%) to give the title compound as a light yellow solid (14 mg, 63% yield). ESI-MS m/z: 224.1074 [M+H]⁺; Purity: 94.2%. ¹H NMR (400 MHz, Chloroform-d) δ 8.18 (s, 1H), 7.90 (ddt, J=7.9, 1.6, 0.8 Hz, 1H), 7.46-7.39 (m, 2H), 7.39 (ddd, J=8.2, 2.2, 0.6 Hz, 1H), 7.29 (d, J=2.5 Hz, 1H), 7.26-7.21 (m, 1H), 7.18 (ddd, J=8.0, 7.0, 1.1 Hz, 1H), 6.87 (d, J=8.2 Hz, 1H), 2.33 (s, 3H). ¹³C NMR (101 MHz, CDCl₃) δ 152.32, 136.54, 130.27, 128.14, 126.29, 125.91, 124.00, 122.28, 121.06, 120.08, 119.78, 118.12, 115.27, 111.31, 15.95.

3-(4-Hydroxy-3-methylphenyl)-1H-indazole (48)

General procedure B was applied using 3-bromo-1H-indazole (125 mg, 0.60 mmol), 2-methyl-4-(4,4,5,5-tetramethyl-1,3,2-dioxaborolan-2-yl)-phenol (117 mg, 0.50 mmol), K₃PO₄ (531 mg, 2.50 mmol) and [1,1'-bis(diphenylphosphino)ferrocene]palladium(II) dichloride (19 mg, 0.03 mmol), to give light yellow solid (97 mg, 86% yield). ESI-MS m/z: 225.1033 [M+H]⁺; Purity: 99.6%. ¹H NMR (400 MHz, Chloroform-d) δ 8.01 (dt, J=8.2, 1.0 Hz, 1H), 7.76 (dd, J=2.1, 0.9 Hz, 1H), 7.71-7.66 (m, 1H), 7.49 (dt, J=8.4, 1.0 Hz, 1H), 7.42 (ddd, J=8.4, 6.8, 1.0 Hz, 1H), 7.22 (ddd, J=8.0, 6.8, 1.0 Hz, 1H), 6.92 (d, J=8.2 Hz, 1H), 2.36 (s, 3H). ¹³C NMR (101 MHz, CDCl₃) δ 154.28, 146.03, 141.78, 130.44, 126.96, 126.61, 126.22, 124.50, 121.49, 121.34, 121.11, 115.47, 110.03, 25.02.

4-(4-Hydroxyl-3-methylphenyl)-7-azaindole (49)

General procedure B was applied using 4-chloro-7-azaindole (34 mg, 0.22 mmol), 2-methyl-4-(4,4,5,5-tetramethyl-1,3,2-dioxaborolan-2-yl)-phenol (47 mg, 0.20 mmol), K₂CO₃ (84 mg, 0.60 mmol) and [1,1'-bis(diphenylphosphino)ferrocene]palladium(II) dichloride 0) (9 mg, 0.01 mmol), to give light yellow solid (33 mg, 62%). ESI-MS m/z: 225.1029 [M+H]⁺; Purity: 96.5%. ¹H NMR (400 MHz, DMSO-d₆) δ 11.68 (s, 1H), 9.63 (s, 1H), 8.20 (d, J=4.9 Hz, 1H), 7.52-7.46 (m, 2H), 7.44 (dd, J=8.2, 2.4 Hz, 1H), 7.08 (d, J=4.9 Hz, 1H), 6.93 (d, J=8.3 Hz, 1H), 6.60 (dd, J=3.5, 1.9 Hz, 1H), 2.22 (s, 3H). ¹³C NMR (101 MHz, DMSO) δ 155.91, 149.13, 142.80, 140.61, 130.45, 129.04, 126.71, 125.90, 124.39, 116.97, 114.97, 113.54, 99.26, 16.09.

2,2-Dimethyl-5-((pyridin-3-ylamino)methylene)-1,3-dioxane-4,6-dione (112)

A mixture of triethyl orthoformate (1.665 mL, 10.0 mmol) and 2,2-dimethyl-1,3-dioxane-4,6-dione (865 mg, 6.0 mmol) was heated at 90° C. for 1.5 h and then cooled to 70° C. 3-Amino-pyridine 15 (471 mg, 5.0 mol) was slowly added over 10 min with an EtOH (20 mL) rinse while maintaining the reaction temperature between 60 and 70° C. The reaction was then heated for an additional 30 min and allowed to cool to RT. The precipitate was filtered, washed with EtOH (20 mL), and dried to yield compound as a light-yellow solid (1118 mg, 90%). ¹H NMR (400 MHz, chloroform-d) δ 11.25 (d, J=14.2 Hz, 1H), 8.66-8.59 (m, 2H), 8.55 (dd, J=4.8, 1.4 Hz, 1H), 7.61 (ddd, J=8.3, 2.8, 1.4 Hz, 1H), 7.41 (dd, J=8.3, 4.7 Hz, 1H), 1.77 (s, 6H).

4-Hydroxy-1,5-naphthyridine (113)

Intermediate 112 (300 mg, 1.21 mmol) was added portion wise to diphenyl ether (100 ml, 630 mmol) at 215° C. The solution was stirred at reflux for 4 h and then cooled to room temperature. The combined precipitated solid were filtered off and washed with diethyl ether (2×500 ml) to give a pale brown solid. The solid was triturated in diethyl ether (2×500 ml), filtered off and dried under vacuum to give of intermediate 2, that was used without further purification for the next step. (78 mg, 44% yield). ¹H NMR (400 MHz, Methanol-d₄) δ 8.75 (dd, J=4.3, 1.5 Hz, 1H), 8.15-8.01 (m, 2H), 7.74 (dd, J=8.6, 4.2 Hz, 1H), 6.52 (d, J=7.4 Hz, 1H).

4-Chloro-1,5-naphthyridine (114)

Compound 113 (78 mg, 0.53 mmol) was stirred in POCl₃ (5 mL) at 90° C. overnight. The reaction was then quenched with saturated sodium carbonate solution and extracted with ethyl acetate (50 mL×3). The combined organic layers were dried over magnesium sulfate, filtered and concentrated. The residue was purified by flash column chromatography on silica gel (eluent: dichloromethane/ethyl acetate, 10-100%) to give the title compound as a white solid (43 mg, 49%). ¹H NMR (400 MHz, Chloroform-d) δ 9.12 (dd, J=4.1, 1.6 Hz, 1H), 8.89 (s, br, 1H), 8.50 (dd, J=8.5, 1.6 Hz, 1H), 7.81 (d, J=4.7 Hz, 1H), 7.76 (dd, J=8.5, 4.1 Hz, 1H).

4-(4-Hydroxyl-3-methylphenyl)-1,5-naphthyridine (50)

General procedure B was applied using 113 (30 mg, 0.18 mmol), 2-methyl-4-(4,4,5,5-tetramethyl-1,3,2-dioxaborolan-2-yl)-phenol (43 mg, 0.18 mmol), $K_2CO_3$ (76 mg, 0.55 mmol) and [1,1'-bis(diphenylphosphino)ferrocene]palladium(II) dichloride (8 mg, 0.01 mmol), to give light yellow solid (21 mg, 49%). ESI-MS m/z: 237.1032 [M+H]$^+$; Purity: 99.6%. $^1$H NMR (400 MHz, DMSO-d$_6$) δ 9.67 (s, 1H), 9.01 (dd, J=4.1, 1.8 Hz, 1H), 8.96 (d, J=4.5 Hz, 1H), 8.44 (dd, J=8.5, 1.8 Hz, 1H), 7.79 (dd, J=8.5, 4.1 Hz, 1H), 7.72 (d, J=4.5 Hz, 1H), 7.58 (dd, J=2.3, 0.9 Hz, 1H), 7.52 (ddd, J=8.3, 2.4, 0.6 Hz, 1H), 6.92 (d, J=8.3 Hz, 1H), 2.21 (s, 3H). $^{13}$C NMR (101 MHz, DMSO) δ 156.28, 151.11, 150.55, 147.13, 143.94, 141.28, 137.33, 133.05, 129.47, 126.77, 124.41, 123.47, 123.42, 114.23, 16.14.

4-(4-Hydroxy-3,5-dimethylphenyl)-2-methyl-quinoline (51)

General procedure B was applied using 4-bromo-2-methoxylquinoline (80 mg, 0.45 mmol), 2,6-dimethyl-4-(4,4,5,5-tetramethyl-1,3,2-dioxaborolan-2-yl)-phenol (105 mg, 0.45 mmol), $K_2CO_3$ (187 mg, 1.35 mmol) and [1,1'-bis(diphenylphosphino)ferrocene]palladium(II) dichloride (20 mg, 0.03 mmol), to give light yellow solid (62 mg, 52%). ESI-MS m/z: 264.1388 [M+H]$^+$; Purity: 87.8%. $^1$H NMR (400 MHz, Chloroform-d) δ 8.06 (d, J=8.5 Hz, 1H), 7.97-7.90 (m, 1H), 7.70-7.64 (m, 1H), 7.47-7.39 (m, 1H), 7.20 (s, 1H), 7.15-7.12 (m, 2H), 4.88 (s, 1H), 2.76 (s, 3H), 2.34 (d, J=0.7 Hz, 6H). $^{13}$C NMR (101 MHz, CDCl$_3$) δ 158.59, 152.74, 148.76, 148.52, 130.12, 129.92, 129.33, 129.02, 126.03, 125.66, 125.49, 123.45, 122.28, 25.47, 16.22.

4-(4-Hydroxy-3,5-dimethylphenyl)-2-trifluoromethyl-quinoline (52)

General procedure B was applied using 4-chloro-2-trifluoromethoxylquinoline (116 mg, 0.50 mmol), 2,6-dimethyl-4-(4,4,5,5-tetramethyl-1,3,2-dioxaborolan-2-yl)-phenol (117 mg, 0.50 mmol), $K_2CO_3$ (207 mg, 1.50 mmol) and [1,1'-bis(diphenylphosphino)ferrocene]palladium(II) dichloride (21 mg, 0.03 mmol), to give light yellow solid (132 mg, 59%). ESI-MS m/z: 318.1107 [M+H]$^+$; Purity: 89.4%. $^1$H NMR (400 MHz, Chloroform-d) δ 8.31-8.23 (m, 1H), 8.11-8.03 (m, 1H), 7.81 (ddd, J=8.4, 6.8, 1.4 Hz, 1H), 7.67-7.58 (m, 2H), 7.17 (s, 2H), 4.86 (s, 1H), 2.36 (s, 6H). $^{13}$C NMR (101 MHz, CDCl$_3$) δ 153.23, 151.14, 147.96, 147.80, 130.57, 130.54, 129.99, 129.18, 128.47, 127.78, 126.29, 123.67, 123.21, 117.01, 116.99, 16.15.4-(4-Hydroxy-3-methylphenyl)-2-methyl-quinoline (53) General procedure B was applied using 4-bromo-2-methoxylquinoline (89 mg, 0.50 mmol), 2-methyl-4-(4,4,5,5-tetramethyl-1,3,2-dioxaborolan-2-yl)-phenol (110 mg, 0.50 mmol), $K_2CO_3$ (207 mg, 1.50 mmol) and 1,1'-bis(diphenylphosphino)ferrocene]palladium(II) dichloride (21 mg, 0.03 mmol), to give light yellow solid (81 mg, 65% yield). ESI-MS m/z: 250.1232 [M+H]$^+$; Purity: 97.8%. $^1$H NMR (400 MHz, DMSO-d$_6$) δ 8.00-7.92 (m, 1H), 7.92-7.86 (m, 1H), 7.70 (ddd, J=8.3, 6.8, 1.4 Hz, 1H), 7.49 (ddd, J=8.3, 6.8, 1.3 Hz, 1H), 7.27 (s, 1H), 7.25 (dd, J=2.3, 0.9 Hz, 1H), 7.22-7.14 (m, 1H), 6.95 (d, J=8.2 Hz, 1H), 2.65 (s, 3H), 2.20 (s, 3H). $^{13}$C NMR (101 MHz, DMSO) δ 158.49, 156.07, 148.06, 148.00, 131.86, 129.35, 128.80, 128.15, 128.00, 125.89, 125.60, 124.75, 124.54, 122.02, 114.86, 24.88, 16.19.

4-(4-Hydroxy-3-methylphenyl)-2-trifluoromethyl-quinoline (54)

General procedure B was applied using 4-chloro-2-trifluoromethoxylquinoline (231 mg, 1.00 mmol), 2-methyl-4-(4,4,5,5-tetramethyl-1,3,2-dioxaborolan-2-yl)-phenol (234 mg, 1.00 mmol), $K_2CO_3$ (415 mg, 3.00 mmol) and [1,1'-bis(diphenylphosphino)ferrocene]palladium(II) dichloride (36 mg, 0.05 mmol), to give light yellow solid (231 mg, 76%). ESI-MS m/z: 304.0953 [M+H]$^+$; Purity: 96.8%. $^1$H NMR (400 MHz, Chloroform-d) δ 8.29 (ddd, J=8.5, 1.3, 0.6 Hz, 1H), 8.07 (ddd, J=8.5, 1.5, 0.6 Hz, 1H), 7.82 (ddd, J=8.4, 6.8, 1.4 Hz, 1H), 7.66 (s, 1H), 7.63 (ddd, J=8.3, 6.8, 1.3 Hz, 1H), 7.32 (dd, J=2.3, 0.9 Hz, 1H), 7.29-7.23 (m, 1H), 6.97 (d, J=8.2 Hz, 1H), 2.38 (s, 3H). $^{13}$C NMR (101 MHz, CDCl$_3$) δ 155.00, 151.12, 147.92, 147.79, 132.40, 130.67, 130.47, 129.56, 128.65, 128.57, 127.78, 126.23, 124.75, 123.19, 117.04, 115.36, 16.04.

4-(4-Hydroxy-3-methylphenyl)-2-methoxyl-quinoline (55)

General procedure B was applied using 4-chloro-2-methoxylquinoline (40 mg, 0.21 mmol), 2-methyl-4-(4,4,5,5-tetramethyl-1,3,2-dioxaborolan-2-yl)-phenol (47 mg, 0.20 mmol), $K_2CO_3$ (84 mg, 0.60 mmol) and [1,1'-bis(diphenylphosphino)ferrocene]dichloropalladium (II), complex with dichloromethane (9 mg, 0.01 mmol), to give light yellow solid (33 mg, 62%). ESI-MS m/z: 266.1181 [M+H]$^+$; Purity: 85.6%. $^1$H NMR (400 MHz, Chloroform-d) δ 7.93 (ddd, J=8.4, 1.4, 0.6 Hz, 1H), 7.85-7.80 (m, 1H), 7.62 (ddd, J=8.4, 6.9, 1.5 Hz, 1H), 7.33 (ddd, J=8.3, 6.9, 1.3 Hz, 1H), 7.27 (dd, J=2.3, 0.9 Hz, 1H), 7.21 (ddd, J=8.1, 2.2, 0.6 Hz, 1H), 6.91 (d, J=8.1 Hz, 1H), 6.83 (d, J=1.2 Hz, 1H), 4.11 (s, 3H), 2.34 (s, 3H). $^{13}$C NMR (101 MHz, CDCl$_3$) δ 162.33, 154.37, 151.26, 147.31, 132.22, 130.45, 129.53, 128.35, 127.62, 126.09, 124.43, 124.24, 124.03, 115.04, 112.73, 53.58, 16.03.

3-Methylquinolin-4-ol (115)

3-methylquinoline (286 mg, 2.00 mmol) was dissolved in acetic acid, and 30% hydroperoxide (680 uL, 6.00 mmol) was added. These reactants were mixed and stirred at 60° C. overnight, cooled to room temperature, neutralized with $Na_2CO_3$ solution. 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give light yellow solid (243 mg, 76%). $^1$H NMR (400 MHz, Chloroform-d) δ 8.75-8.66 (m, 1H), 8.50 (s, 1H), 7.79 (dd, J=8.2, 1.4 Hz, 1H), 7.70 (ddt, J=8.6, 6.9, 1.4 Hz, 1H), 7.66-7.57 (m, 1H), 2.47 (s, 3H).

4-Chloro-3-methylquinoline (116)

3-methylquinolin-4-ol (200 mg, 1.25 mmol) was refluxed in $POCl_3$ overnight. It was cooled to room temperature and poured into ice water, neutralized with $Na_2CO_3$. The precipitation was filtered out and washed with water, dried by pulling air through. Product was obtained as light yellow solid (142 mg, 64%). $^1$H NMR (400 MHz, Chloroform-d) δ 8.03-7.96 (m, 2H), 7.78-7.73 (m, 1H), 7.70-7.65 (m, 1H), 7.53 (ddt, J=8.1, 7.0, 1.1 Hz, 1H), 2.54 (d, J=1.0 Hz, 3H).

4-(4-Hydroxy-3-methylphenyl)-3-methyl-quinoline (56)

General procedure B was applied 116 (153 mg, 0.86 mmol), 2-methyl-4-(4,4,5,5-tetramethyl-1,3,2-dioxaborolan-2-yl)-phenol (201 mg, 0.86 mmol), K$_2$CO$_3$ (357 mg, 2.58 mmol) and tetrakis (triphenylphosphine)palladium(0) (36 mg, 0.05 mmol), to give light yellow solid (121 mg, 56%). ESI-MS m/z: 250.1228 [M+H]$^+$; Purity: 92.5%. $^1$H NMR (400 MHz, Chloroform-d) δ 8.17 (dd, J=8.5, 0.9 Hz, 1H), 8.02 (t, J=1.0 Hz, 1H), 7.78 (dd, J=8.0, 1.4 Hz, 1H), 7.67 (ddd, J=8.4, 6.9, 1.5 Hz, 1H), 7.52 (ddd, J=8.1, 6.9, 1.2 Hz, 1H), 7.30 (dd, J=2.2, 0.9 Hz, 1H), 7.16 (ddd, J=8.2, 2.3, 0.6 Hz, 1H), 6.69 (d, J=8.1 Hz, 1H), 2.47 (s, 3H), 2.28 (s, 3H). $^{13}$C NMR (101 MHz, CDCl$_3$) δ 160.85, 154.77, 146.46, 137.02, 132.79, 131.53, 129.73, 128.98, 128.83, 127.69, 127.63, 126.84, 126.42, 124.82, 115.67, 20.90, 16.24.

Methyl-2-bromo-5-methoxy-4-methylbenzoate (117)

2-Bromo-5-methoxy-4-methyl-benzoic acid (490 mg, 2.00 mmol) was dissolved in 5 ml of methanol in ice bath and then SOCl$_2$ (436 μL, 6.00 mmol) was added dropwise. The reaction mixture was stirred overnight at room temperature. 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give light yellow solid. (436 mg, 84%). $^1$H NMR (400 MHz, Chloroform-d) δ 7.40 (d, J=0.8 Hz, 1H), 7.27 (s, 1H), 3.92 (s, 3H), 3.85 (s, 3H), 2.21 (s, 3H).

2-Methyl-5-carbomethoxyl-4-(4,4,5,5-tetramethyl-[1,3,2]dioxaborolan-2-yl)-anisole (118)

General procedure A was applied using potassium acetate (786 mg, 8.00 mmol), bis-(pinacolato)-diboron (610 mg, 2.40 mmol) and bis(diphenylphosphine) ferrocene dichloropalladium (II) complex with dichloromethane (82 mg, 0.10 mmol) was added to an anhydrous solution of 116 (436 mg g, 1.68 mmol). Product was obtained as white solid (477 mg, 93%). ESI-MS m/z: 329.1532 [M+Na]$^+$; $^1$H NMR (400 MHz, Chloroform-d) δ 7.37 (s, 1H), 7.25 (d, J=0.9 Hz, 1H), 3.90 (s, 3H), 3.86 (s, 3H), 2.23 (d, J=0.8 Hz, 3H), 1.40 (s, 12H). $^{13}$C NMR (101 MHz, CDCl$_3$) δ 168.57, 158.41, 134.68, 132.90, 131.23, 110.20, 83.93, 55.45, 52.30, 25.00, 16.42.

4-(2-Methoxycarbonyl-4-methoxyl-3-methylphenyl)-quinoline (57)

General procedure B was applied using 4-bromo-quinolone (105 mg, 0.50 mmol), 117 (140 mg, 0.51 mmol), K$_2$CO$_3$ (208 mg, 1.51 mmol) and [1,1'-bis(diphenylphosphino)ferrocene]palladium(II) dichloride (21 mg, 0.03 mmol), to give light yellow solid (120 mg, 78%) ESI-MS m/z: 308.1287 [M+H]$^+$; Purity: 98.7%. $^1$H NMR (400 MHz, Chloroform-d) δ 8.92 (d, J=4.4 Hz, 1H), 8.18-8.11 (m, 1H), 7.70-7.64 (m, 1H), 7.55 (s, 1H), 7.50 (ddd, J=8.4, 1.6, 0.8 Hz, 1H), 7.42 (ddd, J=8.3, 6.8, 1.2 Hz, 1H), 7.23 (d, J=4.4 Hz, 1H), 7.11 (s, 1H), 3.97 (s, 3H), 3.35 (s, 3H), 2.30 (s, 3H). $^{13}$C NMR (101 MHz, CDCl$_3$) δ 167.33, 157.70, 149.94, 149.15, 148.11, 133.38, 131.78, 131.11, 129.83, 129.17, 128.96, 127.86, 126.56, 125.65, 120.95, 111.47, 55.82, 51.92, 16.50.

4-(2-Methoxycarbonyl-4-methoxyl-3-methylphenyl)-7-methoxyl-quinoline (58)

General procedure B was applied using 4-chloro-7-methoxylquinoline (97 mg, 0.50 mmol), 117 (140 mg, 0.51 mmol), K$_2$CO$_3$ (208 mg, 1.51 mmol) and [1,1'-bis(diphenylphosphino) ferrocene]palladium(II) dichloride (20 mg, 0.03 mmol), to give light yellow solid (87 mg, 52%). ESI-MS m/z: 338.1393 [M+H]$^+$; Purity: 99.4%. $^1$H NMR (400 MHz, Chloroform-d) δ 8.82 (d, J=4.5 Hz, 1H), 7.53 (s, 1H), 7.46 (d, J=2.6 Hz, 1H), 7.38 (d, J=9.2 Hz, 1H), 7.14-7.02 (m, 3H), 3.96 (s, 3H), 3.96 (s, 3H), 3.38 (s, 3H), 2.30 (s, 3H). $^{13}$C NMR (101 MHz, CDCl$_3$) δ 167.37, 160.36, 157.64, 150.14, 149.86, 148.93, 133.32, 131.70, 131.26, 128.91, 126.80, 122.95, 119.62, 119.15, 111.42, 107.64, 55.81, 55.63, 51.97, 16.50.

9-Hydroxyl-10-methyl-3-azabenzanthrone (59)

Compound 57 (47 mg, 0.15 mmol) was dissolved in 1 mL sulfuric acid. The reaction mixture was stirred at 120° C. for 2 h, and 140° C. for 3 h, and then cooled to room temperature and poured into ice water, neutralized with Na$_2$CO$_3$. 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give light yellow solid (26 mg, 63%). ESI-MS m/z: 262.0863 [M+H]$^+$; Purity: 94.7%. $^1$H NMR (400 MHz, DMSO-d$_6$) δ 9.08 (d, J=4.8 Hz, 1H), 8.55 (dd, J=7.3, 1.3 Hz, 1H), 8.46-8.38 (m, 3H), 8.03 (dd, J=8.3, 7.3 Hz, 1H), 7.74 (s, 1H), 2.35 (s, 3H). $^{13}$C NMR (101 MHz, DMSO) δ 181.50, 158.24, 151.81, 147.07, 136.12, 134.58, 132.40, 131.20, 129.85, 128.70, 128.28, 127.41, 125.05, 122.29, 116.54, 111.77, 16.52.

5,9-Dihydroxyl-10-methyl-3-azabenzanthrone (60)

Compound 58 (47 mg, 0.15 mmol) was dissolved in 1 mL sulfuric acid. The reaction mixture is stirred at 120 C for 2 h, and 140 C for 3 h, and then cooled to room temperature and poured into ice water, neutralized with Na$_2$CO$_3$. 50 ml of water was added and the aqueous layer was extracted with ethyl acetate (50 mL×3). The combined organic layers were dried over magnesium sulfate, filtered, concentrated in vacuum. The residue was purified by flash column chromatography on silica gel (eluent: dichloromethane/ethyl acetate, 0-10%) to give light yellow solid. (26 mg, 63%). ESI-MS m/z: 276.0666 [M+H]$^+$; Purity: 83.3%. $^1$H NMR (400 MHz, DMSO-d$_6$) δ 10.78 (s, 1H), 10.41 (s, 1H), 8.73 (s, 1H), 8.54 (d, J=9.0 Hz, 1H), 8.09 (s, 1H), 7.28 (d, J=8.8 Hz, 2H), 7.06 (s, 1H), 2.27 (s, 3H). $^{13}$C NMR (101 MHz, DMSO) δ 192.74, 161.89, 158.79, 154.92, 152.00, 144.52, 134.36, 132.38, 131.06, 128.54, 128.15, 122.67, 121.42, 117.03, 111.84, 110.71, 17.07.

4-Chloro-7-methoxy-quinoline (119)

7-Methoxy-4-quinolinol (175 mg, 1.0 mmol) was stirred in POCl$_3$ (5 mL) at 90° C. overnight. The reaction was then quenched with saturated sodium carbonate solution and extracted with ethyl acetate (50 mL×3). The combined organic layers were dried over magnesium sulfate, filtered and concentrated. The residue was purified by flash column chromatography on silica gel (eluent: dichloromethane/ethyl acetate, 10-100%) to give the title compound as a white solid (163 mg, 85%). $^1$H NMR (400 MHz, CDCl$_3$) δ 8.70 (d, J=4.8 Hz, 1H), 8.12 (d, J=9.2 Hz, 1H), 7.43 (d, J=2.5 Hz, 1H), 7.35 (d, J=4.8 Hz, 1H), 7.29 (dd, J=9.2, 2.6 Hz, 1H), 3.97 (s, 3H).

2-Methyl-4-(7-methoxyl-4-quinolinyl)-phenol (61)

A mixture of 4-chloro-7-methoxy-quinolone (80 mg, 0.42 mmol), 2-methyl-4-(4,4,5,5-tetramethyl-1,3,2-dioxaborolan-2-yl)-phenol (97 mg, 0.42 mmol), K$_2$CO$_3$ (158 mg, 1.1 mmol) and [1,1-bis(diphenylphosphino)ferrocene]dichloropalladium (II), complex with dichloromethane (18 mg, 0.01 mmol) in dioxane (5 mL) and H$_2$O (1 mL) was heated at 100° C. overnight in an atmosphere of nitrogen. The reaction was then quenched with water and extracted with ethyl acetate. The combined organic layers were dried over magnesium sulfate, filtered and concentrated. The residue was purified by flash column chromatography on silica gel (eluent: dichloromethane/methanol, 0-10%) to give the title compound as white solid (77 mg, 85%). ESI-MS m/z: 266.1181[M+H]$^+$; Purity: 99.0%. $^1$H NMR (400 MHz, DMSO-d$_6$) δ 9.69 (s, 1H), 8.79 (d, J=4.5 Hz, 1H), 7.85 (d, J=9.3 Hz, 1H), 7.44 (d, J=2.6 Hz, 1H), 7.26-7.20 (m, 3H), 7.20-7.16 (m, 1H), 6.95 (d, J=8.2 Hz, 1H), 3.93 (s, 3H), 2.21 (s, 3H); $^{13}$C NMR (101 MHz, DMSO) δ 159.84, 155.98, 150.27, 150.14, 147.57, 131.66, 127.96, 127.90, 126.93, 124.32, 121.13, 119.20, 119.12, 114.71, 107.77, 55.46, 16.03.

2-Methyl-4-(7-hydroxyl-4-quinolinyl)-phenol (62)

A solution of 61 (80 mg, 0.30 mmol) in anhydrous dichloromethane (7 mL) was cooled in ice bath and treated dropwise with a 1 M solution of BBr$_3$ in dichloromethane (1.9 mL), and the resulting solution was stirred in an ice bath for 30 min and at room temperature for 1 h. The mixture was then diluted with water and adjusted to pH 6 with NaHCO$_3$ and extracted with ethyl acetate. The combined organic layers were dried over magnesium sulfate, filtered and concentrated. The residue was purified by flash column chromatography on silica gel (eluent: dichloromethane/methanol, 0-20%) to give the title compound as a light yellow solid (37 mg, 49%). ESI-MS m/z: 252.1024 [M+H]$^+$; Purity: 95.9%. $^1$H NMR (400 MHz, DMSO-d$_6$) δ 10.15 (s, 1H), 9.66 (s, 1H), 8.71 (d, J=4.5 Hz, 1H), 7.79 (d, J=9.1 Hz, 1H), 7.29 (d, J=2.5 Hz, 1H), 7.25-7.21 (m, 1H), 7.19-7.09 (m, 3H), 6.94 (d, J=8.2 Hz, 1H), 2.20 (s, 3H); $^{13}$C NMR (101 MHz, DMSO-d$_6$) δ 158.14, 155.87, 150.16, 150.07, 147.52, 131.60, 128.12, 127.88, 127.05, 124.24, 120.33, 119.12, 118.43, 114.67, 110.46, 16.02.

7-Chloro-4-bromo-quinoline (120)

7-chloro-4-hydroxylquinoline (180 mg, 1.00 mmol) was dissolved in DMF, to which was added slowly phosphorous tribromide (3.54 mL, 3.73 mmol). It was stirred at 60° C. overnight, and then cooled to room temperature and poured into ice water, neutralized with Na$_2$CO$_3$. The precipitation was filtered out and washed with water, dried by pulling air through. Product was obtained as white solid (136 mg, 56% yield). $^1$H NMR (400 MHz, Chloroform-d) δ 8.68 (d, J=4.6 Hz, 1H), 8.19-8.10 (m, 2H), 7.71 (d, J=4.7 Hz, 1H), 7.61 (dd, J=9.0, 2.1 Hz, 1H).

4-(7-Chloro-4-quinolinyl)-2-methyl-phenol (63)

General procedure B was applied using 120 (100 mg, 0.41 mmol), 2-methyl-4-(4,4,5,5-tetramethyl-1,3,2-dioxaborolan-2-yl)-phenol (100 mg, 0.43 mmol), K$_2$CO$_3$ (177 mg, 1.28 mmol) and [1,1'-bis(diphenylphosphino)ferrocene]palladium(II) dichloride (18 mg, 0.02 mmol), to give light yellow solid (46 mg, 42%) ESI-MS m/z: 270.0681 [M+H]$^+$; Purity: 93.9%. $^1$H NMR (400 MHz, Chloroform-d) δ 8.91 (d, J=4.5 Hz, 1H), 8.16 (d, J=2.2 Hz, 1H), 7.93 (dd, J=9.0, 0.5 Hz, 1H), 7.46 (dd, J=9.0, 2.2 Hz, 1H), 7.31 (d, J=4.5 Hz, 1H), 7.27 (dd, J=2.1, 0.9 Hz, 1H), 7.21 (ddd, J=8.1, 2.2, 0.6 Hz, 1H), 6.94 (d, J=8.1 Hz, 1H), 2.36 (s, 3H). $^{13}$C NMR (101 MHz, CDCl$_3$) δ 154.76, 151.07, 149.27, 148.78, 135.37, 132.34, 129.95, 128.73, 128.53, 127.69, 127.61, 125.63, 124.58, 121.56, 115.30, 16.04.

4-(4-Methoxyl-3-methylphenyl)-7-phenyl-quinoline (64)

General procedure B was applied using 63 (27 mg, 0.10 mmol), phenylboronic acid (12 mg, 0.10 mmol), K$_3$PO$_4$ (64 mg, 0.30 mmol) and and [1,1'-bis(diphenylphosphino)ferrocene]palladium(II) dichloride (10 mg, 0.01 mmol) to give light yellow solid (13 mg, 42%) ESI-MS m/z: 312.1388 [M+H]$^+$; Purity: 98.7%. $^1$H NMR (400 MHz, Chloroform-d) δ 8.95 (d, J=4.5 Hz, 1H), 8.41 (d, J=1.9 Hz, 1H), 8.09 (d, J=8.8 Hz, 1H), 7.82-7.75 (m, 3H), 7.54-7.47 (m, 2H), 7.45-7.39 (m, 1H), 7.36-7.32 (m, 2H), 7.28 (d, J=2.3 Hz, 1H), 6.99 (d, J=8.1 Hz, 1H), 2.39 (s, 3H). $^{13}$C NMR (101 MHz, CDCl$_3$) δ 155.00, 150.38, 148.96, 148.82, 142.16, 140.27, 132.39, 130.09, 129.16, 128.54, 128.09, 127.63, 127.19, 126.79, 126.31, 126.28, 124.68, 121.31, 115.28, 16.17.

2-Methoxy-3-methyl-5-(4,4,5,5-tetramethyl-1,3,2-dioxaborolan-2-yl)pyridine (121)

General procedure A was applied using potassium acetate (786 mg, 8.00 mmol), bis-(pinacolato)-diboron (610 mg, 2.40 mmol) and bis(diphenylphosphine) ferrocene dichloropalladium (II) complex with dichloromethane (82 mg, 0.10 mmol) was added to an anhydrous solution of 4-bromo-1-methoxy-2-methylbenzene (436 mg g, 1.68 mmol). The residue was purified by silica gel column (eluent: dichloromethane/ethyl acetate, 0-20%) to yield light yellow solid (477 mg, 93%). $^1$H NMR (400 MHz, Chloroform-d) δ 7.65 (s, 1H), 7.47 (s, 1H), 3.55 (s, 3H), 2.12 (s, 3H), 1.30 (s, 12H).

4-(4-Methoxy-5-methylpyridin-3-yl)-quinoline (65)

General procedure B was applied using 4-chloro-quinolone (25 mg, 0.10 mmol), 120 (12 mg, 0.10 mmol), K$_3$PO$_4$ (64 mg, 0.30 mmol) and tetrakis(triphenylphosphine) palladium(0) (4 mg, 0.02 mmol), CyJohnphos (4 mg, 0.01 mmol) to give light yellow solid (46 mg, 42%). ESI-MS m/z: 251.1180 [M+H]$^+$; Purity: 93.1%. $^1$H NMR (400 MHz, Chloroform-d) δ 8.92 (d, J=4.4 Hz, 1H), 8.18 (ddd, J=8.5, 1.4, 0.7 Hz, 1H), 7.94 (ddd, J=8.4, 1.4, 0.6 Hz, 1H), 7.76 (ddd, J=8.4, 6.9, 1.5 Hz, 1H), 7.58 (ddd, J=8.3, 6.8, 1.3 Hz, 1H), 7.43 (dt, J=2.3, 1.1 Hz, 1H), 7.38 (dd, J=2.6, 0.8 Hz, 1H), 7.28 (d, J=4.4 Hz, 1H), 3.67 (s, 3H), 2.26 (s, 3H). $^{13}$C NMR (101 MHz, CDCl$_3$) δ 162.92, 150.22, 148.95, 143.93, 138.23, 135.71, 130.35, 129.96, 129.78, 127.14, 126.79, 125.20, 121.06, 116.38, 38.29, 17.55.

2-Benzyloxy-5-bromo-3-methylpyridine (122)

To a solution of 5-bromo-2-hydroxy-3-methyl pyridine (376 mg, 2.00 mmol) in toluene (15 mL) were added $Ag_2CO_3$ (827 mg, 3.00 mmol) and benzyl bromide (513 mg, 3.00 mmol), and the mixture was stirred at 40° C. for 2 h. The insoluble material was filtered, and the filtrate was concentrated in vacuo. The residue was purified by silica gel column (eluent: dichloromethane/methanol, 0-20%) to yield light yellow solid (436 mg, 78%). $^1H$ NMR (400 MHz, Chloroform-d) δ 8.08-8.02 (m, 1H), 7.51 (m, 1H), 7.49-7.41 (m, 2H), 7.43-7.28 (m, 3H), 5.38 (s, 2H), 2.22 (s, 3H).

3-Methyl-2-phenylmethoxy-5-(4,4,5,5-tetramethyl-1,3,2-dioxaborolan-2-yl)pyridine General procedure A was applied using potassium acetate (147 mg, 1.50 mmol), bis-(pinacolato)-diboron (191 mg, 0.75 mmol) and bis(diphenylphosphine) ferrocene dichloropalladium (II) complex with dichloromethane (42 mg, 0.05 mmol) was added to an anhydrous solution of 121 (140 mg g, 0.50 mmol). Product was obtained as light yellow solid (137 mg, 84%). ESI-MS m/z: 326.1929 $[M+H]^+$; $^1H$ NMR (400 MHz, Chloroform-d) δ 8.41 (m, 1H), 7.78 (m, 1H), 7.47 (m, 2H), 7.42-7.28 (m, 3H), 5.46 (s, 2H), 2.23 (s, 3H), 1.34 (s, 12H). $^{13}C$ NMR (101 MHz, $CDCl_3$) δ 164.11, 151.51, 144.46, 137.85, 128.48, 127.70, 127.68, 120.18, 83.87, 67.49, 24.97, 15.81.

4-(4-Hydroxyl-5-methylpyridin-3-yl)-7-hydroxyl-quinoline (66)

A solution of 68 (26 mg, 0.10 mmol) in anhydrous dichloromethane (3 mL) was cooled in ice bath and treated dropwise with a 1 M solution of $BBr_3$ in dichloromethane (500 uL, 0.50 mmol), and the resulting solution was stirred in an ice bath for 30 min and at room temperature for 1 h. The mixture was then diluted with water and adjusted to pH 6 with $NaHCO_3$ and extracted with ethyl acetate. The combined organic layers were dried over magnesium sulfate, filtered and concentrated. The residue was purified by flash column chromatography on silica gel (eluent: dichloromethane/methanol, 0-20%) to give the title compound as a light yellow solid (16 mg, 63%). ESI-MS m/z: 275.0787 $[M+Na]^+$; Purity: 98.2%. $^1H$ NMR (400 MHz, DMSO-$d_6$) δ 11.87 (s, 1H), 10.30 (s, 1H), 8.71 (d, J=4.5 Hz, 1H), 7.79 (d, J=9.1 Hz, 1H), 7.54 (dd, J=2.6, 1.3 Hz, 1H), 7.44 (d, J=2.6 Hz, 1H), 7.29 (d, J=2.6 Hz, 1H), 7.23-7.08 (m, 2H), 2.06 (s, 3H). $^{13}C$ NMR (101 MHz, DMSO) δ 162.20, 158.43, 150.23, 150.17, 143.28, 138.96, 132.57, 128.59, 126.52, 120.10, 119.46, 118.27, 114.98, 110.63, 16.53.

4-(4-Methoxy-5-methylpyridin-3-yl)-7-methoxyl-quinoline (67)

General procedure B was applied using 4-chloro-7-methoxy-quinolone (177 mg, 0.91 mmol), 2-methyl-4-(4,4,5,5-tetramethyl-1,3,2-dioxaborolan-2-yl)-phenol (228 mg, 0.92 mmol), $K_2CO_3$ (379 mg, 2.74 mmol) and [1,1'-bis(diphenylphosphino)ferrocene]palladium(II) dichloride (37 mg, 0.05 mmol), to give light yellow solid (142 mg, 56%). ESI-MS m/z: 281.1288 $[M+H]^+$; Purity: 96.7%. $^1H$ NMR (400 MHz, DMSO-$d_6$) δ 8.81 (d, J=4.5 Hz, 1H), 7.94-7.87 (m, 2H), 7.55 (dd, J=2.6, 1.2 Hz, 1H), 7.46 (d, J=2.6 Hz, 1H), 7.32-7.24 (m, 2H), 3.94 (s, 3H), 3.54 (s, 3H), 2.10 (s, 3H). $^{13}C$ NMR (101 MHz, DMSO) δ 161.77, 160.04, 150.39, 150.14, 143.26, 137.93, 137.40, 127.67, 126.56, 120.92, 119.44, 119.08, 114.44, 107.90, 55.53, 37.28, 16.98.

4-(4-Hydroxyl-5-methylpyridin-3-yl)-7-methoxyl-quinoline (68)

Compound 70 (33 mg 0.09 mmol) was dissolved in ethanol, palladium on carbon (10 mg, 0.01 mmol) was added and stirred in $H_2$ atmosphere at room temperature overnight. The insoluble material was filtered, and the filtrate was concentrated in vacuo. The residue was purified by silica gel column (eluent: dichloromethane/methanol, 0-20%) to give the title compound as a light yellow solid (18 mg, 75%). ESI-MS m/z: 267.1139 $[M+H]^+$; Purity: 98.0%. $^1H$ NMR (400 MHz, DMSO-$d_6$) δ 11.91 (s, 1H), 8.80 (d, J=4.5 Hz, 1H), 7.85 (d, J=9.2 Hz, 1H), 7.55 (dd, J=2.6, 1.2 Hz, 1H), 7.47 (dd, J=2.6, 0.8 Hz, 1H), 7.45 (d, J=2.6 Hz, 1H), 7.29-7.25 (m, 2H), 3.93 (s, 3H), 2.06 (s, 3H). $^{13}C$ NMR (101 MHz, DMSO) 162.20, 160.00, 150.41, 150.12, 143.37, 138.91, 132.72, 128.66, 126.43, 120.96, 119.40, 119.06, 114.78, 107.92, 55.52, 16.53.

7-Hydroxyl-4-(4-methoxy-5-methylpyridin-3-yl)-quinoline (69)

A solution of 67 (18 mg, 0.06 mmol) in anhydrous dichloromethane (3 mL) was cooled in ice bath and treated dropwise with a 1 M solution of $BBr_3$ in dichloromethane (36 uL, 0.36 mmol), and the resulting solution was stirred in an ice bath for 30 min and at room temperature for 1 h. The mixture was then diluted with water and adjusted to pH 6 with $NaHCO_3$ and extracted with ethyl acetate. The combined organic layers were dried over magnesium sulfate, filtered and concentrated. The residue was purified by flash column chromatography on silica gel (eluent: dichloromethane/methanol, 0-20%) to give the title compound as a light yellow solid (12 mg, 70%). ESI-MS m/z: 267.1134 $[M+H]^+$; Purity: 91.6%. $^1H$ NMR (400 MHz, DMSO-$d_6$) δ 10.26 (s, 1H), 8.73 (d, J=4.6 Hz, 1H), 7.93-7.79 (m, 2H), 7.54 (dd, J=2.7, 1.4 Hz, 1H), 7.30 (d, J=2.5 Hz, 1H), 7.25-7.13 (m, 2H), 3.53 (s, 3H), 2.09 (s, 3H). $^{13}C$ NMR (101 MHz, DMSO) δ 161.82, 158.43, 150.26, 150.19, 143.21, 138.03, 137.31, 127.65, 126.72, 120.12, 119.50, 118.36, 114.69, 110.62, 37.33, 17.03.

4-(4-Benzyl-5-methylpyridin-3-yl)-7-methoxyl-quinoline (70)

General procedure B was applied using 4-chloro-7-methoxy-quinolone (82 mg, 0.42 mmol), 121 (137 mg, 0.42 mmol), $K_2CO_3$ (175 mg, 1.26 mmol) and [1,1'-bis(diphenylphosphino) ferrocene]palladium(II) dichloride (34 mg, 0.04 mmol), to give light yellow solid (41 mg, 27%). ESI-MS m/z: 357.1597 $[M+H]^+$; Purity: 98.1%. $^1H$ NMR (400 MHz, Chloroform-d) δ 8.85 (d, J=4.6 Hz, 1H), 8.15 (dt, J=2.4, 0.7 Hz, 1H), 7.81 (dd, J=9.2, 1.1 Hz, 1H), 7.57 (dt, J=2.4, 0.8 Hz, 1H), 7.55-7.48 (m, 3H), 7.44-7.40 (m, 2H), 7.36-7.32 (m, 1H), 7.20-7.16 (m, 2H), 5.50 (s, 2H), 3.97 (s, 3H), 2.34 (s, 3H). $^{13}C$ NMR (101 MHz, $CDCl_3$) δ 162.16, 160.70, 150.36, 145.14, 144.23, 139.73, 137.66, 128.59, 127.88, 127.75, 127.33, 126.74, 121.05, 120.00, 119.95, 119.62, 107.90, 67.82, 55.69, 16.15.

4-(4-Hydroxy-butoxy-3-methylphenyl)-7-phenyl-quinoline (71)

A solution of 61 (100 mg, 0.38 mmol), 4-Bromo-1-butanol (70 mg, 0.46 mmol), NaH (19 mg, 0.79 mmol) in dioxane and was heated at 100 overnight. The mixture was then diluted with water and extracted with ethyl acetate. The organic phase was dried and concentrated. The crude product was purified by flash chromatography (dichloromethane/ethyl acetate 0-10%) to yield pure product as a yellow solid (54 mg, 42% yield). ESI-MS m/z: 338.1764 [M+H]$^+$; Purity: 92.5%. $^1$H NMR (400 MHz, Chloroform-d) δ 8.83 (s, 1H), 7.88 (dd, J=9.3, 1.8 Hz, 1H), 7.48 (s, 1H), 7.32-7.27 (m, 2H), 7.21-7.12 (m, 2H), 6.94 (d, J=8.9 Hz, 1H), 4.10 (t, J=6.0 Hz, 2H), 3.97 (s, 3H), 3.78 (t, J=6.4 Hz, 2H), 2.31 (s, 3H), 2.02-1.91 (m, 2H), 1.83 (dq, J=9.6, 6.4 Hz, 2H). $^{13}$C NMR (101 MHz, CDCl$_3$) δ 160.37, 157.33, 150.52, 150.13, 148.37, 131.79, 131.74, 129.99, 128.05, 127.24, 127.03, 119.44, 110.70, 110.64, 107.55, 67.86, 62.63, 55.54, 29.62, 25.89, 16.42.

4-(4-Formyl-3-methylphenyl)quinoline (72)

General procedure B was applied using 4-bromo-quinolone (104 mg, 0.50 mmol), 2-methyl-4-(4,4,5,5-tetramethyl-1,3,2-dioxaborolan-2-yl)benzaldehyde (123 mg, 0.50 mmol), K$_2$CO$_3$ (208 mg, 1.50 mmol) and [1,1'-bis(diphenylphosphino)ferrocene]palladium(II) dichloride (19 mg, 0.03 mmol), to give light yellow solid (94 mg, 71% yield). ESI-MS m/z: 248.1077 [M+H]$^+$; Purity: 97.2%. $^1$H NMR (400 MHz, Chloroform-d) δ 10.38 (s, 1H), 9.03-8.96 (m, 1H), 8.20 (dt, J=8.5, 0.9 Hz, 1H), 7.97 (d, J=7.7 Hz, 1H), 7.85 (dd, J=8.5, 1.3 Hz, 1H), 7.76 (ddd, J=8.4, 6.8, 1.4 Hz, 1H), 7.53 (m, 2H), 7.44-7.39 (m, 1H), 7.35 (d, J=4.3 Hz, 1H), 2.78 (s, 3H). $^{13}$C NMR (101 MHz, CDCl$_3$) δ 192.39, 150.03, 148.73, 147.27, 143.42, 141.10, 134.03, 133.04, 132.32, 130.13, 129.76, 127.72, 127.18, 126.36, 125.58, 121.23, 19.88.

4-(4-Acetyl-3-methylphenyl)quinoline (73)

General procedure B was applied using 4-bromo-quinolone (104 mg, 0.50 mmol), 1-[2-methyl-4-(4,4,5,5-tetramethyl-1,3,2-dioxaborolan-2-yl)phenyl]ethanone (130 mg, 0.50 mmol), K$_2$CO$_3$ (208 mg, 1.50 mmol) and [1,1'-bis(diphenylphosphino)ferrocene]palladium(II) dichloride (19 mg, 0.03 mmol), to give light yellow solid (87 mg, 67% yield). ESI-MS m/z: 262.1226 [M+H]$^+$; Purity: 97.0%. $^1$H NMR (400 MHz, Chloroform-d) δ 8.96 (d, J=4.4 Hz, 1H), 8.19 (dt, J=8.6, 0.9 Hz, 1H), 7.91-7.83 (m, 2H), 7.75 (ddd, J=8.4, 6.9, 1.5 Hz, 1H), 7.53 (ddd, J=8.3, 6.8, 1.3 Hz, 1H), 7.45-7.39 (m, 2H), 7.33 (d, J=4.4 Hz, 1H), 2.67 (s, 3H), 2.63 (s, 3H). $^{13}$C NMR (101 MHz, CDCl$_3$) δ 201.44, 150.04, 148.72, 147.50, 141.27, 139.08, 137.53, 133.25, 130.07, 129.75, 129.67, 127.04, 126.53, 125.70, 121.26, 29.81, 21.89.

4-(4-Amino-3-methylphenyl)quinoline (74)

General procedure B was applied using 4-bromo-quinolone (104 mg, 0.50 mmol), 2-methyl-4-(4,4,5,5-tetramethyl-1,3,2-dioxaborolan-2-yl)-aniline (116 mg, 0.50 mmol), K$_2$CO$_3$ (208 mg, 1.50 mmol) and [1,1'-bis(diphenylphosphino)ferrocene]palladium(II) dichloride (19 mg, 0.03 mmol), to give light yellow solid (88 mg, 75% yield). ESI-MS m/z: 235.1237 [M+H]$^+$; Purity: 95.8%. $^1$H NMR (400 MHz, Chloroform-d) δ 8.90 (d, J=4.5 Hz, 1H), 8.14 (ddd, J=8.5, 1.4, 0.7 Hz, 1H), 8.05 (ddd, J=8.5, 1.5, 0.6 Hz, 1H), 7.71 (ddd, J=8.4, 6.8, 1.5 Hz, 1H), 7.49 (ddd, J=8.3, 6.8, 1.3 Hz, 1H), 7.31 (d, J=4.4 Hz, 1H), 7.25-7.19 (m, 2H), 6.82 (dd, J=7.9, 0.5 Hz, 1H), 2.27 (s, 3H). $^{13}$C NMR (101 MHz, CDCl$_3$) δ 150.02, 148.83, 148.79, 145.05, 131.77, 129.75, 129.10, 128.47, 128.01, 127.07, 126.25, 126.20, 122.28, 121.13, 114.74, 17.50.

4-(4-Methoxyl-3-methylphenyl)quinoline (75)

A solution of 37 (24 mg, 0.10 mmol), MeI (28 mg, 0.2 mmol), NaH (24 mg, 0.60 mmol), dioxane (3 mL) and H$_2$O (1 mL) was heated at 100° C. overnight. The mixture was then diluted with water and extracted with ethyl acetate. The organic phase was dried and concentrated. The crude product was purified by flash chromatography (dichloromethane/ethyl acetate 0-10%) to yield title compound (18 mg, 68% yield) as a yellow solid. ESI-MS m/z: 250.1235 [M+H]$^+$; Purity: 92.4%. $^1$H NMR (400 MHz, DMSO-d$_6$) δ 8.91 (d, J=4.4 Hz, 1H), 8.13-8.06 (m, 1H), 7.96-7.91 (m, 1H), 7.78 (ddd, J=8.4, 6.8, 1.4 Hz, 1H), 7.59 (ddd, J=8.3, 6.8, 1.3 Hz, 1H), 7.41 (d, J=4.4 Hz, 1H), 7.39-7.35 (m, 2H), 7.14 (d, J=8.1 Hz, 1H), 3.88 (s, 3H), 2.25 (s, 3H). $^{13}$C NMR (101 MHz, DMSO) δ 157.68, 150.10, 148.25, 147.34, 131.44, 129.51, 129.30, 129.05, 128.30, 126.75, 126.13, 126.03, 125.59, 121.33, 110.47, 55.45, 16.10.

3-(4-Hydroxyl-3-methylphenyl)quinoline (76)

General procedure B was applied using 3-bromo-quinoline (72 mg, 0.35 mmol), 2-methyl-4-(4,4,5,5-tetramethyl-1,3,2-dioxaborolan-2-yl)-phenol (54 mg, 0.23 mmol), Na$_2$CO$_3$ (73 mg, 0.69 mmol) and [1,1'-bis(diphenylphosphino)ferrocene]palladium(II) dichloride (9 mg, 0.01 mmol), to give light yellow solid (47 mg, 86% yield). ESI-MS m/z: 236.1082 [M+H]$^+$; Purity: 98.9%. $^1$H NMR (400 MHz, Chloroform-d) δ 9.15 (d, J=2.3 Hz, 1H), 8.27-8.22 (m, 1H), 8.13 (d, J=8.5 Hz, 1H), 7.88-7.84 (m, 1H), 7.70 (ddd, J=8.4, 6.9, 1.5 Hz, 1H), 7.57 (ddd, J=8.0, 6.8, 1.2 Hz, 1H), 7.53-7.49 (m, 1H), 7.45 (dd, J=8.2, 2.4 Hz, 1H), 6.94 (d, J=8.2 Hz, 1H), 2.38 (s, 3H). $^{13}$C NMR (101 MHz, CDCl$_3$) δ 154.76, 149.90, 146.87, 138.87, 133.95, 132.68, 130.23, 129.28, 129.08, 128.39, 128.03, 127.16, 126.27, 125.13, 115.82, 16.20.

2-Methyl-1-quinolin-4-ylpropan-2-ol (77)

Under an argon atmosphere, a solution of lepidine (67 uL, 0.50 mmol) in THF was cooled to −78° C., and then a solution of butyl lithium in hexane (375 uL, 0.6 mmol) was dropwise added thereto, followed by stirring at the same temperature for one hour. A solution (10 ml) of acetone (29 mg, 0.50 mmol) in THF was slowly and dropwise added to the mixture, followed by stirring at 78° C. for 2 hours and then at 0° C. for one hour. The reaction solution was poured into water and the mixture was extracted with ether. The organic layer was washed with a saturated saline and dried over anhydrous magnesium sulfate, and the solvent was removed under reduced pressure. The residue was purified by silica gel column chromatography (chloroform ethyl acetate 0-10%) to give Compound (52 mg, 51%). ESI-MS m/z: 202.1237 [M+H]$^+$; Purity: 95.8%. $^1$H NMR (400 MHz, Chloroform-d) δ 8.85 (d, J=4.4 Hz, 1H), 8.16 (dd, J=17.9, 8.5 Hz, 2H), 7.77-7.67 (m, 1H), 7.63-7.53 (m, 1H), 7.33 (d, J=4.4 Hz, 1H), 3.30 (s, 2H), 1.32 (s, 6H). $^{13}$C NMR (101 MHz, CDCl$_3$) δ 149.81, 148.79, 144.34, 130.32, 129.25, 128.82, 126.44, 125.01, 123.87, 71.66, 44.66, 30.11.

(4-Hydroxyphenyl) quinolin-1-yl-methanone (78)

4-Quinolinic acid (173 mg, 1.00 mmol) in thionyl chloride (2 mL) was stirred at 100° C. for 1.5 h. Excess SOCl$_2$ was removed under reduced pressure, and anisole (108 mg, 1.00 mmol) was added to the yellow residue. Upon cooling in an ice-bath, AlCl$_3$ (400 mg, 3.00 mol) was added and the mixture was allowed to slowly return to room temperature. The solution was then heated to 90° C. and stirred for 4 h. The reaction was quenched by slowly pouring the reaction mixture into 400 mL of a 4.2% w/v HCl/ice-water solution. A pH 4 was reached with the addition of Na$_2$CO$_3$ and then a saturated aqueous NaOH solution was added to attain pH 10. The organic layer was extracted with CHCl$_3$ and dried with MgSO$_4$. The solvents were removed with a rotary evaporator, residue was purified by flash column chromatography on silica gel (eluent: dichloromethane/methanol, 0-20%) to give the title compound as a light yellow solid (46 mg, 17%). ESI-MS m/z: 264.1035 [M+H]$^+$; Purity: 97.8%. $^1$H NMR (400 MHz, Chloroform-d) δ 9.02 (d, J=4.3 Hz, 1H), 8.19 (ddd, J=8.6, 1.3, 0.7 Hz, 1H), 7.87-7.80 (m, 3H), 7.76 (ddd, J=8.4, 6.9, 1.4 Hz, 1H), 7.52 (ddd, J=8.3, 6.9, 1.3 Hz, 1H), 7.39 (d, J=4.3 Hz, 1H), 6.97-6.91 (m, 2H), 3.88 (s, 3H). $^{13}$C NMR (101 MHz, CDCl$_3$) δ 194.67, 164.65, 149.67, 148.67, 145.26, 132.90, 130.13, 130.06, 129.73, 127.65, 125.63, 125.20, 119.38, 114.20, 55.76.

4-[hydroxy(7-methoxylquinolin-4-yl)methyl]-2-methylanisole (79)

4-Bromo-7-methoxyquinoline (204 mg, 0.86 mmol) was dissolved in anhydrous THF in –78° C., n-butyl lithium was added slowly. The reaction mixture was stirred at –78° C. for 2 h, and then 3-methyl-4-anisaldehyde (257 mg, 1.72 mmol) was added slowly. the mixture was slowly warmed to room temperature and stirred overnight. The mixture was then diluted with water and extracted with ethyl acetate. The organic phase was dried and concentrated. The crude product was purified by flash chromatography (dichloromethane/ethyl acetate 0-10%) to yield product as a yellow solid (243 mg, 91% yield). ESI-MS m/z: 310.1444 [M+H]$^+$; Purity: 99.6%. $^1$H NMR (400 MHz, Chloroform-d) δ 8.89 (d, J=4.5 Hz, 1H), 7.77 (d, J=9.3 Hz, 1H), 7.63 (dd, J=4.5, 0.9 Hz, 1H), 7.43 (d, J=2.7 Hz, 1H), 7.15-7.02 (m, 3H), 6.75 (d, J=9.0 Hz, 1H), 6.39 (s, 1H), 3.92 (s, 3H), 3.79 (s, 3H), 2.16 (s, 3H). $^{13}$C NMR (101 MHz, CDCl$_3$) δ 160.05, 157.80, 150.33, 148.58, 133.87, 129.80, 126.07, 125.09, 120.63, 119.78, 116.29, 110.08, 72.69, 55.64, 55.48, 16.48.

4-(4-Methoxyl-3-methylbenzyl)-7-methoxyl-quinoline (80)

To a solution of 79 (91 mg, 0.29 mmol) in anhydrous dichloromethane was added in sequence by syringe trifluoroacetic acid (331 mg, 2.90 mmol), triethylsilane (101 mg, 0.87 mmol), and trifluoromethanesulfonic acid (5 mg, 0.03 mmol) under an atmosphere of nitrogen at 0° C. The resulting solution was stirred at room temperature overnight. Afterward, the reaction mixture was separated, and the aqueous layer was extracted with dichloromethane (2×30 mL). The combined organic layers were washed with aqueous NaHCO$_3$ and brine, dried over MgSO$_4$, and concentrated in vacuo to light yellow oil (81 mg, 95% yield). ESI-MS m/z: 294.1500; Purity: 95.4%. $^1$H NMR (400 MHz, Chloroform-d) δ 8.73 (d, J=4.5 Hz, 1H), 7.93 (d, J=9.2 Hz, 1H), 7.45 (d, J=2.6 Hz, 1H), 7.18 (dd, J=9.2, 2.5 Hz, 1H), 7.02 (d, J=4.3 Hz, 1H), 6.97-6.93 (m, 2H), 6.76-6.72 (m, 1H), 4.30 (s, 2H), 3.95 (s, 3H), 3.80 (s, 3H), 2.17 (s, 3H). $^{13}$C NMR (101 MHz, CDCl$_3$) δ 160.40, 156.56, 150.61, 150.16, 147.34, 131.30, 131.26, 130.35, 127.09, 127.00, 125.22, 120.07, 119.61, 110.12, 107.96, 55.62, 55.46, 37.47, 16.39.

4-(4-Hydroxyl-3-methylbenzyl)-7-hydroxyl-quinoline (81)

A solution of 80 (86 mg, 0.30 mmol) in anhydrous dichloromethane (10 mL) was cooled to –78° C. and treated dropwise with a 1 M solution of BBr$_3$ in dichloromethane (0.90 mL), and the resulting solution was stirred at the same temperature for 5 min and at 0° C. for 1 h. The mixture was then diluted with water and extracted with ethyl acetate. The organic phase was dried and concentrated. The crude product was purified by flash chromatography (dichloromethane/ethyl acetate 0-10%) to yield product as a yellow solid (47 mg, 59% yield). ESI-MS m/z: 266.1188 [M+H]$^+$; Purity: 97.6%. $^1$H NMR (400 MHz, DMSO-d$_6$) δ 10.12 (s, 1H), 9.12 (s, 1H), 8.63 (d, J=4.5 Hz, 1H), 8.02 (d, J=9.1 Hz, 1H), 7.23 (d, J=2.5 Hz, 1H), 7.13 (dd, J=9.1, 2.5 Hz, 1H), 7.06 (d, J=4.5 Hz, 1H), 6.94 (d, J=2.2 Hz, 1H), 6.85 (dd, J=8.1, 2.3 Hz, 1H), 6.67 (d, J=8.2 Hz, 1H), 4.22 (s, 2H), 2.04 (s, 3H). $^{13}$C NMR (101 MHz, DMSO) δ 158.13, 153.80, 150.30, 149.66, 147.37, 130.91, 129.22, 126.90, 125.81, 123.80, 121.17, 119.06, 118.91, 114.57, 110.48, 36.45, 16.06.

4-(Quinolin-4-ylamino)-2-methylanisole (82)

A mixture of 4-bromoquinoline (104 mg, 0.50 mmol), 4-methoxy-3-methylaniline (103 mg, 0.75 mmol), sodium hydride (60 mg, 1.50 mmol) was heated in DMF at 100 overnight. The mixture was diluted with EtOAc and washed with saturated aqueous NaHCO$_3$, dried (Na$_2$SO$_4$), filtered, and concentrated. The combined organic layers were dried over magnesium sulfate, filtered, concentrated in vacuum. The residue was purified by flash column chromatography on silica gel (eluent: dichloromethane/ethyl acetate, 0-10%) to give light yellow solid. (107 mg, 81%). ESI-MS m/z: 265.1347 [M+H]$^+$; Purity: 97.6%. $^1$H NMR (400 MHz, DMSO-d$_6$) δ 8.81 (s, 1H), 8.47-8.29 (m, 2H), 7.84 (d, J=8.4 Hz, 1H), 7.67 (ddd, J=8.4, 6.8, 1.3 Hz, 1H), 7.50 (ddd, J=8.2, 6.8, 1.2 Hz, 1H), 7.24-7.13 (m, 2H), 7.05-6.95 (m, 1H), 6.62 (d, J=5.3 Hz, 1H), 3.81 (s, 3H), 2.18 (s, 3H). $^{13}$C NMR (101 MHz, DMSO) δ 154.59, 150.42, 149.17, 148.54, 132.27, 129.15, 128.90, 126.79, 126.59, 124.34, 122.88, 121.95, 119.15, 110.98, 100.26, 55.44, 16.10.

3-Pentyl-quinoline-2-amine (83)

General procedure B was applied using 3-bromonaphthalen-2-amine (44 mg, 0.20 mmol), n-pentylboronic acid (23 mg, 0.20 mmol), K$_2$CO$_3$ (83 mg, 0.60 mmol) and [1,1'-bis(diphenylphosphino)ferrocene] palladium(II) dichloride (10 mg, 0.01 mmol), to give light yellow solid (13 mg, 30%). Purity: 97.6%. $^1$H NMR (400 MHz, Chloroform-d) δ 7.69 (s, 1H), 7.66 (d, J=8.4 Hz, 1H), 7.60 (dd, J=8.0, 1.4 Hz, 1H), 7.51 (ddd, J=8.4, 6.8, 1.5 Hz, 1H), 7.28-7.22 (m, 1H), 2.58 (t, J=7.8 Hz, 2H), 1.79-1.65 (m, 2H), 1.40 (q, J=3.7 Hz, 4H), 0.98-0.89 (t, 9.0 Hz, 3H).

5-Pentyl-7-methoxylquinoline (84)

General procedure B was applied using 4-bromo-7-methoxylquinoline (48 mg, 0.20 mmol), n-pentyl boronic acid (23 mg, 0.20 mmol), KH$_2$PO$_4$ (83 mg, 0.60 mmol), Pd(OAc)$_2$ (5 mg, 0.02 mmol) and SPhos (10 mg, 0.02 mmol) to give light yellow solid (35 mg, 85%). ESI-MS m/z: 230.1558 [M+H]$^+$; Purity: 88.3%. $^1$H NMR (400 MHz, Chloroform-d) δ 8.71 (d, J=4.5 Hz, 1H), 7.92 (d, J=9.2 Hz, 1H), 7.44 (d, J=2.5 Hz, 1H), 7.20 (dd, J=9.2, 2.6 Hz, 1H), 7.11 (d, J=4.5 Hz, 1H), 3.95 (s, 3H), 3.07-2.91 (m, 2H), 1.82-1.66 (m, 2H), 1.46-1.30 (m, 4H), 0.90 (t, J=6.7 Hz, 3H). $^{13}$C NMR (101 MHz, CDCl$_3$) δ 160.43, 150.25, 149.91, 149.29, 124.94, 122.82, 119.45, 119.11, 107.81, 55.65, 32.35, 31.96, 30.07, 22.64, 14.14.

3-Pentyl-quinoline (85)

General procedure B was applied using 3-bromo-quinoline (42 mg, 0.20 mmol), n-pentylboronic acid (23 mg, 0.20 mmol), KH$_2$PO$_4$ (83 mg, 0.60 mmol) and Pd(OAc)$_2$ (5 mg, 0.02 mmol), SPhos (10 mg, 0.02 mmol), to give light yellow solid (23 mg, 58%). ESI-MS m/z: 200.1441 [M+H]$^+$; Purity: 99.3%. $^1$H NMR (400 MHz, Chloroform-d) δ 8.77 (d, J=2.2 Hz, 1H), 8.08 (d, J=8.5 Hz, 1H), 7.90 (s, 1H), 7.75 (dd, J=8.2, 1.3 Hz, 1H), 7.64 (ddd, J=8.4, 6.8, 1.5 Hz, 1H), 7.51 (t, J=7.5 Hz, 1H), 2.78 (t, 2H), 1.71 (p, J=7.4 Hz, 2H), 1.35 (m, 4H), 0.93-0.87 (m, 3H). $^{13}$C NMR (101 MHz, CDCl$_3$) δ 152.21, 146.79, 135.50, 134.25, 129.17, 128.60, 128.29, 127.40, 126.61, 33.28, 31.46, 30.93, 22.60, 14.12.

4-Bromo-quinolin-2-ylamine (124)

2-Amino-4-quinolinol (60 mg, 0.37 mmol) was stirred in PBr$_3$ (5 mL) at 90° C. overnight. The reaction was then quenched with saturated sodium carbonate solution and extracted with ethyl acetate (50 mL×3). The combined organic layers were dried over magnesium sulfate, filtered and concentrated. The residue was purified by flash column chromatography on silica gel (eluent: dichloromethane/ethyl acetate, 10-100%) to give the title compound as a white solid (46 mg, 56%). $^1$H NMR (400 MHz, Chloroform-d) 7.99 (ddd, J=8.3, 1.5, 0.7 Hz, 1H), 7.64 (ddd, J=8.4, 1.5, 0.6 Hz, 1H), 7.60 (ddd, J=8.3, 6.6, 1.4 Hz, 1H), 7.35 (ddd, J=8.2, 6.6, 1.5 Hz, 1H), 7.08 (s, 1H).

2-Amino-4-(4-hydroxyl-3-methylphenyl)-quinoline (86)

General procedure B was applied using 124 (60 mg, 0.34 mmol), 2-methyl-4-(4,4,5,5-tetramethyl-1,3,2-dioxaborolan-2-yl)-phenol (79 mg, 0.34 mmol), K$_2$CO$_3$ (140 mg, 1.01 mmol) and [1,1'-bis(diphenylphosphino)ferrocene]palladium(II) dichloride (14 mg, 0.01 mmol), to give light yellow solid (43 mg, 51%). ESI-MS m/z: 251.1191 [M+H]$^+$; Purity: 98.2%. $^1$H NMR (400 MHz, DMSO-d$_6$) δ 9.65 (s, 1H), 7.59 (dd, J=8.2, 1.3 Hz, 1H), 7.53-7.43 (m, 2H), 7.18 (dd, J=2.4, 0.9 Hz, 1H), 7.11 (ddd, J=8.2, 4.6, 2.0 Hz, 2H), 6.92 (d, J=8.2 Hz, 1H), 6.62 (s, 1H), 6.46 (s, 2H), 2.19 (s, 3H). $^{13}$C NMR (101 MHz, DMSO) δ 157.82, 155.70, 148.71, 148.52, 131.35, 128.96, 128.40, 127.58, 125.58, 125.40, 124.16, 121.65, 121.25, 114.62, 111.83, 16.09.

2-Amino-4-(4-hydroxyl-3,5-dimethylphenyl)-quinoline (87)

General procedure B was applied using 4-bromonaphthalen-2-amine (46 mg, 0.21 mmol), 2,4-dimethyl-4-(4,4,5,5-tetramethyl-1,3,2-dioxaborolan-2-yl)-phenol (50 mg, 0.21 mmol), K$_2$CO$_3$ (29 mg, 0.21 mmol) and [1,1'-bis(diphenylphosphino)ferrocene]palladium(II) dichloride (10 mg, 0.01 mmol), to give light yellow solid (26 mg, 49%). ESI-MS m/z: 265.1346 [M+H]$^+$; Purity: 97.7%. $^1$H NMR (400 MHz, DMSO-d$_6$) δ 8.56 (s, 1H), 7.64-7.41 (m, 3H), 7.11 (ddd, J=8.3, 6.5, 1.6 Hz, 1H), 7.03 (s, 2H), 6.61 (s, 1H), 6.47 (s, 2H), 2.24 (s, 6H). $^{13}$C NMR (101 MHz, DMSO) δ 157.76, 153.49, 148.78, 148.33, 128.97, 128.94, 128.69, 128.48, 125.47, 125.45, 124.39, 121.64, 121.26, 111.83, 16.72.

2-Amino-3-(4-hydroxyl-3-methylphenyl)-quinoline (88)

General procedure B was applied using 3-bromonaphthalen-2-amine (45 mg, 0.20 mmol), 2-methyl-4-(4,4,5,5-tetramethyl-1,3,2-dioxaborolan-2-yl)-phenol (47 mg, 0.20 mmol), K$_2$CO$_3$ (83 mg, 0.60 mmol) and [1,1'-bis(diphenylphosphino)ferrocene]palladium(II) dichloride (10 mg, 0.01 mmol), to give light yellow solid (42 mg, 84%). ESI-MS m/z: 251.1192 [M+H]$^+$; Purity: 98.5%. $^1$H NMR (400 MHz, DMSO-d$_6$) δ 9.56 (s, 1H), 7.74 (s, 1H), 7.67 (dt, J=8.0, 1.1 Hz, 1H), 7.52-7.43 (m, 2H), 7.22 (dd, J=2.4, 0.9 Hz, 1H), 7.20-7.09 (m, 2H), 6.89 (d, J=8.2 Hz, 1H), 6.01-5.91 (m, 2H), 2.18 (s, 3H). $^{13}$C NMR (101 MHz, DMSO) δ 156.07, 155.36, 146.86, 135.94, 131.01, 128.85, 127.92, 127.49, 127.04, 125.04, 124.80, 124.49, 123.67, 121.57, 115.02, 16.14.

2-Amino-4-(4-hydroxyl-3,5-dimethylphenyl)-3-pentylquinoline (89)

General procedure B was applied using 2-amino-4-trifluromethoxyl-3-pentylquinoline (41 mg, 0.12 mmol), 2-methyl-4-(4,4,5,5-tetramethyl-1,3,2-dioxaborolan-2-yl)-phenol (23 mg, 0.10 mmol), K$_2$CO$_3$ (27 mg, 0.30 mmol) and [1,1'-bis(diphenylphosphino)ferrocene]palladium(II) dichloride (10 mg, 0.01 mmol), to give light yellow solid (18 mg, 47%). ESI-MS m/z: 321.1967 [M+H]$^+$; Purity: 98.1%. $^1$H NMR (400 MHz, DMSO-d$_6$) δ 9.48 (s, 1H), 7.47 (dt, J=8.3, 1.0 Hz, 1H), 7.38 (ddd, J=8.3, 5.3, 3.0 Hz, 1H), 7.04-6.97 (m, 2H), 6.93-6.88 (m, 2H), 6.83 (dd, J=8.1, 2.1 Hz, 1H), 6.32 (s, 2H), 2.41-2.30 (m, 2H), 2.17 (s, 3H), 1.38 (d, J=8.2 Hz, 2H), 1.19-1.06 (m, 4H), 0.79-0.72 (t, J=7.6 Hz, 3H). $^{13}$C NMR (101 MHz, DMSO) δ 157.35, 155.17, 147.05, 139.29, 131.64, 128.38, 127.89, 127.79, 126.48, 125.13, 124.28, 124.22, 122.59, 121.45, 114.85, 31.62, 28.25, 28.20, 22.10, 16.48, 14.22.

4-Chloro-3-nitroquinoline (126)

3-Nitro-4-quinolinol (95 mg, 0.50 mmol) was stirred in POCl$_3$ (5 mL) at 90° C. overnight. The reaction was then quenched with saturated sodium carbonate solution and extracted with ethyl acetate (50 mL×3). The combined organic layers were dried over magnesium sulfate, filtered and concentrated. The residue was purified by flash column chromatography on silica gel (eluent: dichloromethane/ethyl acetate, 10-100%) to give the title compound as a white solid (82 mg, 79%). $^1$H NMR (400 MHz, Chloroform-d) δ 9.28 (s, 1H), 8.45 (ddd, J=8.5, 1.4, 0.6 Hz, 1H), 8.23 (ddd, J=8.5, 1.3, 0.7 Hz, 1H), 7.97 (ddd, J=8.5, 7.0, 1.5 Hz, 1H), 7.87-7.80 (m, 1H). 4-(4-Hydroxyl-3-methylphenyl)-3-nitroquinoline (90) General procedure was applied using 126 (42 mg, 0.20 mmol), 2-methyl-4-(4,4,5,5-tetramethyl-1,3,2-dioxaborolan-2-yl)-phenol (47 mg, 0.20 mmol), K$_2$CO$_3$ (83 mg, 0.60 mmol) and [1,1'-bis(diphenylphosphino)ferrocene]palladium(II) dichloride (10 mg, 0.01 mmol), to give light yellow solid (38 mg, 68%). ESI-MS m/z: 279.0777[M−H]$^−$; Purity: 99.3%. $^1$H NMR (400 MHz, DMSO-d$_6$) δ 9.88 (s, 1H), 9.34 (s, 1H), 8.20 (d, J=8.4 Hz, 1H), 7.97 (ddd, J=8.4, 5.5, 2.9 Hz, 1H), 7.78-7.68 (m, 2H), 7.12 (d, J=2.2 Hz, 1H), 7.08-7.04 (m, 1H), 6.96 (d, J=8.2 Hz, 1H), 2.18 (s, 3H). $^{13}$C NMR (101 MHz, DMSO) δ 156.50, 148.33, 144.19, 142.40, 142.37, 132.28, 130.96, 129.44, 128.87, 127.87, 127.51, 126.29, 124.55, 121.71, 114.85, 16.02.

4-(4-Methoxyl-3-methylphenyl)-3-nitro-quinoline (91)

A solution of 90 (140 mg, 0.50 mmol), MeI, NaH and dioxane (3 mL) and was heated at 100 overnight. The mixture was then diluted with water and extracted with ethyl acetate. The organic phase was dried and concentrated. The crude product was purified by flash chromatography (dichloromethane/ethyl acetate 0-10%) to yield pure product as a yellow solid (128 mg, 87% yield). ESI-MS m/z: 293.0883 [M+H]$^+$; Purity: 95.1%. $^1$H NMR (400 MHz, DMSO-d$_6$) δ 9.38 (s, 1H), 8.22 (ddd, J=8.4, 1.3, 0.6 Hz, 1H), 7.99 (ddd, J=8.4, 6.8, 1.6 Hz, 1H), 7.74 (ddd, J=8.1, 6.7, 1.3 Hz, 1H), 7.68 (ddd, J=8.5, 1.6, 0.7 Hz, 1H), 7.28-7.21 (m, 2H), 7.14 (d, J=8.1 Hz, 1H), 3.89 (s, 3H), 2.22 (s, 3H). $^{13}$C NMR (101 MHz, DMSO) δ 158.02, 148.34, 144.26, 142.25, 142.14, 132.37, 130.63, 129.45, 128.93, 127.82, 127.76, 126.23, 126.13, 123.22, 110.49, 55.45, 16.09.

4-(4-Methoxyl-3-methylphenyl)-3-nitro-quinoline 1-oxide (92)

91 (60 mg, 0.20 mmol) was stirred with mCPBA (52 mg, 0.30 mmol) in DCM overnight, and reaction was then quenched with saturated sodium carbonate solution and extracted with ethyl acetate (50 mL×3). The combined organic layers were dried over magnesium sulfate, filtered and concentrated. The residue was purified by flash column chromatography on silica gel (eluent: dichloromethane/ethyl acetate, 10-100%) to give the title compound as a light yellow solid (45 mg, 73%). ESI-MS m/z: 311.1034 [M+H]$^+$; Purity: 99.5%. $^1$H NMR (400 MHz, DMSO-d$_6$) δ 9.26 (s, 1H), 8.66 (dd, J=8.7, 1.2 Hz, 1H), 8.02 (ddd, J=8.6, 6.9, 1.3 Hz, 1H), 7.84 (ddd, J=8.3, 6.9, 1.3 Hz, 1H), 7.73-7.69 (m, 1H), 7.25-7.20 (m, 2H), 7.13 (d, J=8.2 Hz, 1H), 3.88 (s, 3H), 2.21 (s, 3H). $^{13}$C NMR (101 MHz, DMSO) δ 158.01, 142.80, 142.08, 132.82, 131.10, 130.70, 130.68, 129.87, 128.99, 128.52, 128.25, 126.15, 122.76, 119.28, 110.53, 55.45, 16.09.

2-Amino-4-(4-methoxyl-3-methylphenyl)-quinoline (93)

A solution of 91 (61 mg, 0.20 mmol) in ethanol was added Pd/C and stirred in hydrogen atmosphere at room temperature overnight. The mixture was then diluted with water and extracted with ethyl acetate. The organic phase was dried and concentrated. The crude product was purified by flash chromatography (dichloromethane/ethyl acetate 0-10%) to yield pure (42 mg, 79% yield) as a yellow solid. ESI-MS m/z: 263.1191 [M−H]$^-$; Purity: 99.3%. $^1$H NMR (400 MHz, DMSO-d$_6$) δ 8.57 (s, 1H), 7.84-7.79 (m, 1H), 7.37-7.28 (m, 2H), 7.26-7.21 (m, 1H), 7.16-7.06 (m, 3H), 5.09 (s, 2H), 3.87 (s, 3H), 2.22 (s, 3H). $^{13}$C NMR (101 MHz, DMSO) δ 156.92, 143.44, 141.38, 138.87, 131.87, 128.94, 128.61, 128.39, 126.44, 125.88, 123.78, 123.43, 122.70, 110.96, 55.31, 16.21.

2-Hydroxyl-4-(4-methoxyl-3-methylphenyl)-3-nitro-quinoline (94)

92 (62 mg, 0.20 mmol) was stirred in POCl$_3$ (5 mL) at 90° C. overnight. The reaction was then quenched with saturated sodium carbonate solution and extracted with ethyl acetate (50 mL×3). The combined organic layers were dried over magnesium sulfate, filtered and concentrated. The intermediate was then dissolved in DMF/H$_2$O (3 mL/1 mL), and NaOH (40 mg, 0.20 mmol) was added, the mixture was stirred at 90° C. overnight. The reaction was neutralized and extracted with ethyl acetate (50 mL×3). The combined organic layers were dried over magnesium sulfate, filtered and concentrated. The residue was purified by flash column chromatography on silica gel (eluent: dichloromethane/ethyl acetate, 10-100%) to give the title compound as a white solid (22 mg, 79%). ESI-MS m/z: 311.1030 [M+H]$^+$; Purity: 92.9%. $^1$H NMR (400 MHz, DMSO-d$_6$) δ 12.83 (s, 1H), 7.69 (dddd, J=8.4, 5.6, 2.6, 1.4 Hz, 1H), 7.47 (d, J=8.1 Hz, 1H), 7.30-7.16 (m, 4H), 7.11 (d, J=8.3 Hz, 1H), 3.86 (s, 3H), 2.19 (s, 3H). $^{13}$C NMR (101 MHz, DMSO) δ 158.41, 153.98, 142.94, 141.78, 138.17, 132.72, 130.24, 128.21, 127.46, 126.31, 123.40, 121.67, 117.61, 116.23, 110.56, 55.47, 16.05.

3-Amino-4-(4-methoxyl-3-methylphenyl)-2-N,N-dimethyl-quinoline (95)

94 (62 mg, 0.20 mmol) was stirred in POCl$_3$ (5 mL) at 90° C. overnight. The reaction was then quenched with saturated sodium carbonate solution and extracted with ethyl acetate (50 mL×3). The combined organic layers were dried over magnesium sulfate, filtered and concentrated. The intermediate was then dissolved in DMF (3 mL), and dimethylamine (9 mg, 0.20 mmol) was added, the mixture was stirred at 90° C. overnight. The reaction was neutralized and extracted with ethyl acetate (50 mL×3). The combined organic layers were dried over magnesium sulfate, filtered and concentrated. The residue was purified by flash column chromatography on silica gel (eluent: dichloromethane/ethyl acetate, 10-100%) to give the title compound as a white solid (52 mg, 77%). ESI-MS m/z: 308.1758 [M+H]f; Purity: 98.8%. $^1$H NMR (400 MHz, DMSO-d$_6$) δ 7.67 (d, J=8.2 Hz, 1H), 7.35-7.27 (m, 1H), 7.20-7.06 (m, 5H), 3.90-3.82 (s, 3H), 2.88 (s, 6H), 2.23 (s, 3H). $^{13}$C NMR (101 MHz, DMSO)$^{13}$C NMR (101 MHz, DMSO) δ 157.01, 153.91, 140.10, 132.30, 132.05, 128.82, 127.13, 126.55, 126.49, 126.47, 124.91, 124.34, 124.07, 123.31, 111.05, 55.36, 40.88, 16.23.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

What is claimed is:

1. A compound comprising the chemical formula:

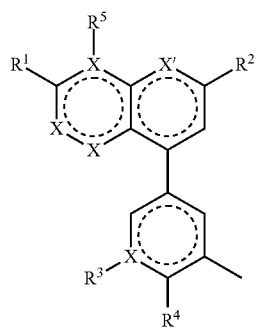

or a pharmaceutically acceptable salt thereof, wherein:
X is independently N or C, wherein when one X position is N, the other X positions are C;
X' is N;
R1 is H, —OH, —OMe, —C(O)CH$_3$, —CO$_2$CH$_3$, —CO$_2$(CH$_2$)$_2$CH$_3$, —CO$_2$(CH$_2$)$_4$OH, —CO$_2$(CH$_2$)$_3$CH$_3$, —O(CH$_2$)$_3$CH$_3$, —O(CH$_2$)$_4$CH$_2$(CH$_2$)$_2$, or —Cl;
R2 is H, or NH$_2$;
R3 is absent, H or —CH$_3$;
R4 is —OH, —O(CH$_2$)$_3$CH$_3$, —O(CH$_2$)$_4$OH, —OMe, or —OCH$_2$—C$_6$H$_5$, wherein when R1-R3, and R5 are H, R4 is not —OH; and
R5 is absent or H; or
R1 and R5 together form a 5- or 6-membered unsubstituted, aromatic, heterocyclic ring comprising one or two heterocyclic atoms selected from nitrogen, oxygen or carbon; and
wherein said dashed lines represents possible double bond positions according to the configuration of X and/or R1-R5.

2. A pharmaceutical composition comprising a compound of claim 1, and a pharmaceutically acceptable excipient.

3. A method of inhibiting TLR8 in an individual, the method comprising: administering to the individual the pharmaceutical composition of claim 2 in an amount effective to inhibit the TLR8 activity in the individual.

4. A method of treating inflammation in an individual, the method comprising: administering to the individual the pharmaceutical composition of claim 2 in an amount effective to inhibit TLR8 activity in the individual.

5. The method of claim 4, wherein said inflammation comprises inflammation caused by an autoimmune disease.

6. The method of claim 5, wherein said inflammation caused by an autoimmune disease comprises inflammation caused by an autoimmune disease selected from the group consisting of: arthritis, rheumatoid arthritis (RA), systemic lupus erythematosus (SLE), systemic scleroderma (SSc), multiple sclerosis (MS), Sjögren's syndrome, autoimmune hepatitis, systemic onset arthritis, Still's Disease (ASOD), Osteoarthritis (OA), Crohn's disease, irritable bowel disease (IBD), ulcerative colitis, polymyositis, type I diabetes mellitus, glomerulonephritis, pyelitis, autoimmune pancreatitis (AIP), sclerosing cholangitis, autoimmune skin disease, uveitis, psoriasis, antiphospholipid syndrome (APS), pernicious anemia, hypoparathyroidism, polyangiitis overlap syndrome, kawasaki's disease, sarcoidosis, vitiligo, pemphigus vulgaris, pemphigus foliaceus, hypopituitarism, and cryopathies.

7. A compound comprising the chemical formula selected from the group consisting of:

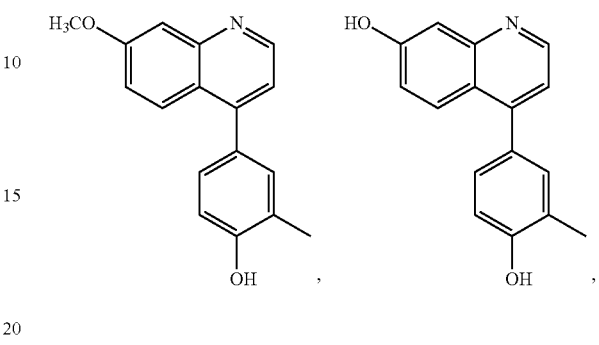

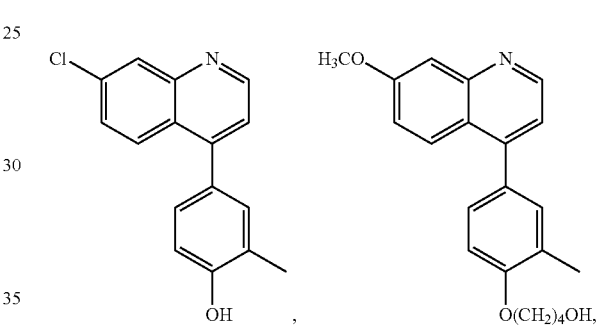

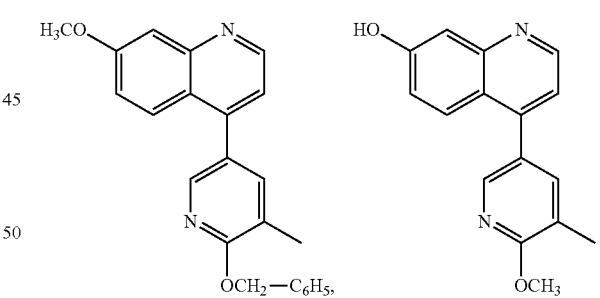

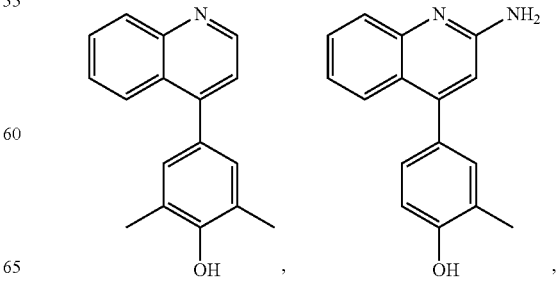

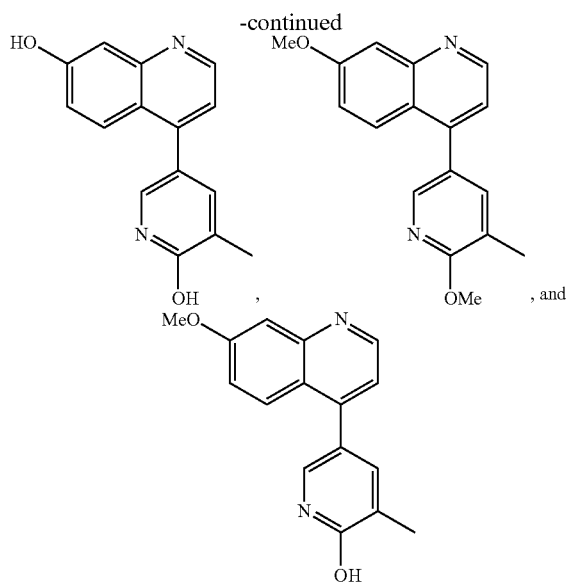

or a pharmaceutically acceptable salt thereof.

8. A pharmaceutical composition comprising one or more compounds of claim 7, and a pharmaceutically acceptable excipient.

9. A method of inhibiting TLR8 in an individual, the method comprising: administering to the individual the pharmaceutical composition of claim 8 in an amount effective to inhibit the TLR8 activity in the individual.

10. A method of treating inflammation in an individual, the method comprising: administering to the individual the pharmaceutical composition of claim 8 in an amount effective to inhibit TLR8 activity in the individual.

11. The method of claim 10, wherein said inflammation comprises inflammation caused by disease or condition selected from the group consisting of: arthritis, rheumatoid arthritis (RA), systemic lupus erythematosus (SLE), systemic scleroderma (SSc), multiple sclerosis (MS), Sjögren's syndrome, autoimmune hepatitis, systemic onset arthritis, Still's Disease (ASOD), Osteoarthritis (OA), Crohn's disease, irritable bowel disease (IBD), ulcerative colitis, polymyositis, type I diabetes mellitus, glomerulonephritis, pyelitis, autoimmune pancreatitis (AIP), sclerosing cholangitis, autoimmune skin disease, uveitis, psoriasis, antiphospholipid syndrome (APS), pernicious anemia, hypoparathyroidism, polyangiitis overlap syndrome, kawasaki's disease, sarcoidosis, vitiligo, pemphigus vulgaris, pemphigus foliaceus, hypopituitarism, and cryopathies.

12. A compound comprising the chemical formula:

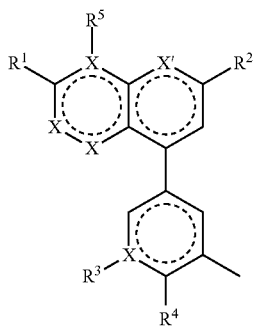

or a pharmaceutically acceptable salt thereof, wherein:
X is independently N or C, wherein when one X position is N, the other X positions are C;
X' is N; and
R1-R5 are selected from H, alkyl, —OCH$_2$C$_6$H$_5$, —OH, Cl, NH$_2$, and alkoxy; and
wherein R4 is not H, and when R1-R3, and R5 are H, R4 is not —OH.

13. A pharmaceutical composition comprising one or more compounds of claim 12, and a pharmaceutically acceptable excipient.

14. A method of inhibiting TLR8 in an individual, the method comprising: administering to the individual the pharmaceutical composition of claim 13 in an amount effective to inhibit the TLR8 activity in the individual.

15. A method of treating inflammation in an individual, the method comprising: administering to the individual the pharmaceutical composition of claim 12 in an amount effective to inhibit TLR8 activity in the individual.

16. The method of claim 15, wherein said inflammation comprises inflammation caused by disease or condition selected from the group consisting of: arthritis, rheumatoid arthritis (RA), systemic lupus erythematosus (SLE), systemic scleroderma (SSc), multiple sclerosis (MS), Sjögren's syndrome, autoimmune hepatitis, systemic onset arthritis, Still's Disease (ASOD), Osteoarthritis (OA), Crohn's disease, irritable bowel disease (IBD), ulcerative colitis, polymyositis, type I diabetes mellitus, glomerulonephritis, pyelitis, autoimmune pancreatitis (AIP), sclerosing cholangitis, autoimmune skin disease, uveitis, psoriasis, antiphospholipid syndrome (APS), pernicious anemia, hypoparathyroidism, polyangiitis overlap syndrome, kawasaki's disease, sarcoidosis, vitiligo, pemphigus vulgaris, pemphigus foliaceus, hypopituitarism, and cryopathies.

* * * * *